(12) United States Patent
Ludemann et al.

(10) Patent No.: US 9,583,717 B2
(45) Date of Patent: Feb. 28, 2017

(54) COMPOUNDS FOR ORGANIC ELECTROLUMINESCENT DEVICES

(75) Inventors: Aurélie Ludemann, Frankfurt am Main (DE); Alice Julliart, Caluire-et-Cuire (FR); Anna Hayer, Mainz (DE); Anja Gerhard, Egelsbach (DE); Dominik Joosten, Frankfurt am Main (DE); Holger Heil, Frankfurt am Main (DE); Fabrice Eckes, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 436 days.

(21) Appl. No.: 14/130,957

(22) PCT Filed: Jun. 29, 2012

(86) PCT No.: PCT/EP2012/002752
§ 371 (c)(1),
(2), (4) Date: Jan. 6, 2014

(87) PCT Pub. No.: WO2013/007348
PCT Pub. Date: Jan. 17, 2013

(65) Prior Publication Data
US 2014/0138661 A1    May 22, 2014

(30) Foreign Application Priority Data
Jul. 11, 2011 (EP) .................... 11005644

(51) Int. Cl.
| | | |
|---|---|---|
| H01L 51/50 | (2006.01) | |
| H01L 51/00 | (2006.01) | |
| C07D 405/14 | (2006.01) | |
| C07D 317/28 | (2006.01) | |
| C07D 333/76 | (2006.01) | |
| C07D 405/04 | (2006.01) | |
| C07D 251/42 | (2006.01) | |
| C07D 491/048 | (2006.01) | |
| C07D 495/04 | (2006.01) | |
| C07D 209/86 | (2006.01) | |
| C07C 211/61 | (2006.01) | |
| C07C 223/06 | (2006.01) | |
| C07C 225/22 | (2006.01) | |

(52) U.S. Cl.
CPC .......... *H01L 51/006* (2013.01); *C07C 211/61* (2013.01); *C07C 223/06* (2013.01); *C07C 225/22* (2013.01); *C07D 209/86* (2013.01); *C07D 251/42* (2013.01); *C07D 317/28* (2013.01); *C07D 333/76* (2013.01); *C07D 405/04* (2013.01); *C07D 405/14* (2013.01); *C07D 491/048* (2013.01); *C07D 495/04* (2013.01); *H01L 51/0059* (2013.01); *H01L 51/0061* (2013.01); *H01L 51/0072* (2013.01); *C07C 2102/06* (2013.01); *C07C 2103/18* (2013.01); *C07C 2103/94* (2013.01); *H01L 51/0037* (2013.01); *H01L 51/0085* (2013.01); *H01L 51/5056* (2013.01); *Y02E 10/549* (2013.01)

(58) Field of Classification Search
None
See application file for complete search history.

(56) References Cited

U.S. PATENT DOCUMENTS

| | | |
|---|---|---|
| 2004/0206939 A1 | 10/2004 | Spreitzer et al. |
| 2004/0225056 A1 | 11/2004 | Spreitzer et al. |
| 2005/0040390 A1 | 2/2005 | Pfeiffer et al. |
| 2005/0121667 A1 | 6/2005 | Kuehl et al. |
| 2008/0191617 A1 | 8/2008 | Chae et al. |
| 2009/0062223 A1 | 3/2009 | Keicher et al. |
| 2010/0045171 A1 | 2/2010 | Katakura et al. |
| 2010/0108991 A1 | 5/2010 | Tanaka et al. |
| 2010/0207105 A1* | 8/2010 | Katakura ............ C07D 209/86 257/40 |
| 2012/0001127 A1 | 1/2012 | Brown et al. |
| 2012/0193619 A1 | 8/2012 | Taka et al. |

FOREIGN PATENT DOCUMENTS

| | | | |
|---|---|---|---|
| EP | 1476881 A2 | 11/2004 | |
| EP | 1596445 A1 | 11/2005 | |
| EP | 2194582 A1 | 6/2010 | |
| JP | 2001166518 A | 6/2001 | |
| JP | 2007110097 A | 4/2007 | |
| JP | 2008066569 A | 3/2008 | |
| JP | 2008207520 A | 9/2008 | |
| JP | 2009135183 A | 6/2009 | |
| JP | 2009176963 A | 8/2009 | |
| JP | 2010-040967 * | 2/2010 | ............ H01L 51/50 |
| JP | 2010037312 A | 2/2010 | |
| JP | 2010040830 A | 2/2010 | |
| JP | 2011113650 A | 6/2011 | |
| JP | 2012151266 A | 8/2012 | |
| JP | 2013033915 A | 2/2013 | |
| JP | 2014075605 A | 4/2014 | |
| WO | WO-02/072714 A1 | 9/2002 | |
| WO | WO-03/019694 A2 | 3/2003 | |
| WO | WO-2007114244 A1 | 10/2007 | |
| WO | WO-2008029652 A1 | 3/2008 | |
| WO | WO-2008029729 A1 | 3/2008 | |
| WO | WO-2009029729 A1 | 3/2009 | |
| WO | WO-2011046166 A1 | 4/2011 | |
| WO | WO-2011093309 A1 | 8/2011 | |
| WO | WO-2012003485 A2 | 1/2012 | |

OTHER PUBLICATIONS

International Search Report for PCT/EP2012/002752 mailed Sep. 26, 2012.

* cited by examiner

*Primary Examiner* — Gregory Clark
(74) *Attorney, Agent, or Firm* — Drinker Biddle & Reath LLP

(57) ABSTRACT

The present invention relates to crosslinkable compounds, to the crosslinked compounds obtained from these compounds, and to processes for the preparation thereof. The invention is furthermore directed to the use of these compounds in electronic devices and to the corresponding electronic devices themselves.

18 Claims, No Drawings

COMPOUNDS FOR ORGANIC ELECTROLUMINESCENT DEVICES

RELATED APPLICATIONS

This application is a national stage application (under 35 U.S.C. §371) of PCT/EP2012/002752, filed Jun. 29, 2012, which claims benefit of European Application No. 11005644.7, filed Jul. 11, 2011, which is incorporated by reference herein.

The present invention relates to crosslinkable compounds, to the crosslinked compounds obtained from these compounds, and to processes for the preparation thereof. The invention is furthermore directed to the use of these compounds in electronic devices, in particular in organic electroluminescent devices, and to the corresponding electronic devices themselves.

Electronic devices which comprise organic and/or organometallic semiconductors are being used more and more frequently in commercial products. Examples which may be mentioned here are charge-transport materials on an organic basis (for example triarylamine-based hole-transport materials) in photocopiers, organic light-emitting diodes (OLED) or organic photoreceptors in copiers. Organic solar cells (O-SC), organic field-effect transistors (O-FET), organic thin-film transistors (O-TFT), organic integrated circuits (O-IC), organic optical amplifiers and organic laser diodes (O-lasers) are at an advanced stage of development and may achieve major importance in the future.

Many of these electronic devices have, independently of the respective application, the following general layer structure, which can be adapted for the particular application:
(1) substrate,
(2) electrode, frequently metallic or inorganic, but also comprising organic or polymeric conductive materials,
(3) optionally charge-injection layer(s) or interlayer(s), for example for compensation of unevenness of the electrode, frequently comprising a conductive, doped polymer,
(4) organic semiconductors, for example as emitting layer,
(5) possibly further charge-transport, charge-injection or charge-blocking layers,
(6) counterelectrode, materials as mentioned under (2),
(7) encapsulation.

For organic electroluminescent devices, at least one of the electrodes must be transparent or partially transparent.

The above arrangement represents the general structure of an organic electronic device, where various layers can be combined, resulting in the simplest case in an arrangement comprising two electrodes, between which an organic layer is located. In this case, the organic layer fulfils all functions, including the emission of light in the case of OLEDs.

However, a problem which arises in a "three-layer system" of this type with only one organic layer is the lack of control of charge separation and the lack of a way of optimising the individual constituents in different layers with respect to their properties, as is achieved in a simple manner, for example, in the case of OLEDs based on vapour-deposited low-molecular-weight compounds due to a multilayered structure.

An OLED based on vapour-deposited low-molecular-weight compounds consists, for example, of one or more organic hole-injection layers, hole-transport layers, excitonblocking layers, emission layers, hole-blocking layers, electron-transport layers and/or electron-injection layers, and an anode and a cathode. The advantage of a multilayered structure of this type consists in that the various functions of charge injection, charge transport and emission can be spread over different layers and the properties of the respective layers can thus be modified and optimised separately.

The layers in an OLED of this type are usually applied by vapour deposition in a vacuum chamber. However, this process is complex and thus expensive and is unsuitable, in particular, for relatively high-molecular-weight compounds, such as, for example, polymers. Polymeric OLED materials are therefore usually applied by coating from solution. Processing from solution would also be desirable for low-molecular-weight organic compounds owing to the high technical complexity in the case of vacuum processing. The production of a multilayered, organic structure by coating from solution requires that the solvent of the layer to be applied does not re-dissolve, swell or even destroy the respective prior layer. However, the choice of solvent proves to be difficult, since the organic compounds employed usually have similar chemical structures and properties, in particular similar dissolution properties.

Correspondingly, solution-processed OLEDs based on polymers or soluble low-molecular-weight compounds in accordance with the prior art are usually built up only from a single-layered or at most two-layered, organic structure, where, for example, one of the layers is used for hole injection and hole transport and the second layer is used, for example, for the injection and transport of electrons and for emission.

It has been found here that it may be appropriate to insert a hole-transporting interlayer, which can also act as exciton- or electron-blocking layer, between the anode or a hole-injection layer comprising a conductive doped polymer, for example PEDOT/PSS. This enables the properties of the OLED to be significantly improved. The further layers can then be applied to this interlayer. If the further layers are to be applied from solution, it is necessary, as mentioned above, that the hole-transporting interlayer does not dissolve.

It is possible to build up a multilayered structure of this type by, for example, crosslinking and thus rendering insoluble a layer after application from solution and before application of the next layer (for example EP 0637899, U.S. Pat. No. 6,107,452). However, it has been found that not all chemical structures are equally suitable for this purpose.

As crosslinking activation, temperature treatment is generally preferred over UV irradiation, since a thermal drying process is generally carried out anyway in order to remove the solvent in the case of organic semiconductors applied from solution. Thus, the crosslinking process can easily be integrated into the production process and damage to the semiconducting material by UV radiation can be excluded. It is likewise preferred to avoid the use of an initiator. For the thermal crosslinking, the temperature is selected in such a way that the crosslinking reaction can take place. It is desirable here to select a temperature range in which the crosslinkable material and the other materials already present in the layer structure do not decompose.

In particular in the case of blue, the OLEDs processed from solution still have inferior performance to vapour-deposited low-molecular-weight compounds. A main reason for this is evident in the properties of the interlayer introduced between the anode or the layer comprising a conductive doped polymer and the emitting layer. The coupling of many aromatic systems in a polymer means that the energy gap and the HOMO and LUMO levels cannot be set as precisely as in the case of defined low-molecular-weight compounds. Polymer defects, incomplete end capping, relatively difficult purification and the polydispersity of polymers are likewise regarded as weak points of the polymer interlayer, particularly in the case of blue-emitting OLEDs. The same applies to phosphorescent OLEDs, in particular to green-phosphorescent OLEDs.

There is a demand for compounds which have hole-transport properties and are thus suitable for use in a hole-transport or hole-injection layer, especially also in an interlayer, and which contain groups which are suitable for crosslinking. It is advantageous here for these crosslinkable groups to be crosslinked easily, i.e. with low expenditure of energy, and, even in the crosslinked state, to have no negative effects on the function of the electronic device. The compounds should furthermore result in advantageous properties with respect to efficiency, lifetime and voltage of the OLED or at least not impair them compared with the corresponding uncrosslinked compounds or compared with crosslinked polymers.

The object of the present invention was thus the provision of such compounds.

Surprisingly, it has been found that certain arylamine derivatives, described in greater detail below, which are substituted by at least two crosslinkable groups achieve this object. Particularly efficient and long-lived OLEDs, in particular also those which are based on triplet emission or on blue singlet emission, can be built up using these crosslinkable compounds. The crosslinkable compounds can be crosslinked thermally or optically, with or without initiator, on the substrate or on a layer comprising a conductive doped polymer and in this way allow the controlled application of a further layer from solution. This operation can also be repeated a number of times, where either the same or different crosslinkable compounds can be used for this purpose.

The present invention therefore relates to a compound of the following formula (1),

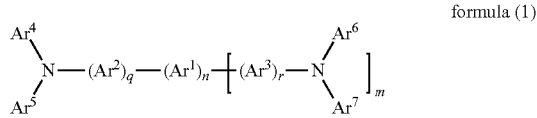

formula (1)

where the following applies to the symbols and indices used:

$Ar^1$ is, identically or differently on each occurrence, a group of the following formula (2),

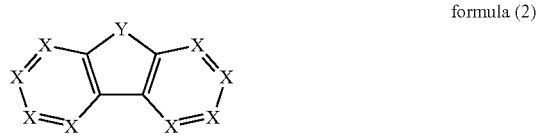

formula (2)

where the structure of the formula (2) can be linked at any desired positions to $Ar^2$ and $Ar^3$ or to N or to further groups $Ar^1$ for n>1;

Y is N if the group of the formula (2) is linked via this N to $Ar^2$ or $Ar^3$ or N or $Ar^1$ for n>1 or is, identically or differently on each occurrence, NR, O, S, CR=CR, $CR_2$—$CR_2$ or a group of the following formula (3),

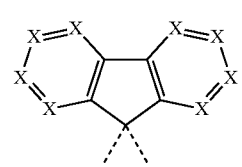

formula (3)

where the dashed bonds denote the linking of the group; or Y may furthermore also stand for $CR_2$ if two adjacent groups X together stand for a group of the formula (4), (5) or (6);

X is C if the group of the formula (2) is linked via this X to $Ar^2$ or $Ar^3$ or N or $Ar^1$ for n>1 or is, identically or differently on each occurrence, CR or N; or two adjacent groups X together stand for a group of the following formula (4), (5) or (6),

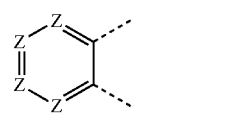

formula (4)

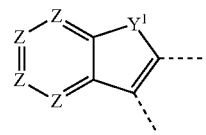

formula (5)

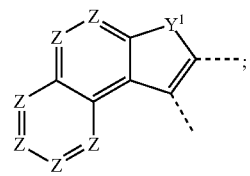

formula (6)

where the dashed bonds denote the linking of the group;

Z is C if the group of the formula (4) or formula (5) or formula (6) is linked via this X to $Ar^2$ or $Ar^3$ or N or $Ar^1$ for n>1 or is on each occurrence, identically or differently, CR or N;

$Y^1$ is on each occurrence, identically or differently, $CR_2$, NR, O or S;

$Ar^2$, $Ar^3$ is on each occurrence, identically or differently, an aryl or heteroaryl group having 5 to 18 aromatic ring atoms, which may be substituted by one or more radicals R;

$Ar^4$ to $Ar^7$ is on each occurrence, identically or differently, an aromatic or heteroaromatic ring system having 5 to 24 aromatic ring atoms, which may be substituted by one or more radicals R; $Ar^4$ and $Ar^5$ and/or $Ar^4$ and $Ar^2$ and/or $Ar^5$ and $Ar^2$ and/or $Ar^6$ and $Ar^7$ and/or $Ar^6$ and $Ar^3$ and/or $Ar^7$ and $Ar^3$ here may be connected to one another by a group E;

E is on each occurrence, identically or differently, a single bond or a group selected from $CR_2$, O, S or NR;

R is on each occurrence, identically or differently, H, D, F, Cl, Br, I, $N(R^1)_2$, CN, $NO_2$, $Si(R^1)_3$, $B(OR^1)_2$, C(=O)$R^1$, P(=O)$(R^1)_2$, S(=O)$R^1$, S(=O)$_2R^1$, $OSO_2R^1$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals $R^1$, where one or more non-adjacent CH$_2$ groups may be replaced by R$^1$C=CR$^1$, C≡C, Si(R$^1$)$_2$, C=O, C=S, C=NR$^1$, P(=O)(R$^1$), SO, SO$_2$, NR$^1$, O, S or CONR$^1$ and where one or more H atoms may be replaced by D, F, Cl, Br, I or CN, or an aromatic or heteroaromatic ring system having 5 to 60 aromatic ring atoms, which may in each case be substituted by one or more radicals R$^1$, or an aryloxy or heteroaryloxy group having 5 to 60 aromatic ring atoms, which may be substituted by one or more radicals R$^1$, or an aralkyl or heteroaralkyl group having 5 to 60 aromatic ring atoms, which may be substituted by one or more radicals R$^1$, or a diarylamino group, diheteroarylamino group or arylheteroarylamino group having 10 to 40 aromatic ring atoms, which may be substituted by one or more radicals R$^1$; two or more radicals R here may also form a mono- or polycyclic, aliphatic, aromatic and/or benzo-fused ring system with one another;

R$^1$ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R$^1$ here may also form a mono- or polycyclic, aliphatic or aromatic ring system with one another;

n is 1, 2, 3 or 4;

m is 1, 2 or 3;

q, r is, identically or differently on each occurrence, 0, 1, 2 or 3;

which is characterised in that at least two of the groups Ar$^4$ to Ar$^7$ are each substituted by a group of the following formula (7):

-L-(Ar$^8$)$_p$-Q        formula (7)

in which:

L is, identically or differently on each occurrence, a spacer group or a direct bond;

Ar$^8$ is, identically or differently on each occurrence, an aromatic or heteroaromatic ring system having 5 to 24 aromatic ring atoms, which may be substituted by one or more radicals R;

Q is, identically or differently on each occurrence, a crosslinkable group;

p is, identically or differently on each occurrence, 0 or 1.

"Crosslinkable group" in the sense of the present invention means a functional group which is capable of undergoing a reaction, preferably a polymerisation reaction, and thus forming an insoluble compound. The crosslinkable group is thus a polymerisable group. As a result of the reaction of the crosslinkable group, a corresponding cross-linked compound is obtained. The chemical reaction can also be carried out in the layer, with an insoluble layer forming. The crosslinking can usually be supported by heat or by UV, microwave, X-ray or electron radiation, if necessary in the presence of an initiator. "Insoluble" in the sense of the present invention preferably means that the compound has a solubility after the crosslinking reaction, i.e. after the reaction of the crosslinkable groups, in toluene at room temperature which is at least a factor of 3, preferably at least a factor of 10, lower than that of the uncrosslinked compound of the formula (1).

An aryl group in the sense of the present invention contains 6 to 40 C atoms; a heteroaryl group in the sense of the present invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of the present invention contains 6 to 60 C atoms in the ring system. A heteroaromatic ring system in the sense of the present invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of the present invention is to be taken to mean a system which does not necessarily contain only aryl or heteroaryl groups, but instead in which a plurality of aryl or heteroaryl groups may also be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also to be regarded as aromatic ring systems in the sense of the present invention, as are systems in which two or more aryl groups are interrupted, for example, by a linear or cyclic alkyl group or by a silyl group.

A cyclic alkyl, alkoxy or thioalkoxy group in the sense of the present invention is taken to mean a monocyclic, bicyclic or polycyclic group.

For the purposes of the present invention, a C$_1$- to C$_{40}$-alkyl group, in which, in addition, individual H atoms or CH$_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]octyl, 2-(2,6-dimethyl)octyl, 3-(3,7-dimethyl)octyl, trifluoromethyl, pentafluoroethyl or 2,2,2-trifluoroethyl.

An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl.

An alkynyl group is taken to mean, for example, ethynyl, propynyl, butynyl, pentynyl, hexynyl, heptynyl or octynyl. A C$_1$- to C$_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5 to 60 aromatic ring atoms, which may also in each case be substituted by the above-mentioned radicals R and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, cis- or trans-indenocarbazole, cis- or transindolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the present invention, the group $Ar^1$ is selected, identically or differently on each occurrence, from the groups of the following formulae (8) to (27), formula (8)
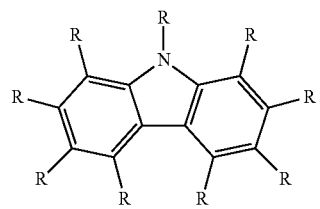

formula (9)
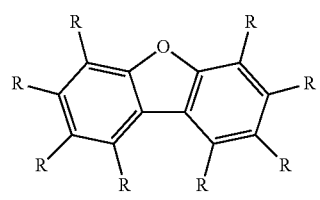

formula (10)
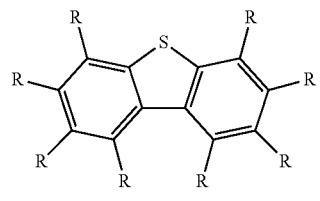

formula (11)
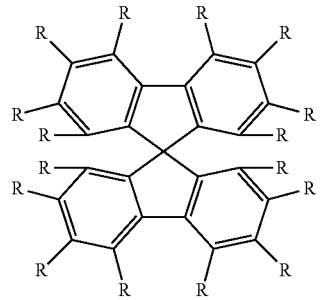

formula (12)
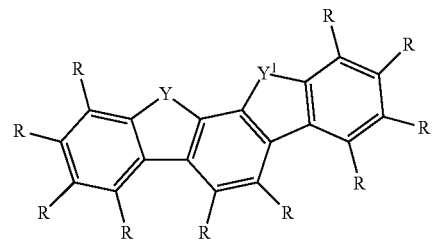

formula (13)
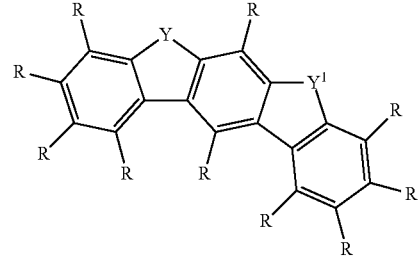

formula (14)
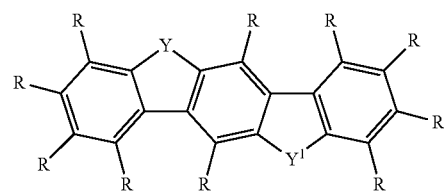

formula (15)
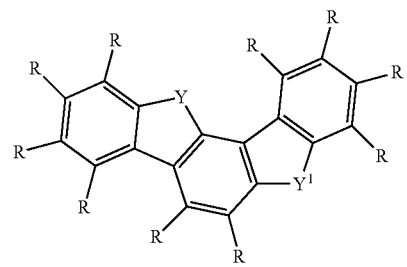

formula (16)
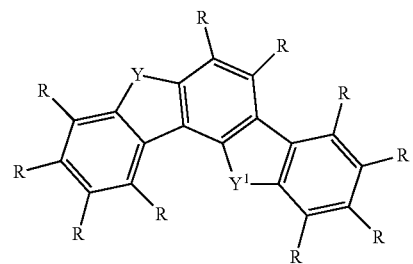

formula (17)
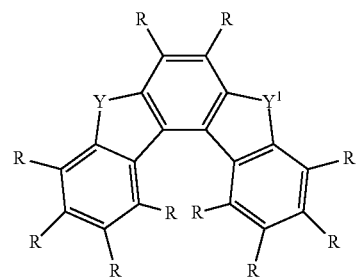

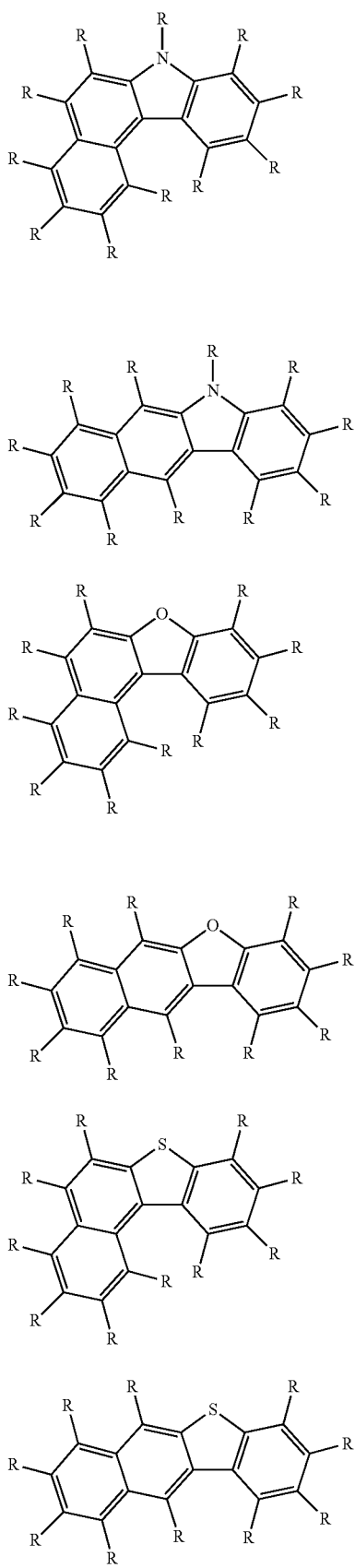

formula (18)

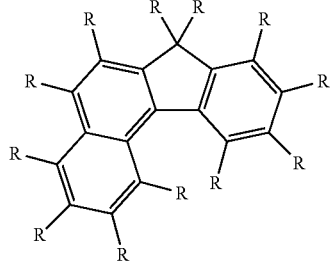

formula (19)

formula (20)

formula (21)

formula (22)

formula (23)

formula (24)

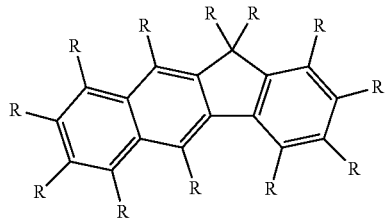

formula (25)

formula (26)

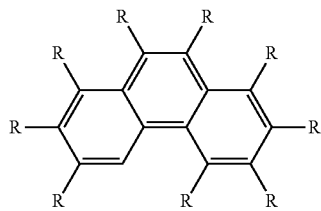

formula (27)

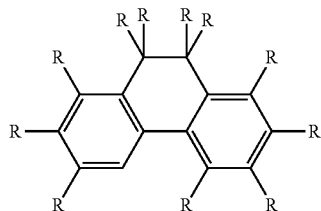

where Y, Y$^1$ and R have the meanings given above, and no radical R is present at the positions at which the structure is bonded to Ar$^2$ or Ar$^3$ or to the nitrogen or to a further group Ar$^1$ for n>1. The groups can each be bonded via any desired positions.

Particularly preferred groups Ar$^1$ are, identically or differently on each occurrence, the structures of the following formulae (8a) to (27b), formula (8a)

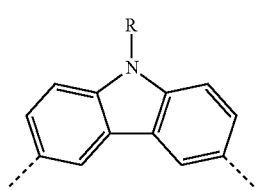

formula (8b)

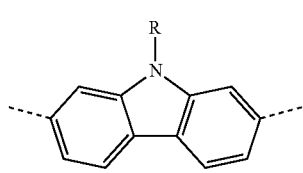

formula (8c)
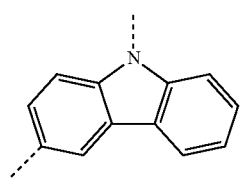
formula (8d)
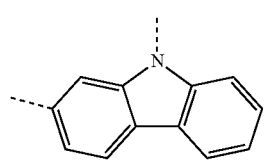
formula (8e)
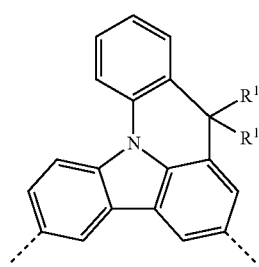
formula (8f)
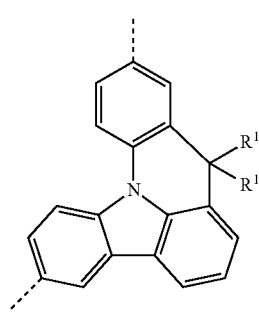
formula (9a)
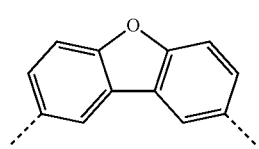
formula (9b)
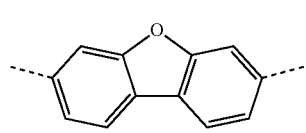
formula (10a)
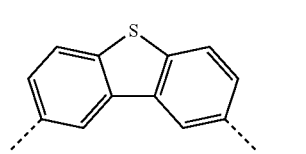
formula (10b)
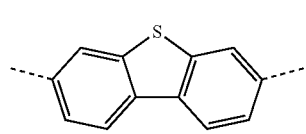
formula (11a)
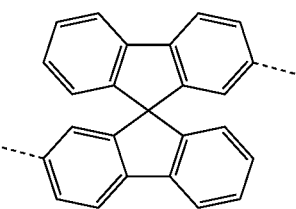
formula (11ba)
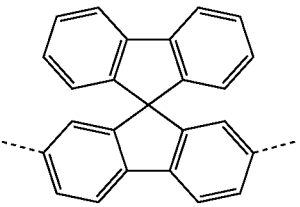
formula (11c)
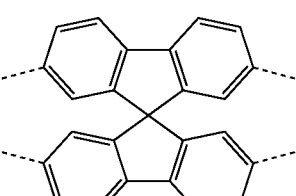
formula (11d)
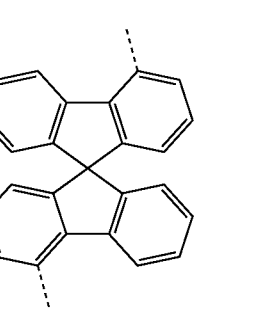
formula (11e)
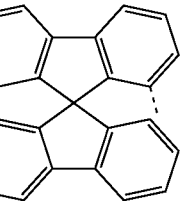
formula (11f)

formula (11g)
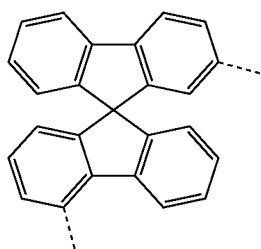
formula (11h)
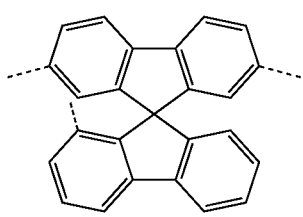
formula (11i)
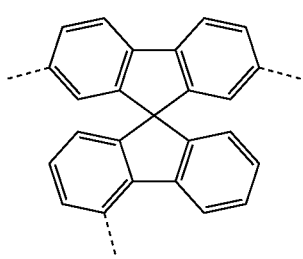
formula (12a)
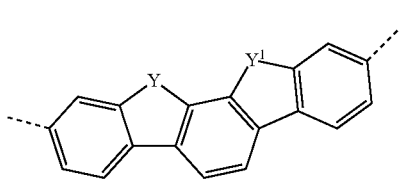
formula (12b)
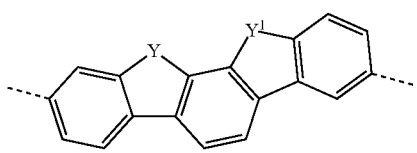
formula (12c)
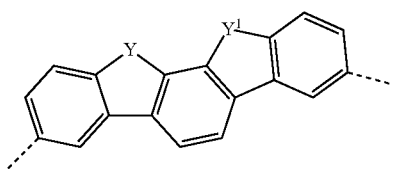
formula (13a)
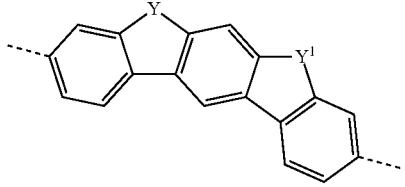
formula (13b)
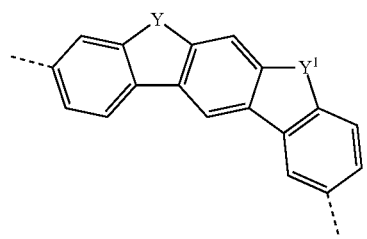
formula (13c)
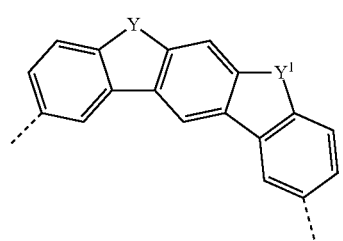
formula (14a)
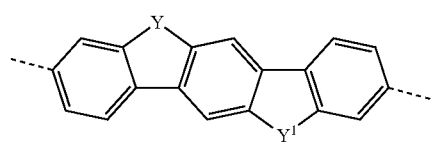
formula (14b)
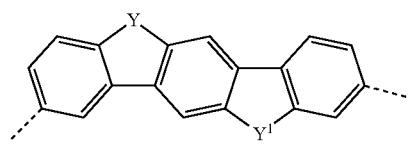
formula (14c)
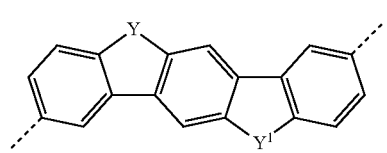
formula (15a)
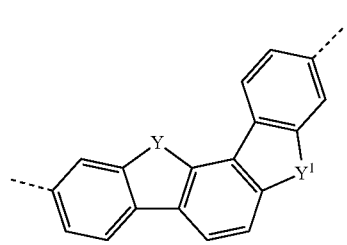
formula (15b)
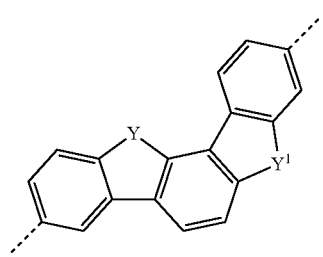

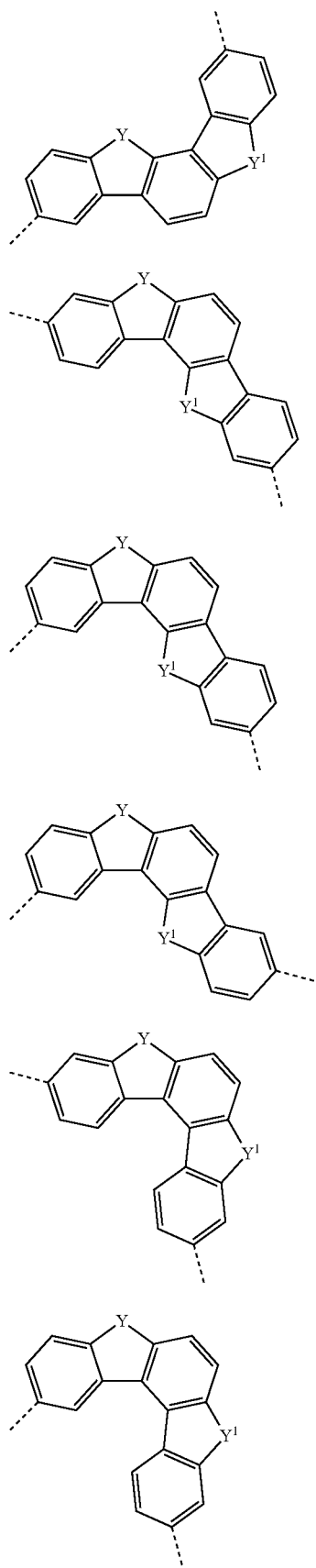
formula (15c)
formula (16a)
formula (16b)
formula (16c)
formula (17a)
formula (17b)
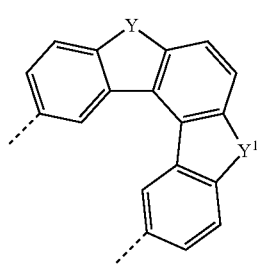
formula (17c)
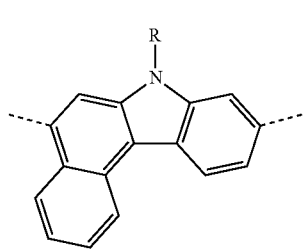
formula (18a)
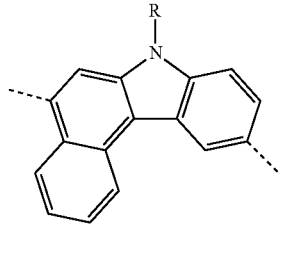
formula (18b)
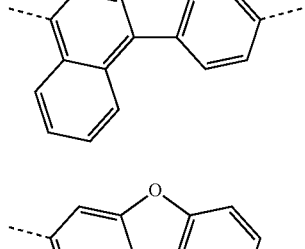
formula (20a)
formula (20b)
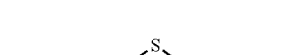
formula (22a)
formula (22b)

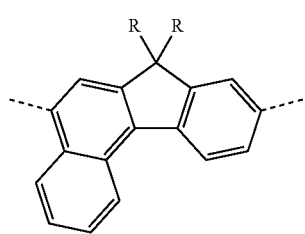
formula (24a)

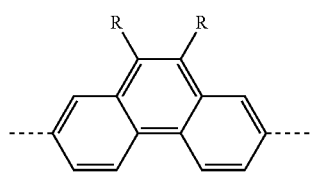
formula (26a)

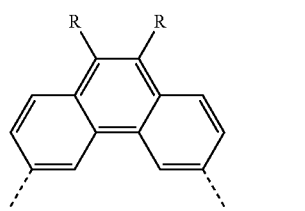
formula (26b)

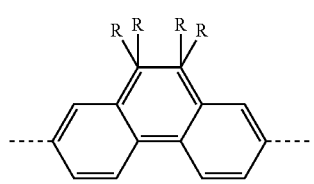
formula (27a)

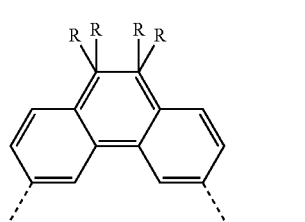
formula (27b)

where Y, $Y^1$ and R have the meanings given above, and the dashed bond indicates the position at which the structure is bonded to $Ar^2$ or $Ar^3$ or to the nitrogen or to $Ar^1$ for n>1. If the group mentioned above has two dashed bonds, the index m stands for 1, and if the group mentioned above has four dashed bonds, the index m stands for 3.

In a preferred embodiment of the invention, the index n=1, 2 or 3, particularly preferably 1 or 2.

If n=2 or 3, $Ar^1$ is preferably selected, identically or differently on each occurrence, preferably identically, from the structures of the above-mentioned formulae (8a) to (8d), (9a), (9b), (10a), (10b), (11a) to (11c), (18a), (18b), (19a), (19b), (24a) and (25a). The structures here are linked to one another at one of the positions denoted by a dashed bond.

If n=1, $Ar^1$ is preferably selected from the structures of the above-mentioned formulae (8c), (8d) and (11a) to (17c).

Particularly preferred units $Ar^1$ are those by means of which the conjugation between the nitrogen atoms in the compound of the formula (1) is interrupted or at least partially interrupted. A conjugation interruption of this type is obtained, for example, by an sp³-hybridised carbon atom, as in the units of the formula (11a). A partial interruption of the conjugation is also obtained if the linking of the unit of the formula (2) takes place in the para-positions to the group Y, as in the units of the formula (8a), (8e), (9a) and (10a), or if the linking of the unit of the formula (2) takes place via the group Y, as in the units of the formula (8c), (8d) or (8f).

Particularly preferred units $Ar^1$ are therefore the units of the formulae (8a), (8c), (8d), (8e), (8f), (9a), (10a), (11a) and (11c). Very particular preference is given to the units of the formulae (8a), (9a), (10a), (11a) and (11c), in particular the units of the formula (8a), (11a) and (11c).

In a further preferred embodiment of the present invention, the indices q and r are, identically or differently on each occurrence, 0 or 1, i.e. the group $Ar^1$ is either bonded directly to the nitrogen or is bonded to the nitrogen via a single aryl or heteroaryl group $Ar^2$ or $Ar^3$.

$Ar^2$ or $Ar^3$ for q or r not equal to 0 is preferably selected, identically or differently on each occurrence, preferably identically, from 1,2-phenylene, 1,3-phenylene or 1,4-phenylene, each of which may be unsubstituted or substituted by one or more radicals R. $Ar^2$ or $Ar^3$ for q or r not equal to 0 is particularly preferably 1,3-phenylene or 1,4-phenylene, which may be unsubstituted or substituted by one or more radicals R. If $Ar^2$ or $Ar^3$ is substituted by one or more radicals R, these radicals R are then preferably alkyl groups having 1 to 10 C atoms, particularly preferably having 1 to 4 C atoms.

In a further preferred embodiment of the present invention, $Ar^4$ to $Ar^7$ identically or differently on each occurrence, an aromatic or heteroaromatic ring system having 6 to 24 aromatic ring atoms, which contains not more than two aromatic or heteroaromatic six-membered rings which are condensed directly onto one another. $Ar^4$ to $Ar^7$ here may also be substituted by one or more radicals R, as described above, and two or more of the groups $Ar^4$ to $Ar^7$ may be bridged to one another or to $Ar^2$ or $Ar^3$ via E, as described above. $Ar^4$ to $Ar^7$ particularly preferably contains absolutely no aromatic or heteroaromatic six-membered rings which are condensed directly onto one another. $Ar^4$ to $Ar^7$ is very particularly preferably selected, identically or differently on each occurrence, from the group consisting of phenyl, ortho-, meta- or para-biphenyl, ortho-, meta- or para-terphenyl, linear or branched quaterphenyl, fluorenyl, spirobifluorenyl or carbazolyl, each of which may be substituted by one or more radicals R. At least one of the groups $Ar^4$ to $Ar^7$ is very particularly preferably selected from the group consisting of biphenyl or fluorenyl, each of which may also be substituted by one or more radicals R. If the group $Ar^4$ to $Ar^7$ contains a radical R, this radical R is preferably selected from an alkyl group having 1 to 10 C atoms, particularly preferably having 1 to 4 C atoms.

If two groups as indicated above are bridged by a group E, E preferably stands for a single bond or $CR_2$, i.e. a carbazole or a piperidine is preferably formed from the groups $Ar^4$ and $Ar^2$ or $Ar^4$ and $Ar^5$ or $Ar^6$ and $Ar^3$ or $Ar^6$ and $Ar^7$.

The compound of the formula (1) is, as described above, substituted by at least two groups of the formula (7). The compound of the formula (1) preferably contains between 2 and 8 groups of the formula (7), particularly preferably 2, 3 or 4 groups of the formula (7), very particularly preferably precisely 2 groups of the formula (7). The groups of the formula (7) are crosslinkable units Q, which are either linked directly or via a spacer group L and/or an aromatic unit $Ar^8$.

In an embodiment of the present invention, the group L is a single bond.

In a further embodiment of the present invention, the group L is a so-called spacer group, also referred to as spacer. The spacer group L employed can be all groups which are known to the person skilled in the art for this purpose. The group L here on the one hand does the job of decoupling the crosslinkable group Q electronically from the remainder of the molecule. Furthermore, the group L introduces flexibility into the compound according to the invention, which supports the performance of the crosslinking reaction.

If L is a spacer group, L is preferably a linear or branched alkylene group having 1 to 20 C atoms, particularly preferably having 1 to 12 C atoms, in which one or more non-adjacent $CH_2$ groups may be replaced by —O—, —S—, —NH—, —N($CH_3$)—, —N—CO—, —N—CO—O—, —N—CO—N, —CO—, —O—CO—, —S—CO—, —O—COO—, —CO—S—, —CO—O—, —CH(halogen)-, —CH(CN)—, —CH=CH— or —C≡C—, or a cyclic alkyl group, preferably cyclohexane or a cyclohexane derivative having 1,4- or 1,3-linking. Further possible spacer groups L are, for example, —($CH_2$)$_s$—, —($CH_2CH_2O$)$_t$—$CH_2CH_2$—, —$CH_2CH_2$—S—$CH_2CH_2$— or —$CH_2CH_2$—NH—$CH_2CH_2$—, where s=2 to 12 and t=1 to 3, but also —O—.

It is preferred for L to denote a single bond or an alkylene or alkyleneoxy group having 2 to 8 C atoms. Straight-chain groups are particularly preferred here.

Particularly preferred groups L are a single bond, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene or butenylene.

$Ar^8$ for p not equal to 0 is preferably selected from 1,2-phenylene, 1,3-phenylene or 1,4-phenylene, each of which may be unsubstituted or substituted by one or more radicals R. $Ar^8$ is particularly preferably 1,4-phenylene, which may be unsubstituted substituted by one or more radicals R. If $Ar^8$ is substituted by one or more radicals R, these radicals are then preferably alkyl groups having 1 to 10 C atoms, particularly preferably having 1 to 4 C atoms.

As described above, the crosslinkable group Q is a functional group which is capable of undergoing a chemical reaction and thus forming an insoluble compound. The chemical reaction here is a polymerisation reaction. It is generally possible to employ all groups Q which are known to the person skilled in the art for this purpose. The job of this group is, in particular, to link the compounds according to the invention to one another, optionally to further reactive compounds, by a crosslinking reaction. This results in a crosslinked compound, or, if the reaction is carried out in a layer, in a crosslinked layer. A crosslinked layer in the sense of the present invention is taken to mean a layer which is obtainable by carrying out the crosslinking reaction from a layer of the compound according to the invention. The crosslinking reaction is a polymerisation reaction in the classical sense, i.e. a chain reaction in which a crosslinked polymer is formed. The crosslinking reaction can generally be initiated by heat and/or by UV, microwave, X-ray or electron radiation and/or by the use of free-radical formers, anions, cations, acids and/or photoacids. The presence of catalysts may likewise be appropriate or necessary. The crosslinking reaction is preferably a reaction for which no initiator and no catalyst has to be added.

Crosslinkable groups Q which are preferred in accordance with the invention are the units described below.

a) Terminal or Cyclic Alkenyl or Terminal Alkynyl Groups:

Suitable units are those which contain a terminal or cyclic double bond or a terminal triple bond, in particular terminal or cyclic alkenyl or terminal alkynyl groups having 2 to 40 C atoms, preferably having 2 to 10 C atoms, where individual $CH_2$ groups and/or individual H atoms may also be replaced by the groups mentioned above in the case of R. Individual $CH_2$ groups in the terminal alkenyl or alkynyl groups may also be replaced by the groups mentioned above in the case of R. Furthermore, also suitable are groups which are to be considered as precursors and which are capable of the in-situ formation of a double or triple bond.

Preferred crosslinkable groups Q include vinyl, propenyl, butenyl, $C_{4-20}$-cycloalkenyl and ethynyl. Thus, for example, the groups indicated below are suitable, where the link to $Ar^8$ or to L or to one of the groups $Ar^4$ to $Ar^7$ in these groups is inn each case indicated by the dashed bond, and these groups may each be substituted by one or more radicals R, but are preferably unsubstituted:

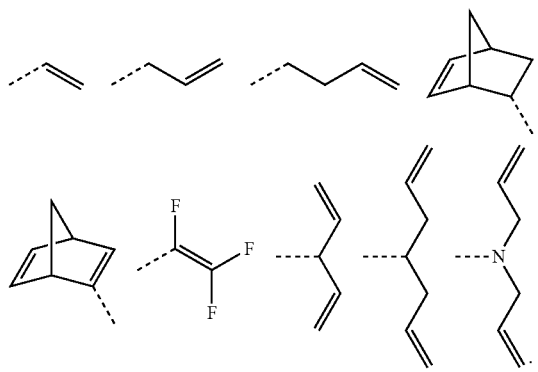

Also suitable are arylvinyl groups in the broadest sense. An arylvinyl group in the sense of the present application is taken to mean an aryl or heteroaryl group which is substituted by a vinyl group and which may also carry one or more further radicals R. Thus, for example, the groups indicated below are suitable, where the link to $Ar^8$ or to L or to one of the groups $Ar^4$ to $Ar^7$ in these groups is in each case indicated by the dashed bond, and these groups may each be substituted by one or more radicals R, but are preferably unsubstituted:

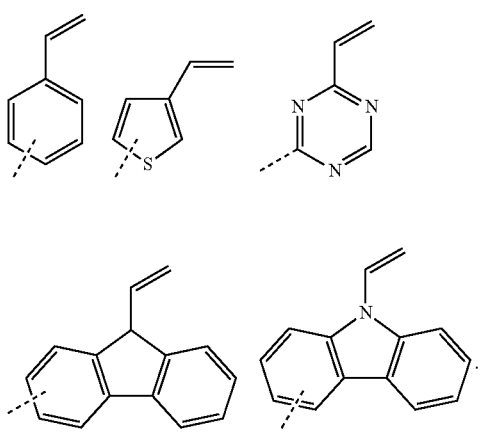
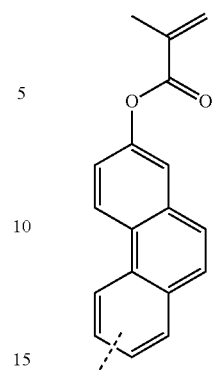

A styryl group, i.e. the first group indicated, is particularly preferred here.

Also suitable are acrylic acid derivatives in the broadest sense, in particular acrylates, acrylamides, methacrylates and methacrylamides. Particular preference is given to $C_{1-10}$-alkyl acrylate and $C_{1-10}$-alkyl methacrylate. Thus, for example, the groups indicated below are suitable, where the link to $Ar^8$ or to L or to one of the groups $Ar^4$ to $Ar^7$ in these groups is in each case indicated by the dashed bond, and these groups may each be substituted by one or more radicals R, but are preferably unsubstituted:

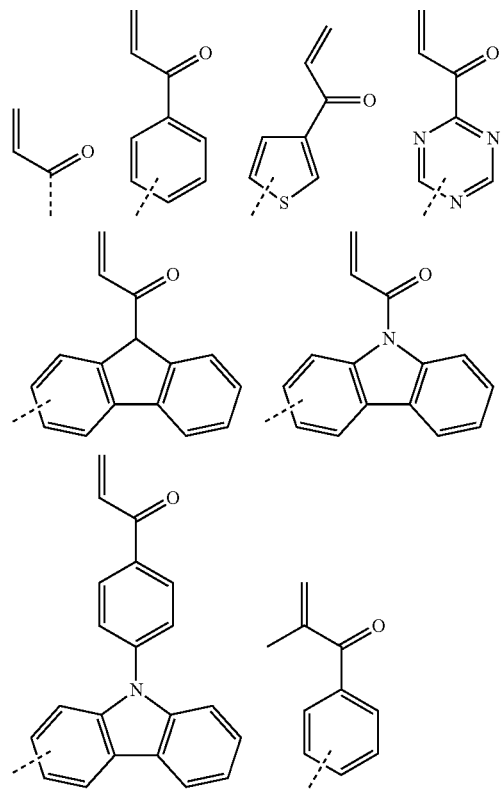

Also suitable are alkenyloxy or perfluoroalkenyloxy derivatives, in particular ethenyleneoxy or perfluoroethenyleneoxy. Thus, for example, the groups indicated below are suitable, where the link to $Ar^8$ or to L or to one of the groups $Ar^4$ to $Ar^7$ in these groups is in each case indicated by the dashed bond, and these groups may each be substituted by one or more radicals R, but are preferably unsubstituted:

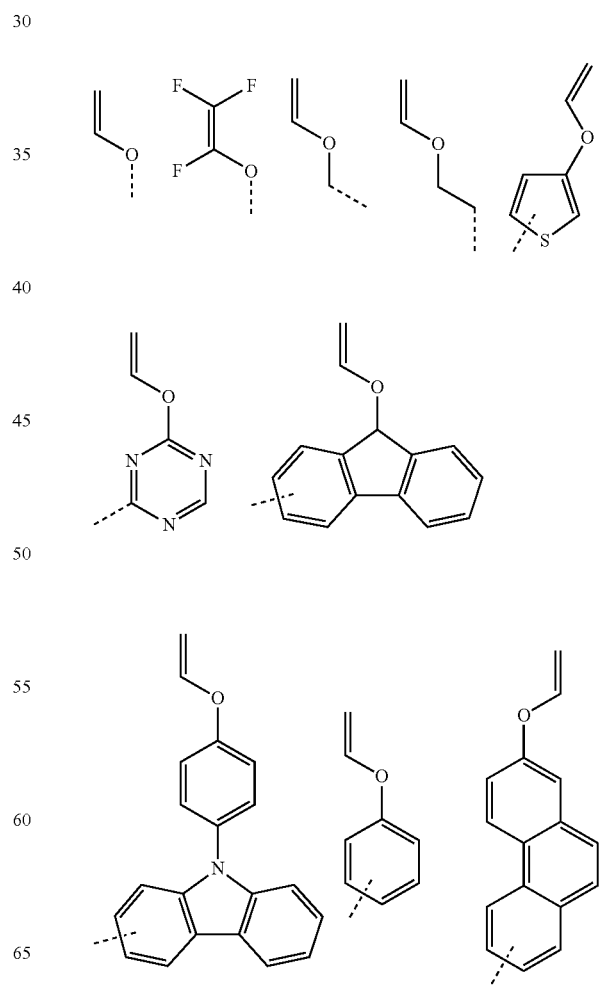

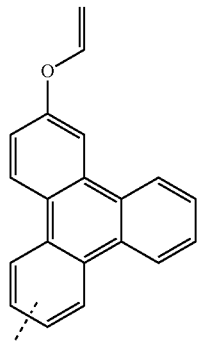

The polymerisation reaction of the above-mentioned alkenyl or alkynyl groups can take place via a free-radical, cationic or anionic mechanism. It may be appropriate to add a corresponding initiator for the polymerisation reaction. Suitable initiators for free-radical polymerisation are, for example, dibenzoyl peroxide, AIBN or TEMPO. Suitable initiators for cationic polymerisation are, for example, AlCl$_3$, BF$_3$, triphenylmethyl perchlorate, tropylium hexachloroantimonate, etc. Suitable initiators for anionic polymerisation are bases, in particular butyllithium.

In a preferred embodiment of the present invention, however, the polymerisation is carried out without the addition of an initiator and is initiated exclusively thermally. This preference is due to the fact that the absence of the initiator prevents contamination of the layer, which could result in impairment of the device properties.

b) Ring-Opening Polymerisation Based on Oxetanes and Oxiranes

A further suitable class of crosslinkable groups Q are oxetanes and oxiranes, which polymerise cationically by ring opening. Thus, for example, the groups indicated below are suitable, where the link to Ar$^8$ or to L or to one of the groups Ar$^4$ to Ar$^7$ in these groups is in each case indicated by the dashed bond, and these groups may each be substituted by one or more radicals R, but are preferably unsubstituted; R' stands for a methyl or ethyl group:

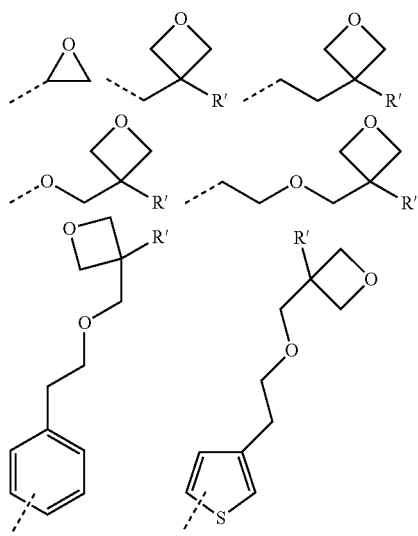

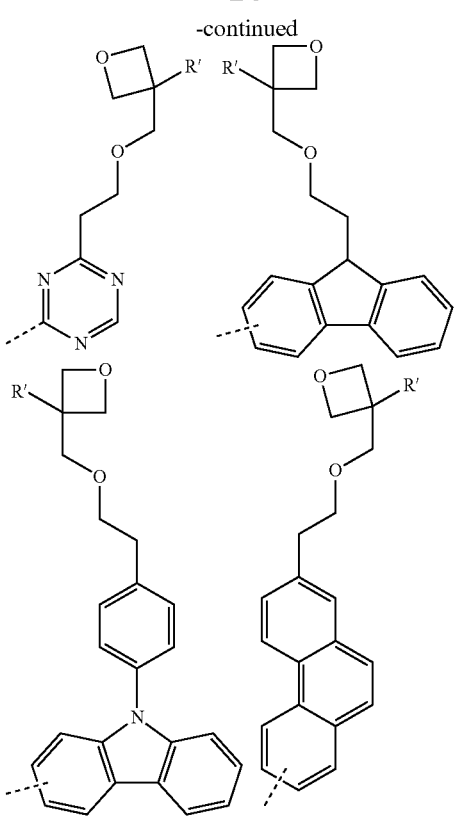

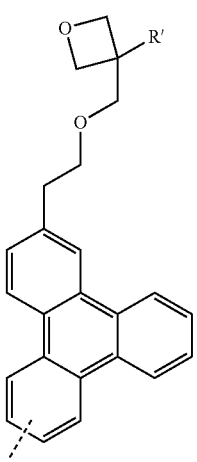

It may be appropriate to add a corresponding initiator for the polymerisation reaction. Suitable initiators are, for example, AlCl$_3$, BF$_3$, triphenylmethyl perchlorate, tropylium hexachloroantimonate, etc. It is likewise possible to add photoacids as initiators.

c) Silanes

Also suitable as a class of crosslinkable groups are silane groups SiR$_3$, where at least two groups R, preferably all three groups R, stands for Cl or an alkoxy group having 1 to 20 C atoms. This group reacts in the presence of water to give an oligo- or polysiloxane.

The above-mentioned crosslinkable groups Q are generally known to the person skilled in the art in the area of polymer chemistry, as are the suitable reaction conditions used for the reaction of these groups.

In a preferred embodiment, the crosslinkable groups Q are selected from terminal or cyclic alkenyl or terminal alkynyl groups, as indicated above under a), in particular from terminal alkenyl groups and arylvinyl groups. These have the advantage that they react thermally under comparatively mild conditions and can thus be crosslinked. A particularly preferred alkenyl group is the vinyl group. Particularly preferred arylvinyl groups are styryl groups, where the vinyl group can be bonded to the phenyl group in the ortho-, meta- or para-position, but is preferably bonded in the para-position.

The above-mentioned embodiments can be combined with one another as desired. The embodiments mentioned as preferred above particularly preferably occur simultaneously.

Suitable and preferred compounds according to the invention are the compounds depicted in the following table.

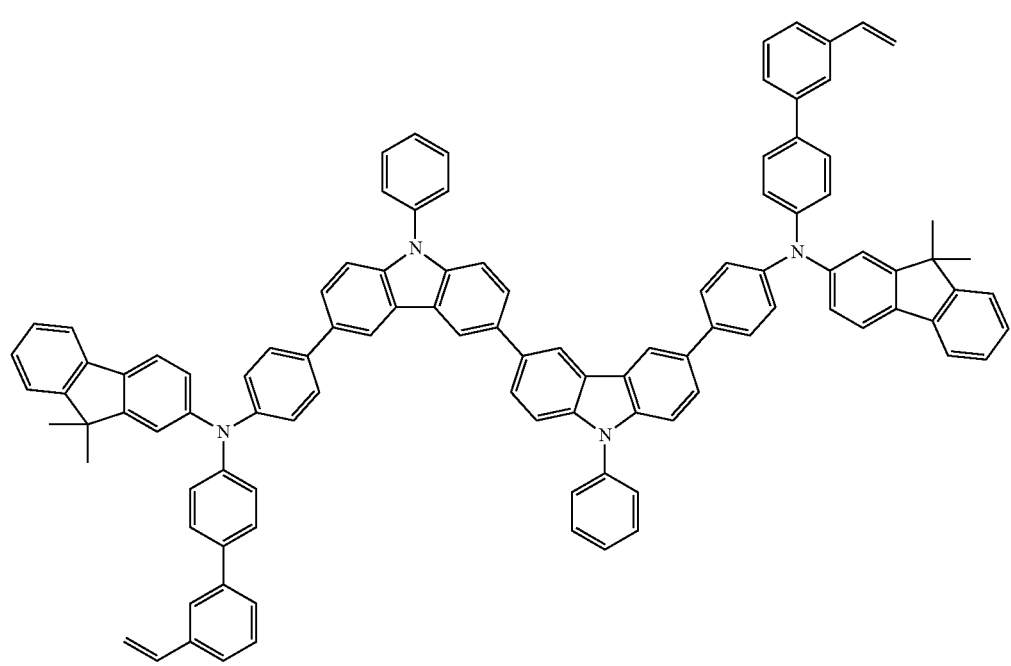

(1)

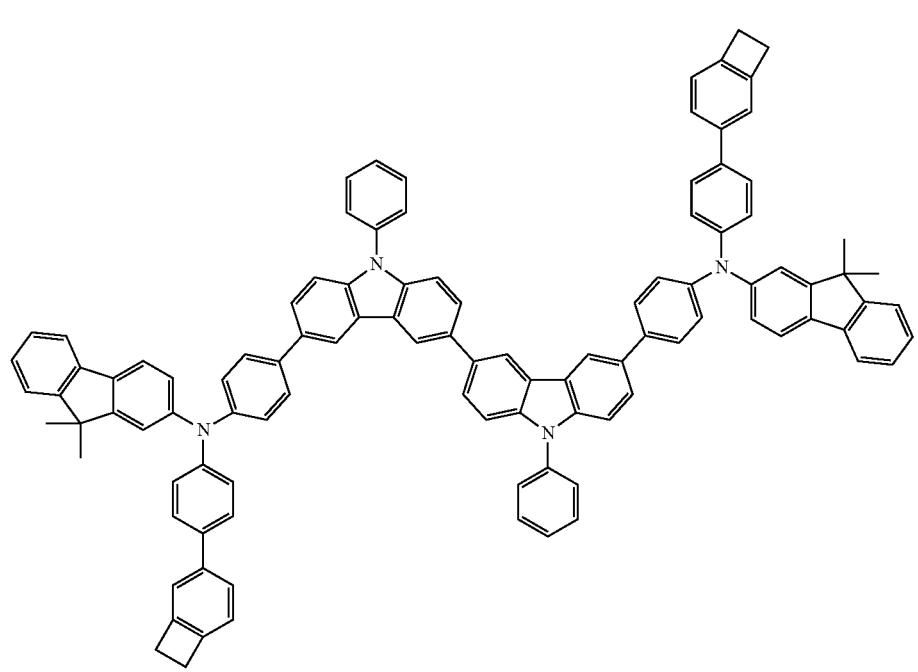

(2)

-continued
(3)
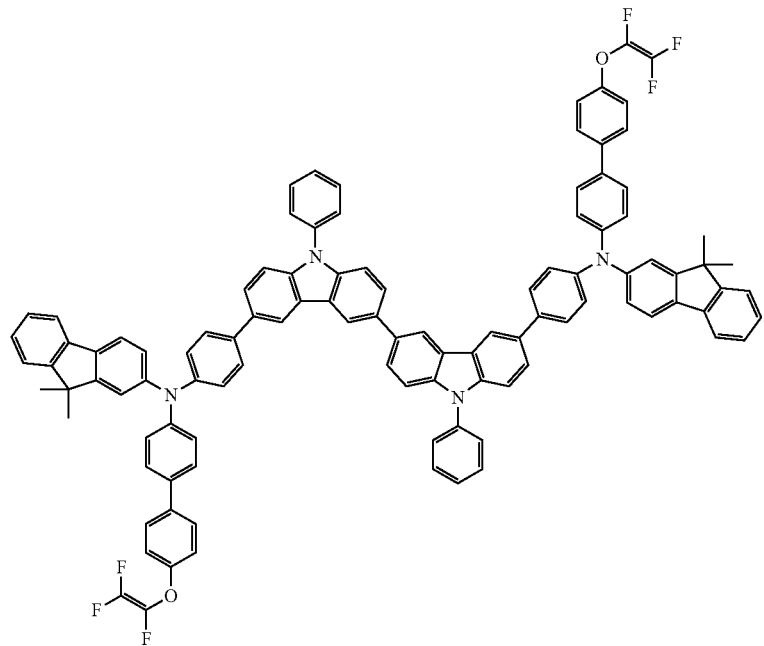
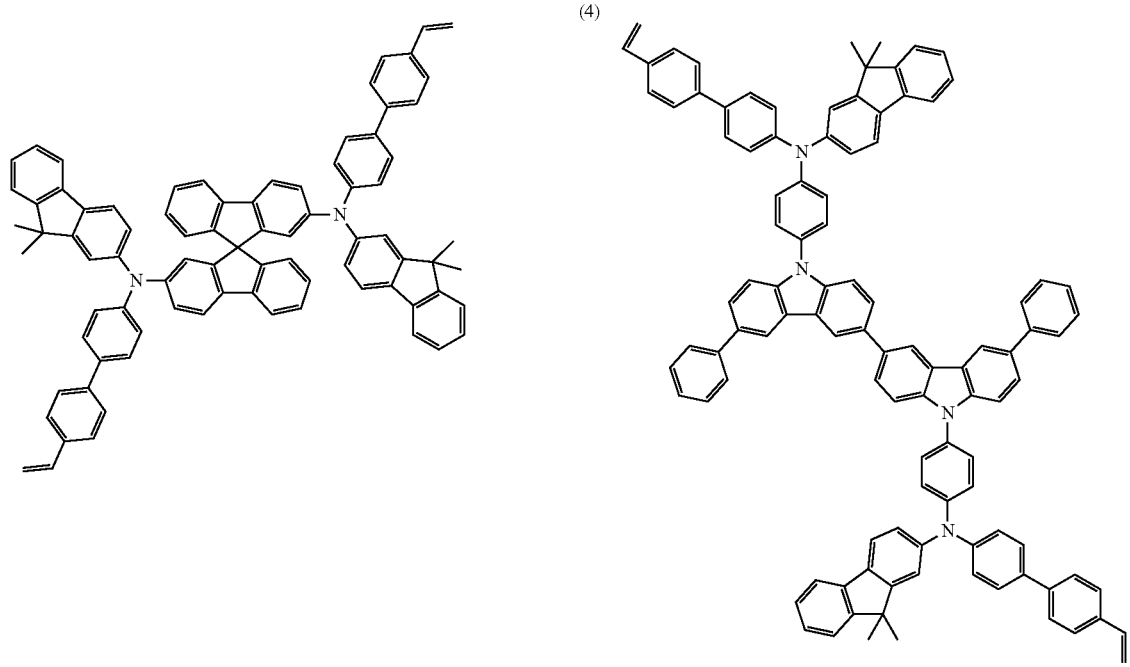

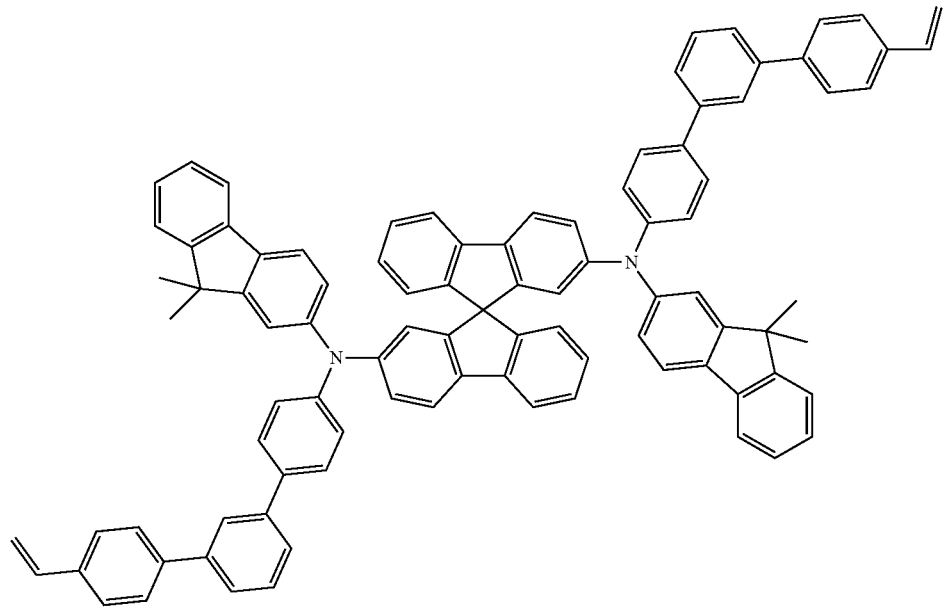
(6)
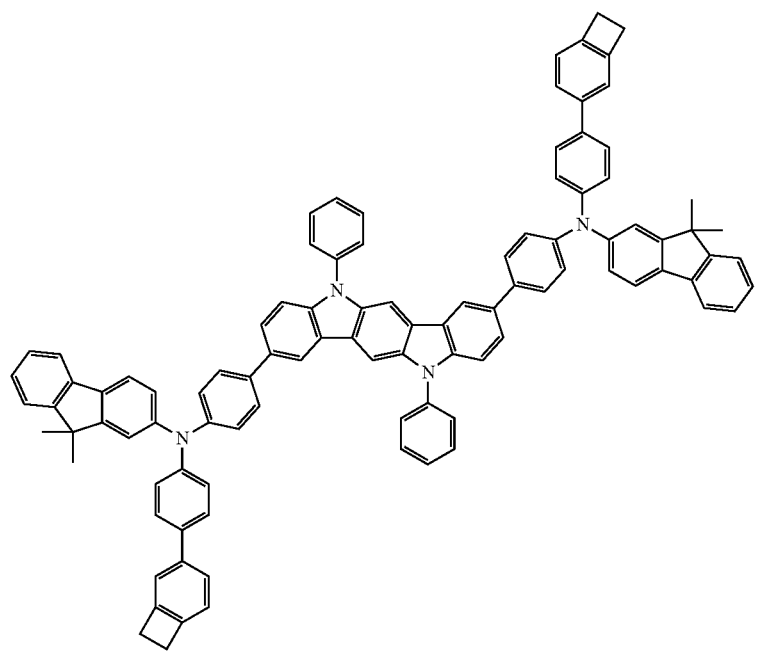
(7)

(8)
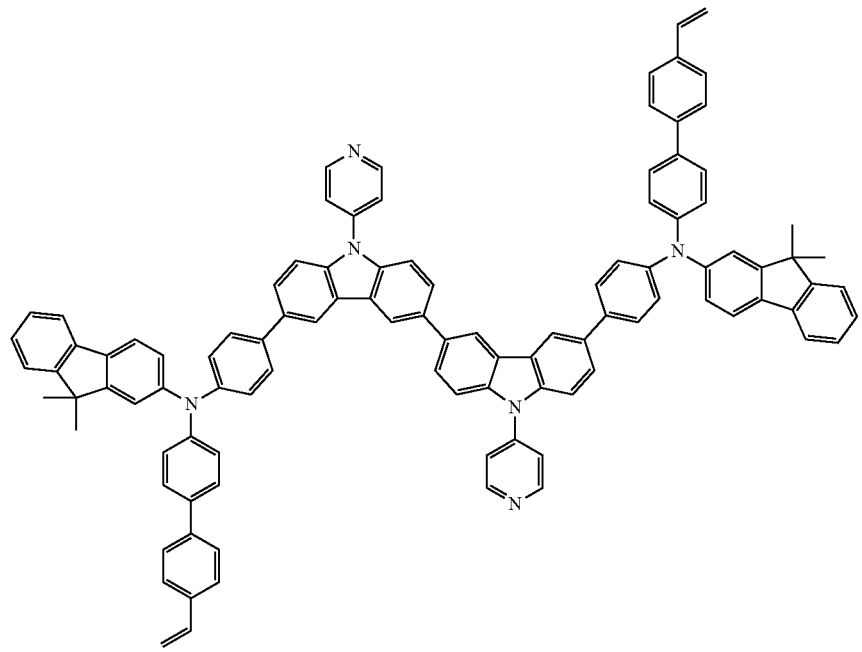
(9)
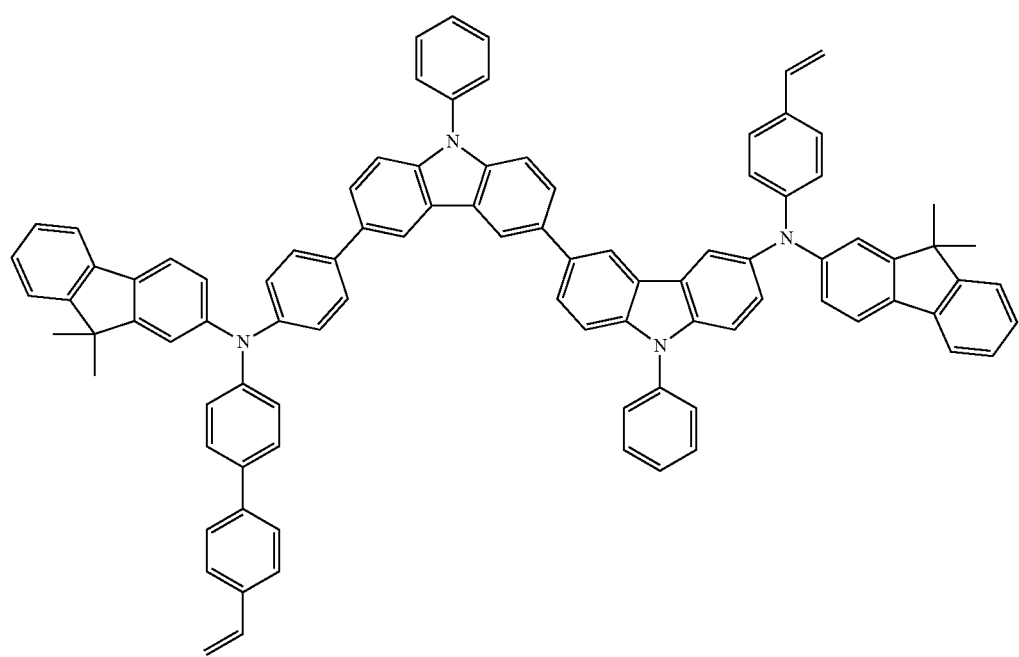

(10)
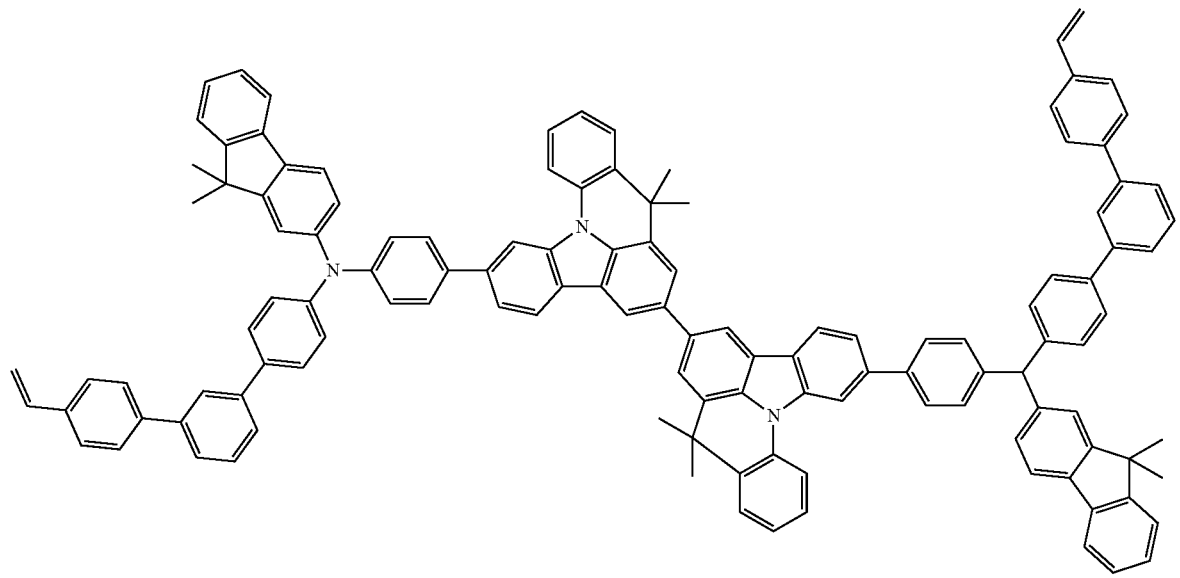
(11)
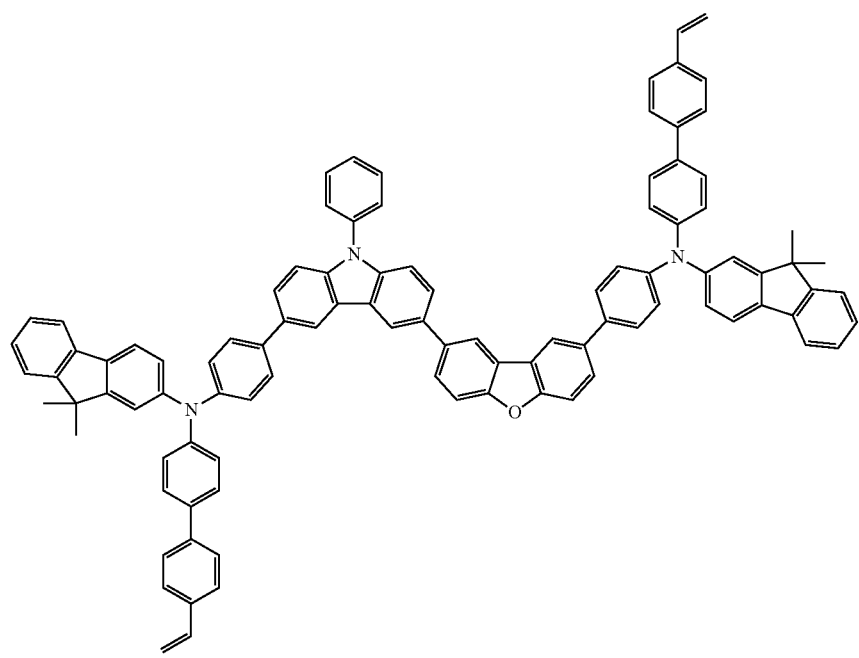

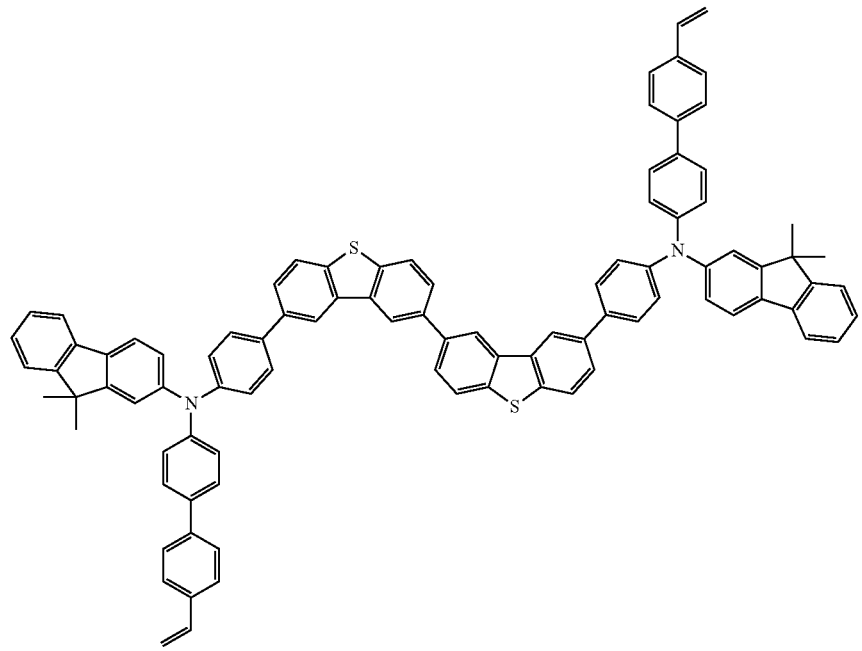
(12)
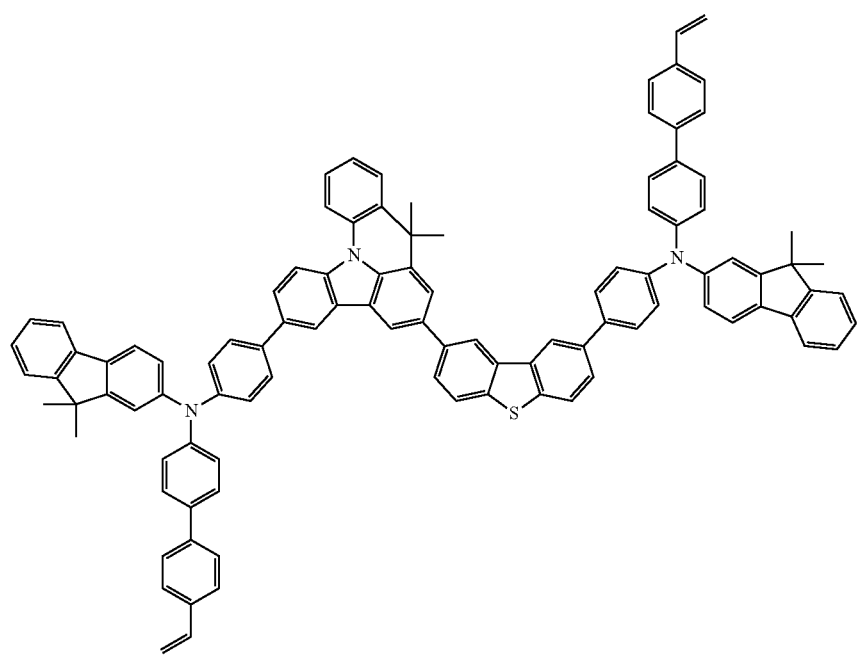
(13)

(14)
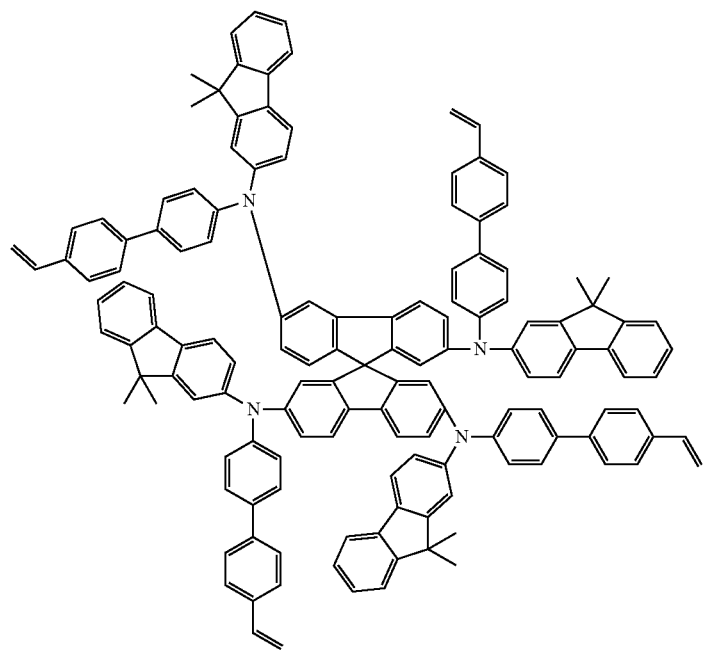
(15)
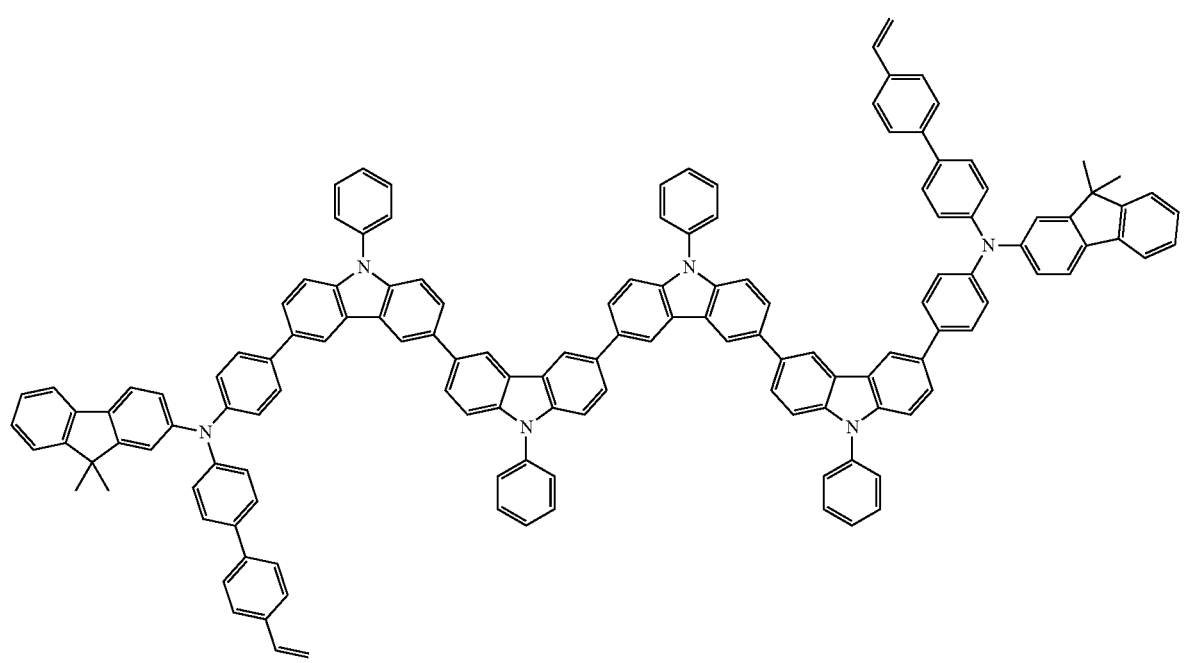

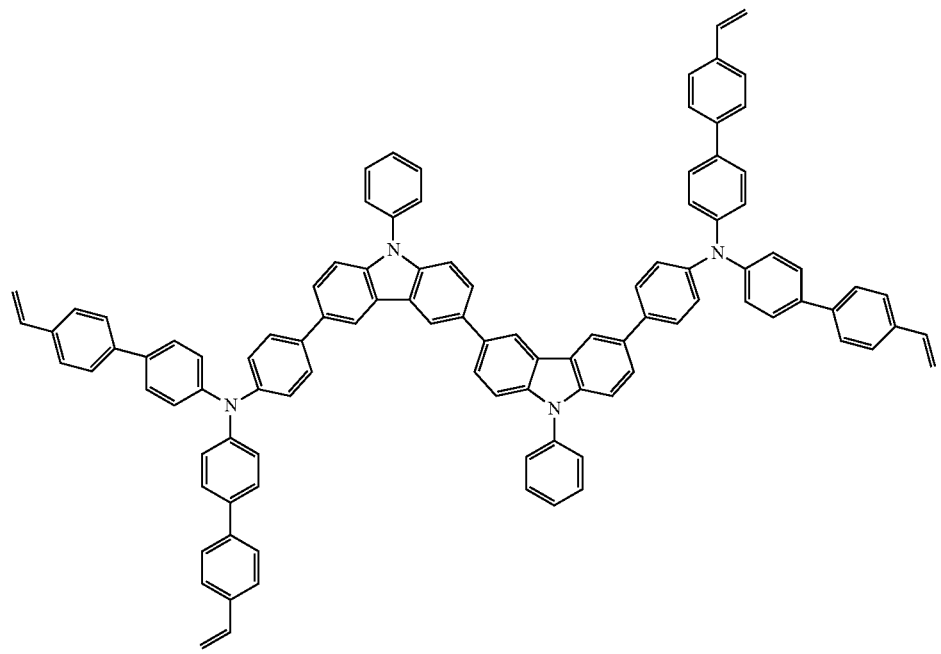
(16)
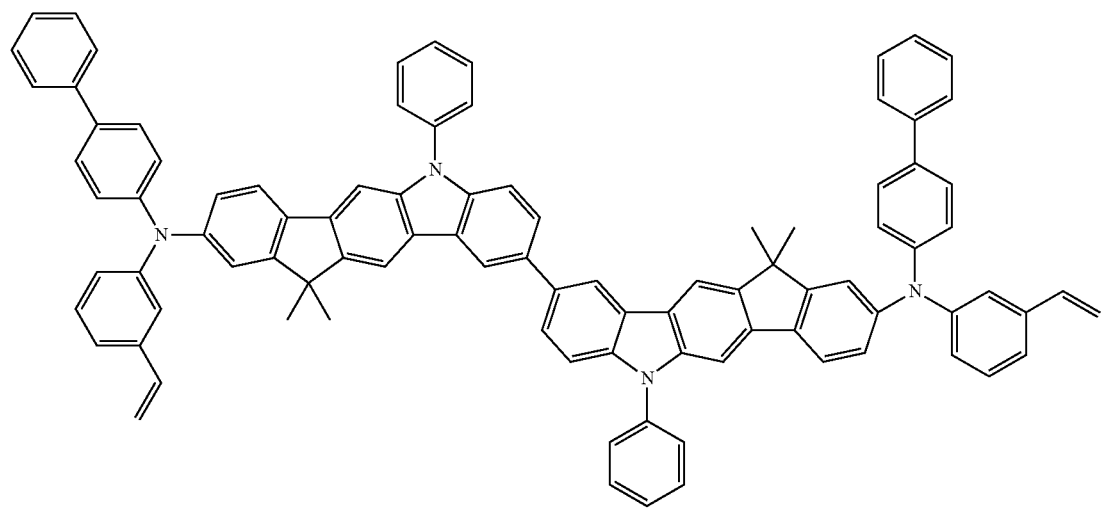
(17)

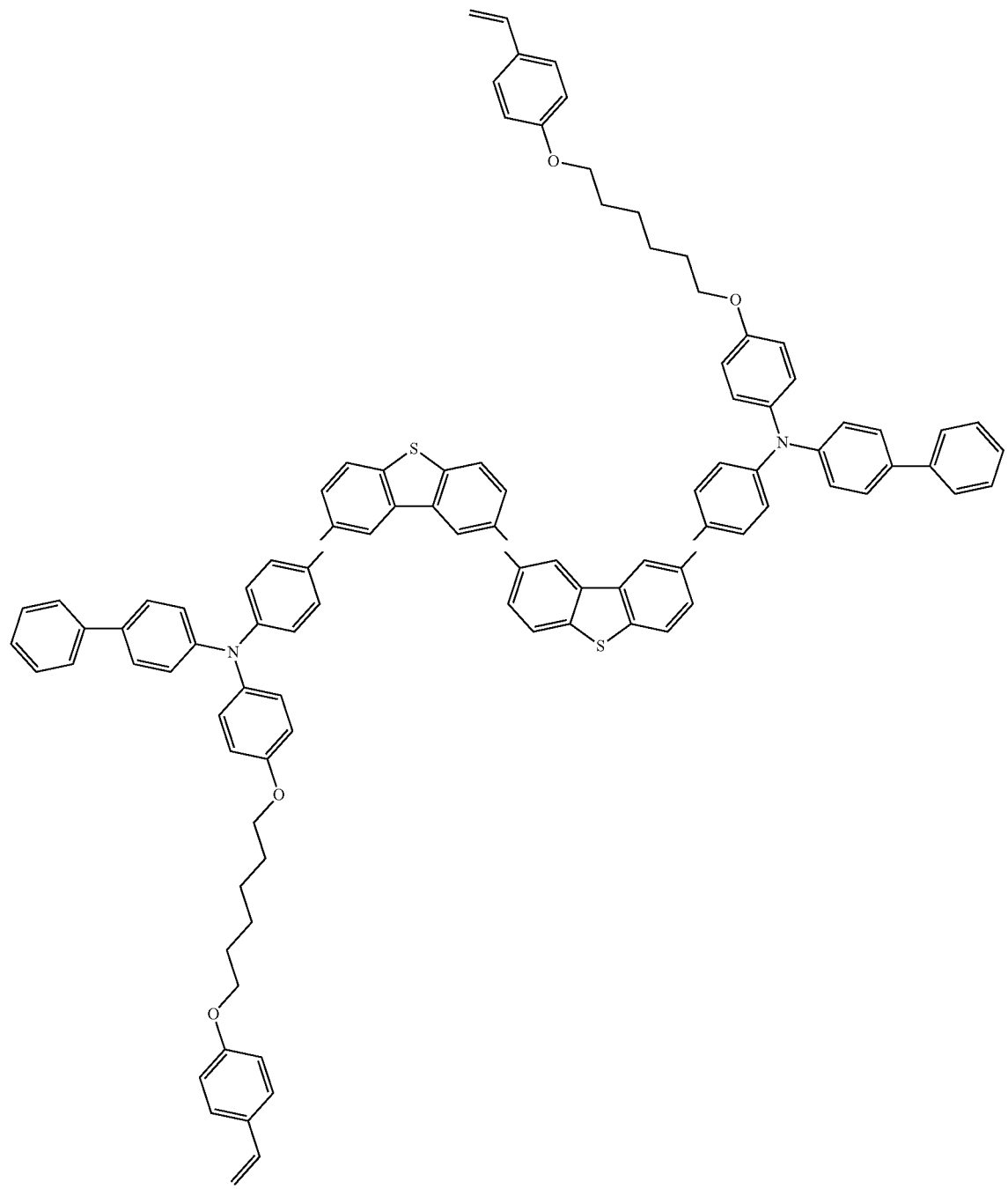
(18)

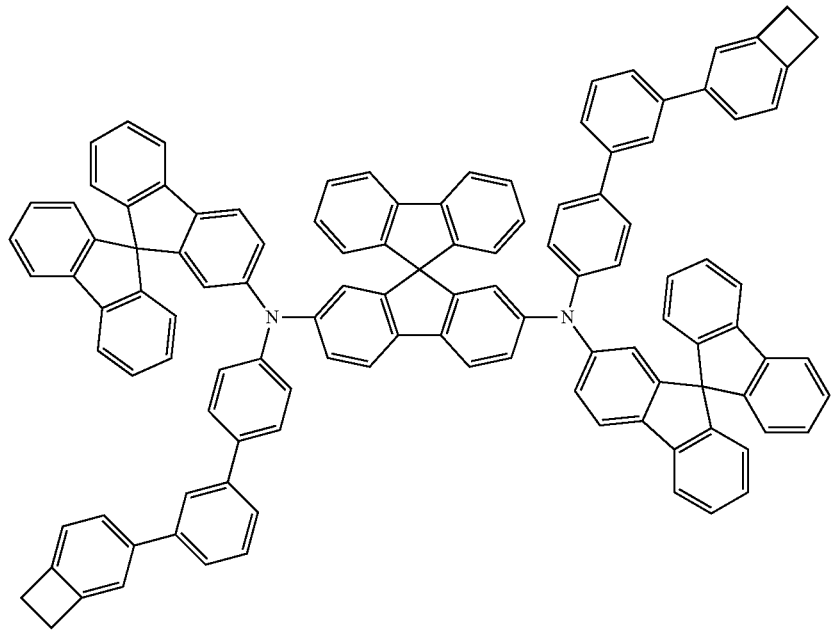
(19)
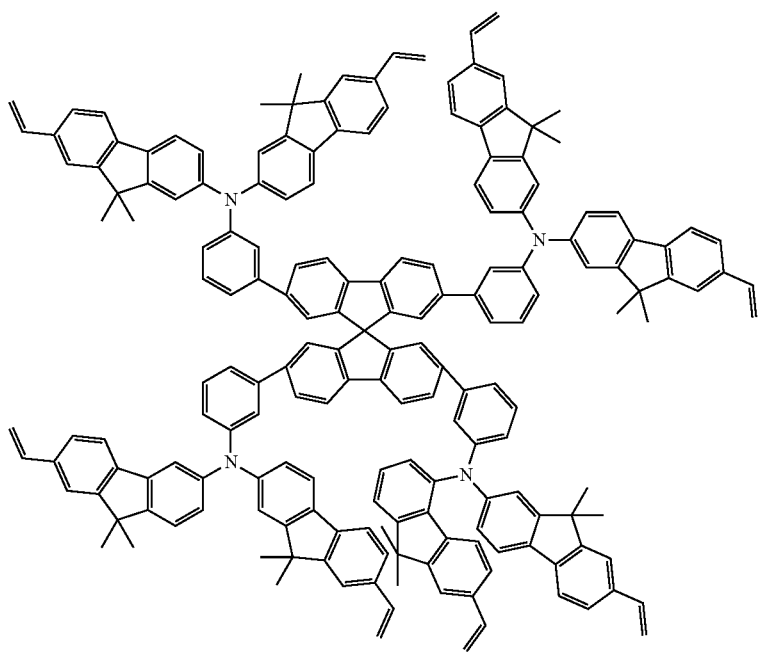
(20)

(21)
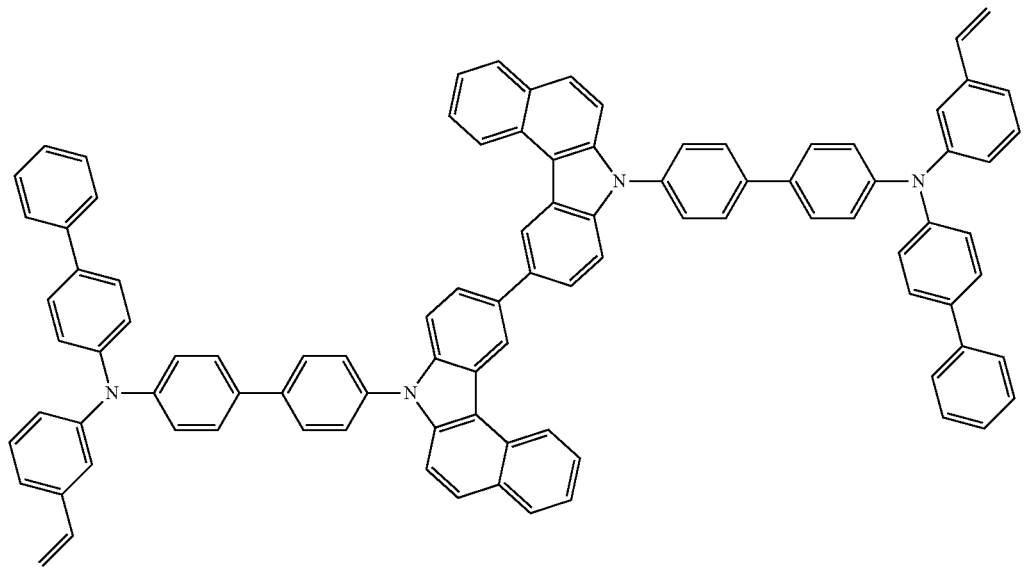
(22)
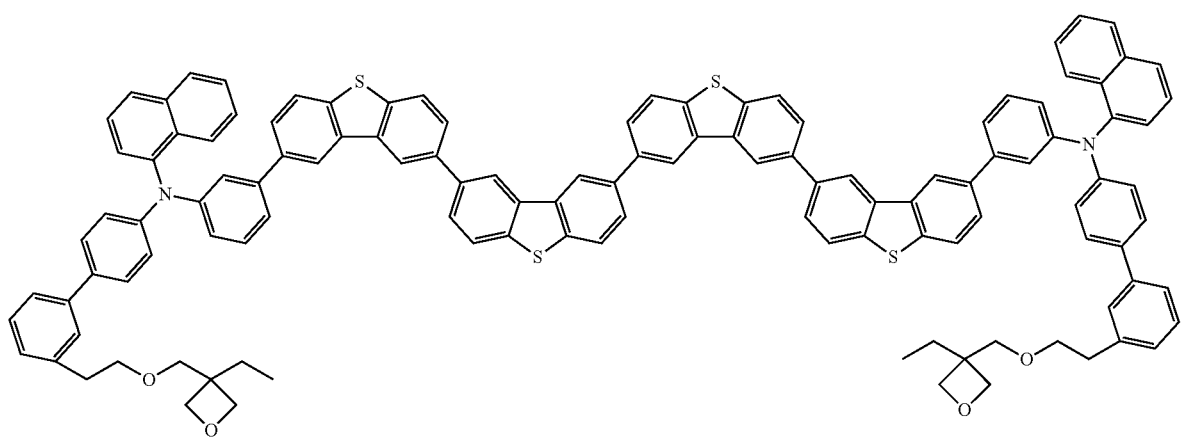
(23)
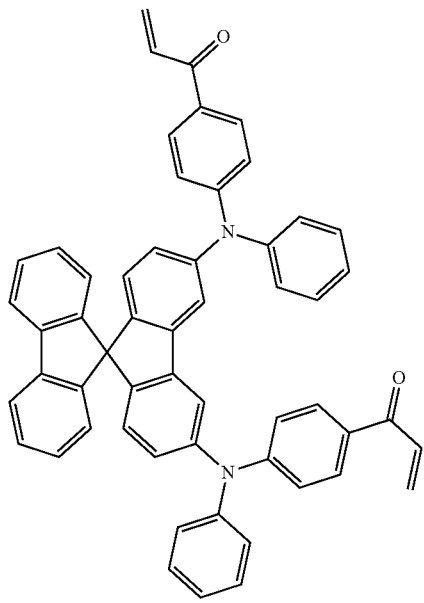

(24)
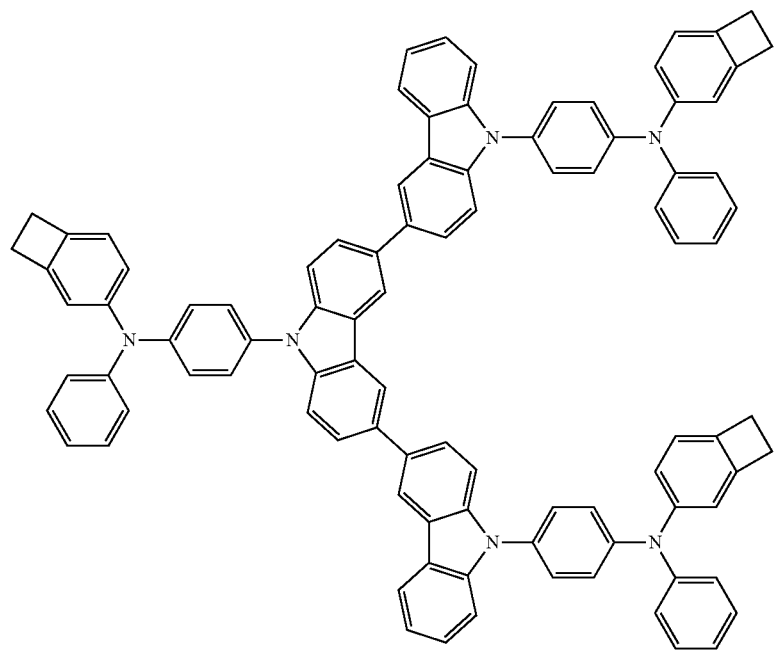
(25)
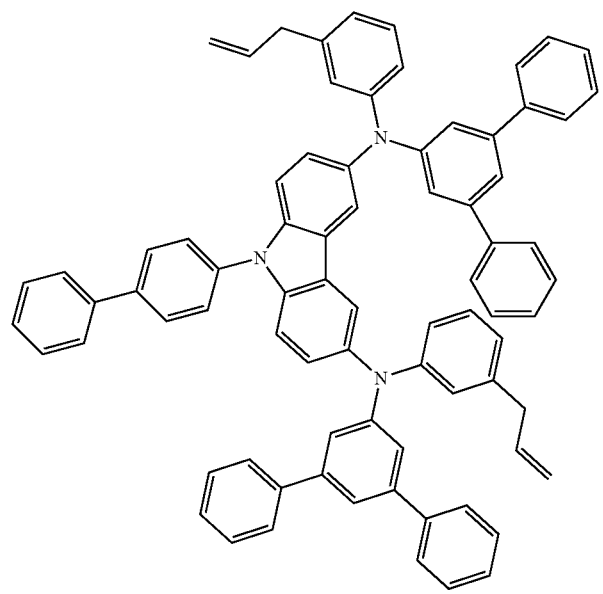

(26)
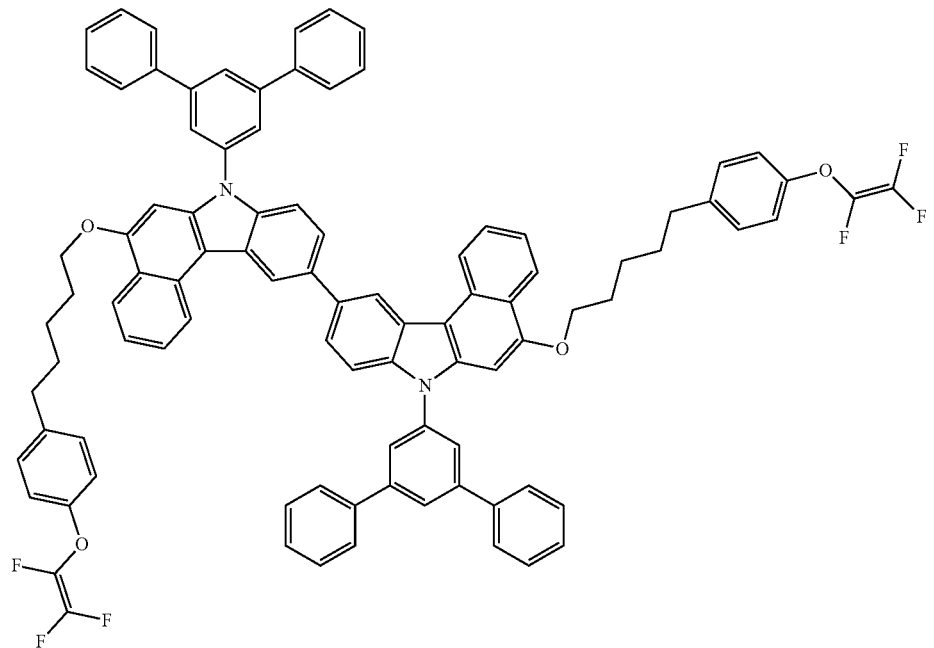
(27)
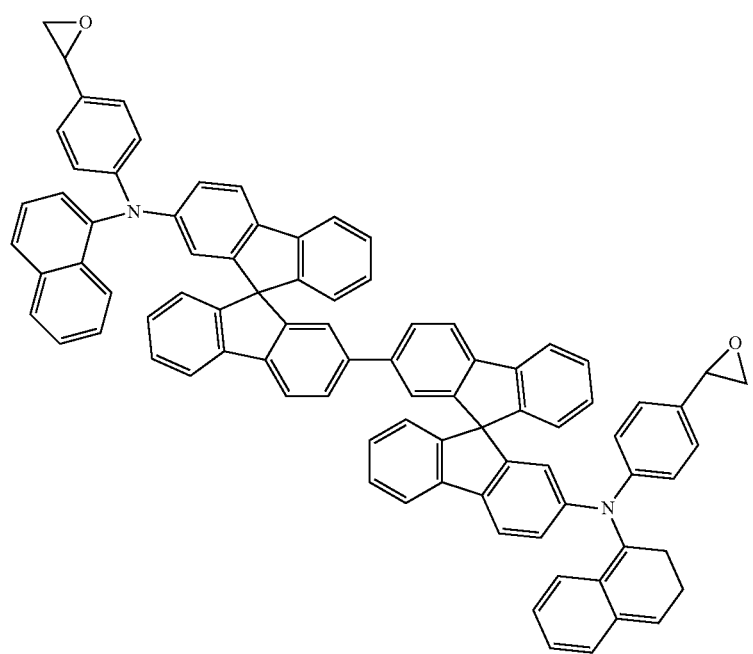

(28)
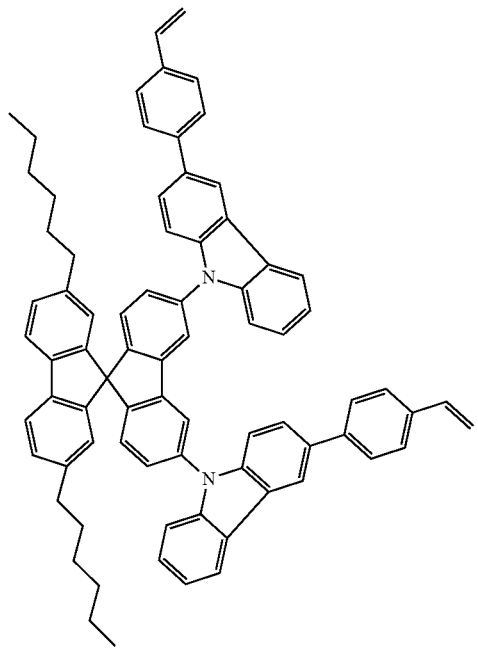
(29)
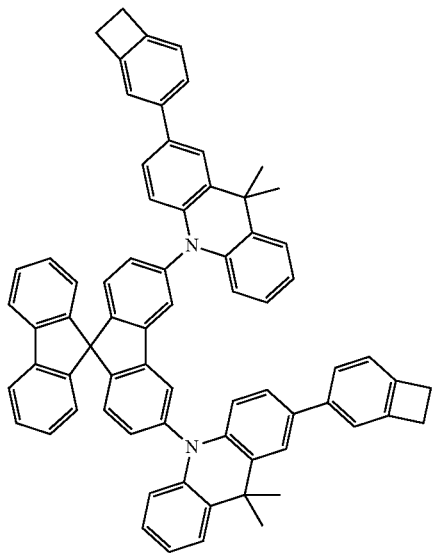
(30)
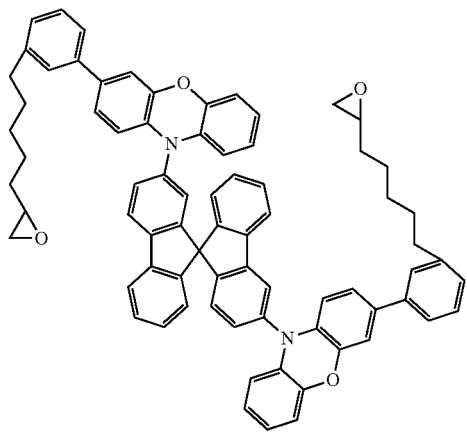
(31)
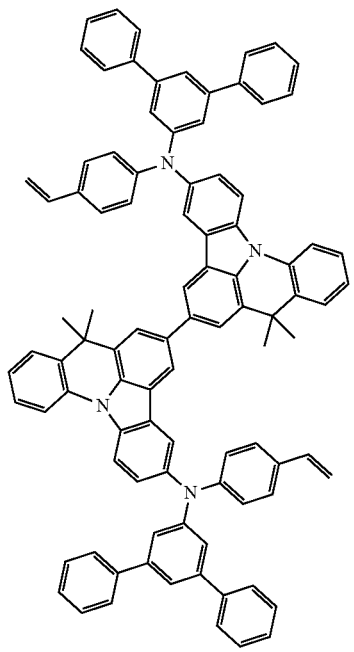

(32)
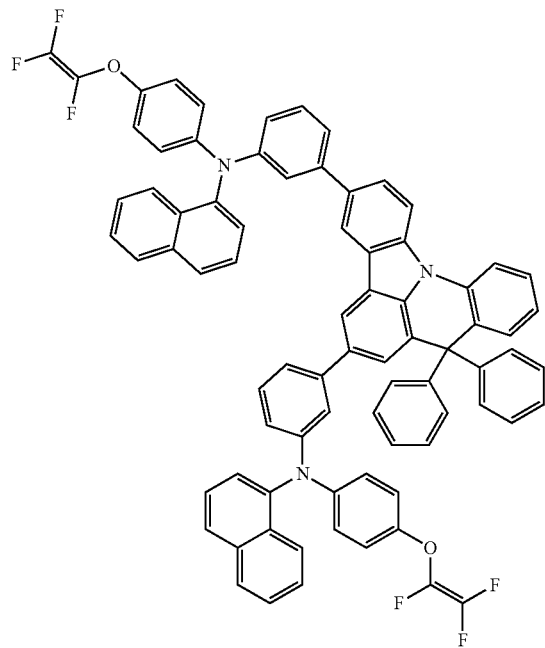
(33)
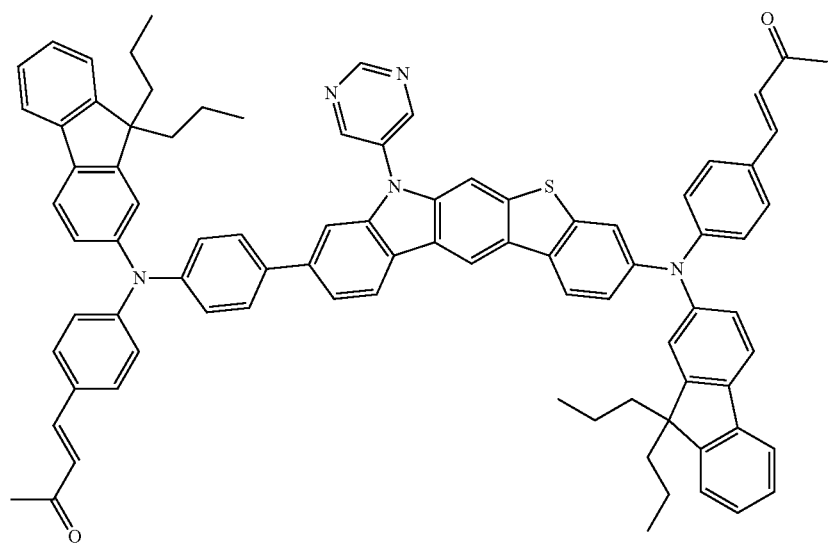

(34)
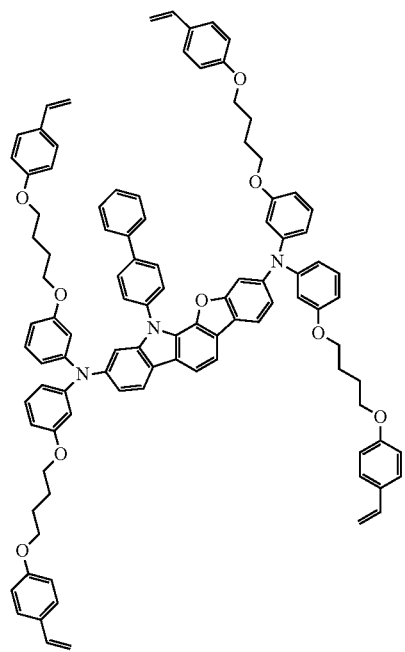
(35)
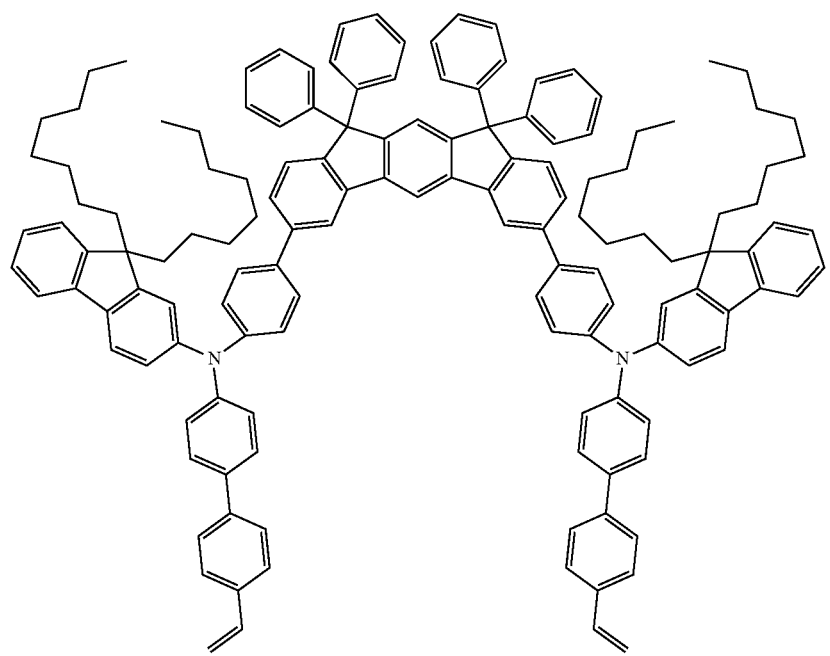

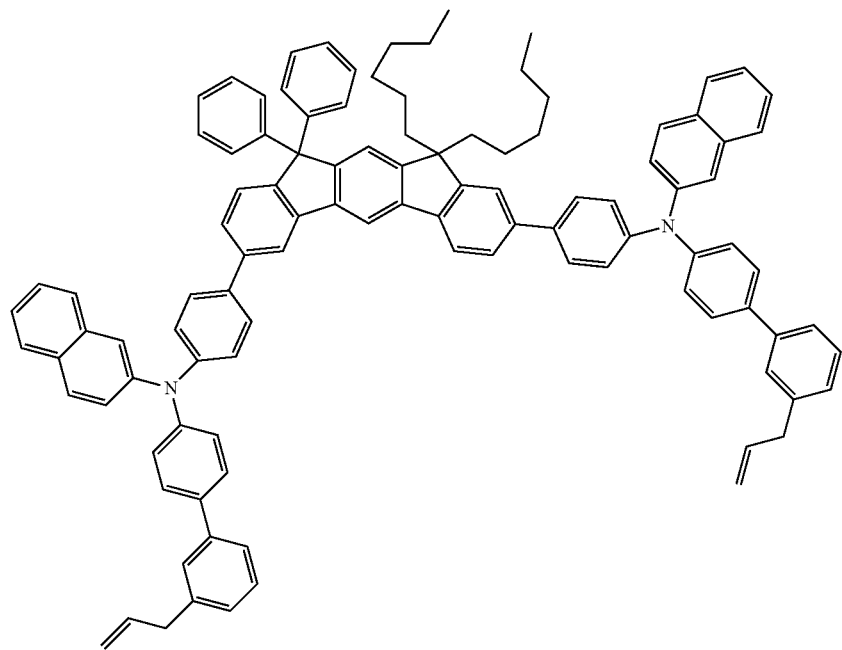
(36)
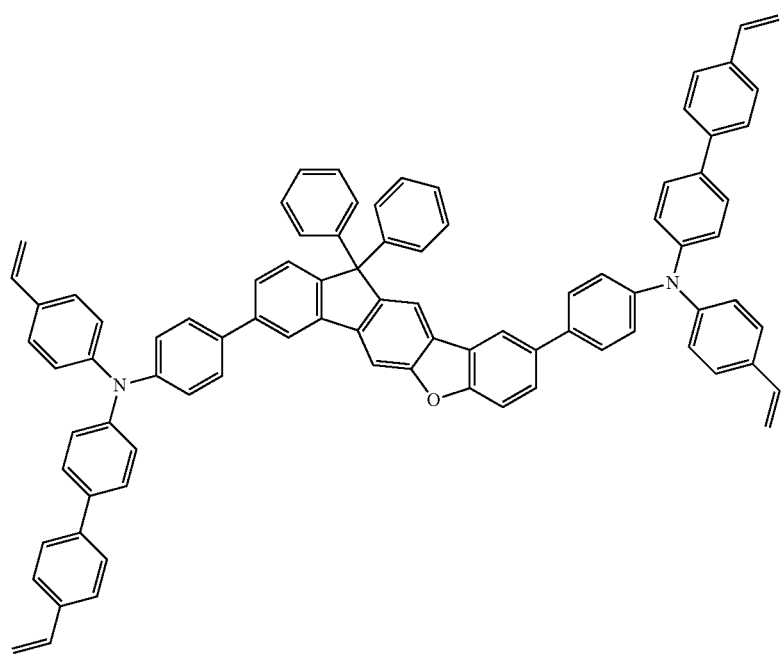
(37)

-continued
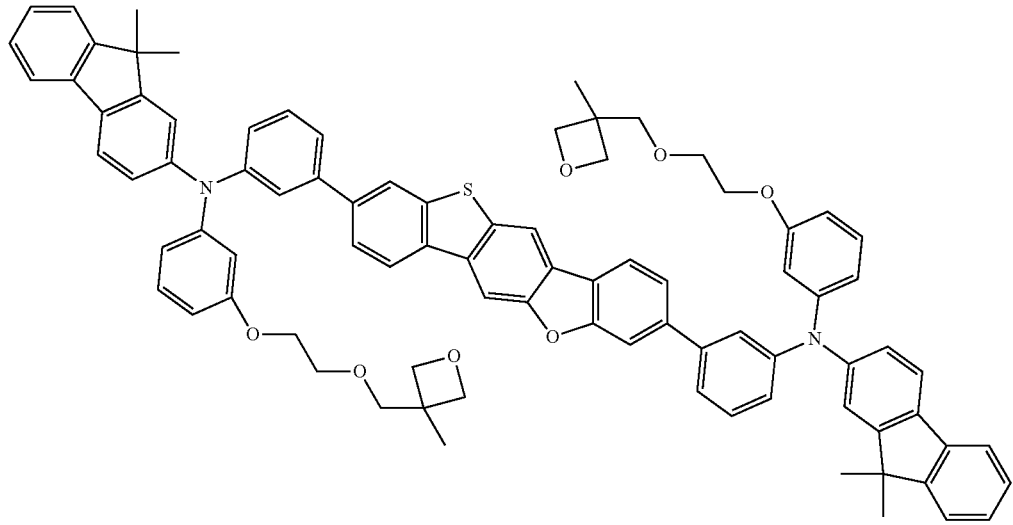
(38)
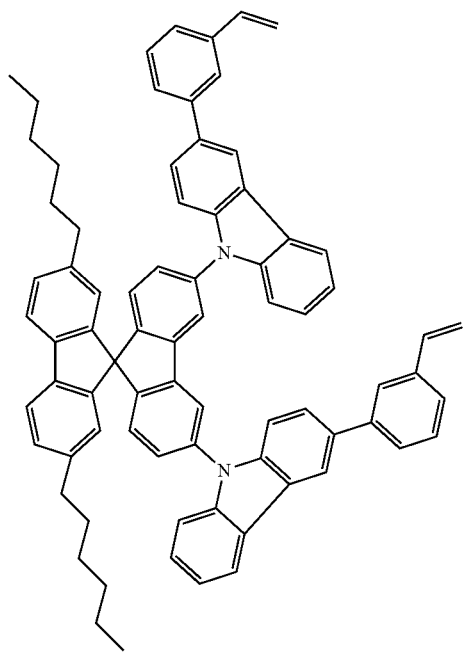
(39)

(40)
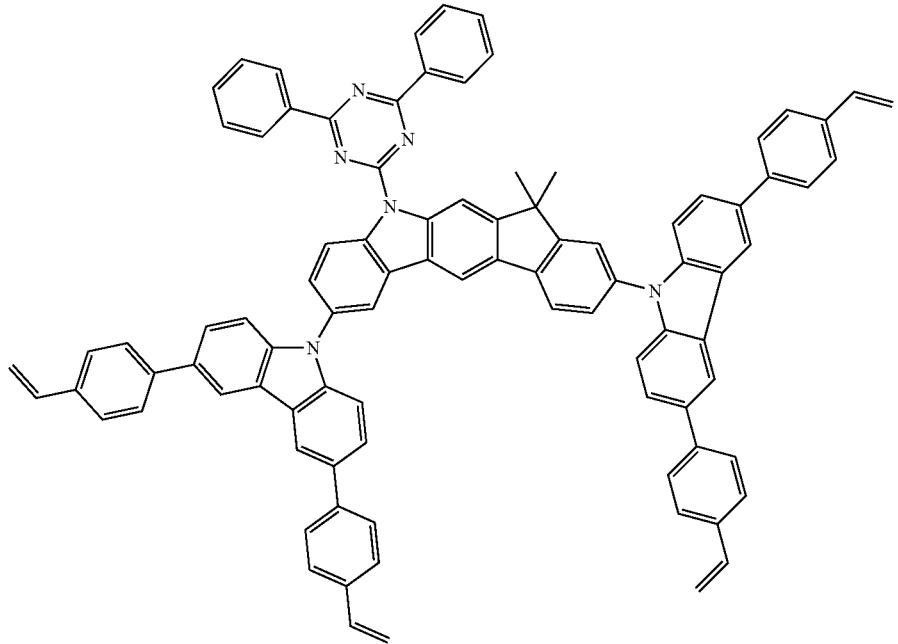
(41)
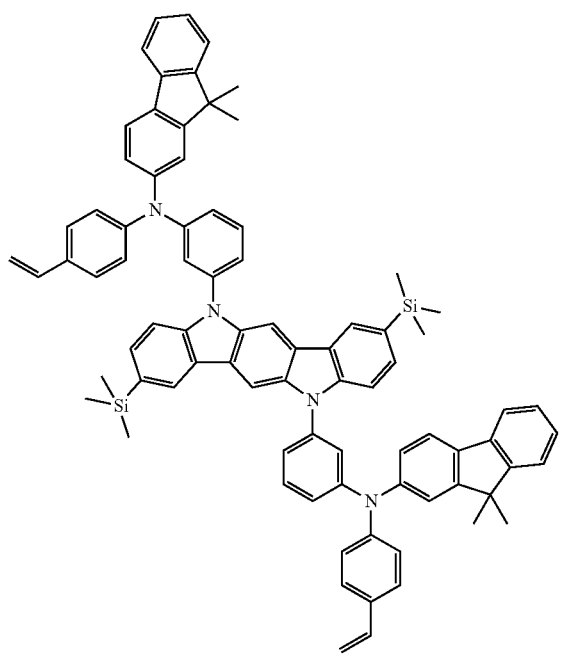

-continued
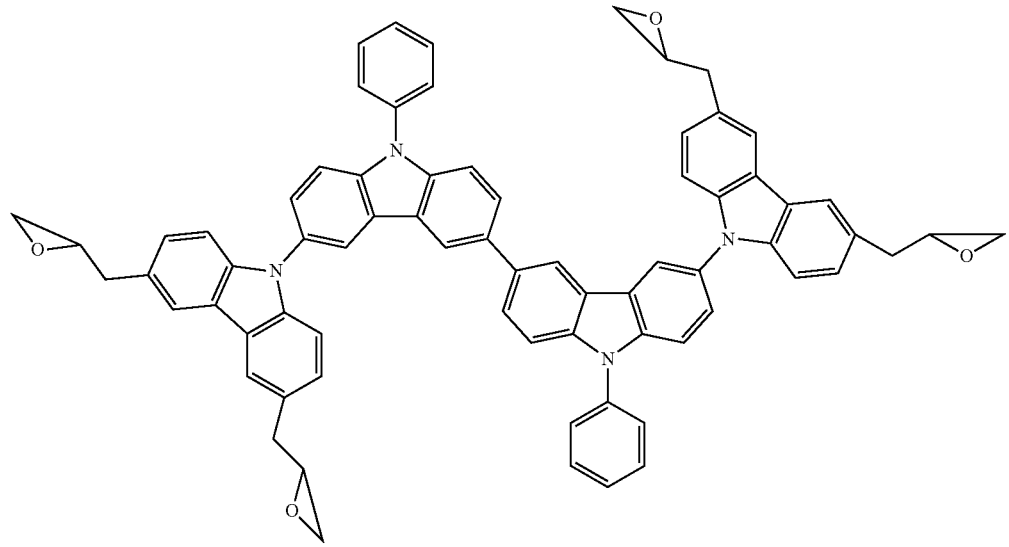
(42)
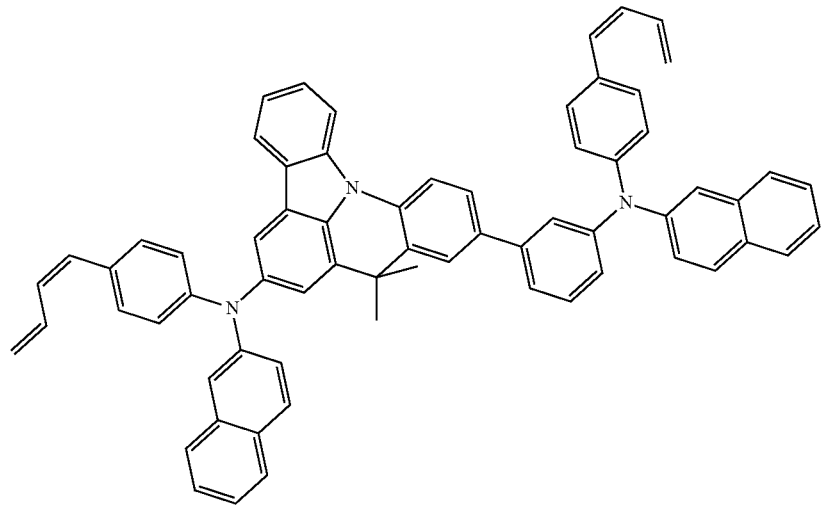
(43)
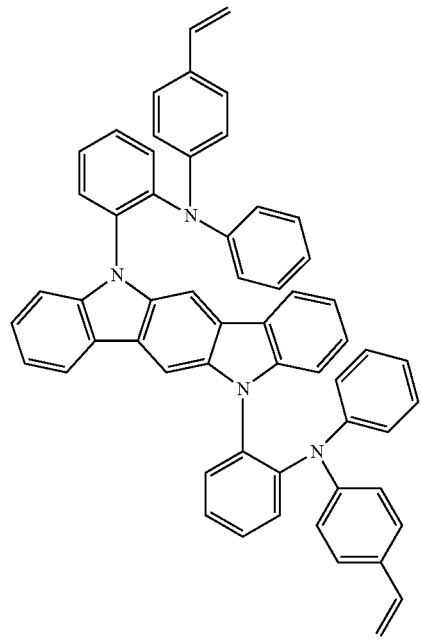
(44)

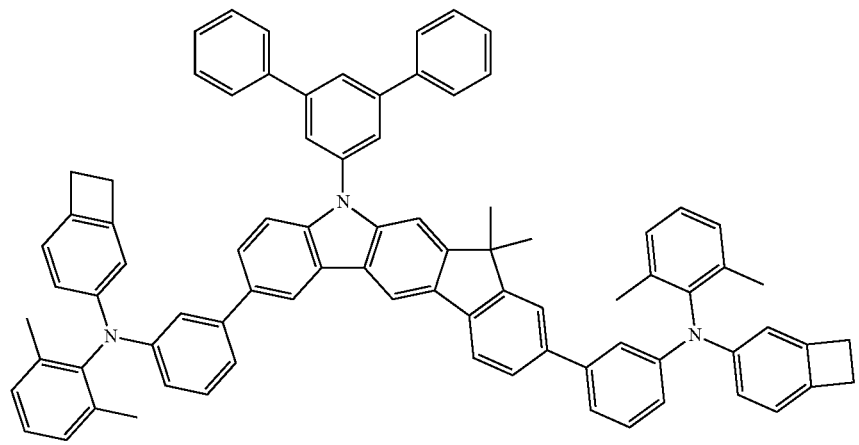
(45)
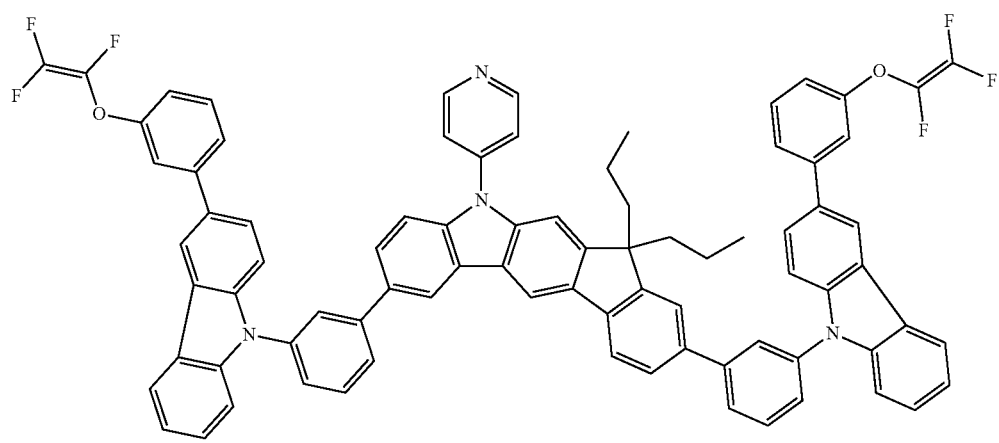
(46)
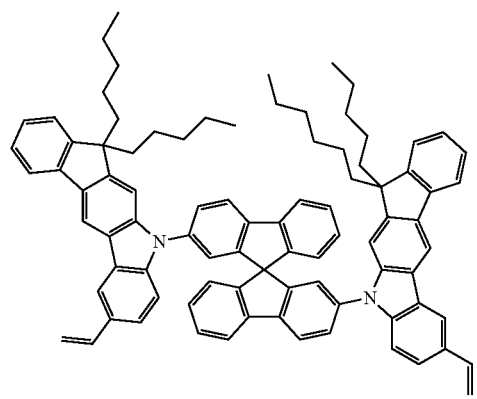
(47)
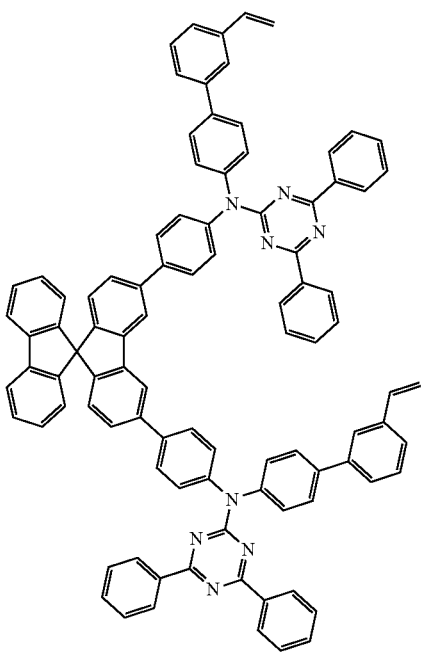
(48)

(49)
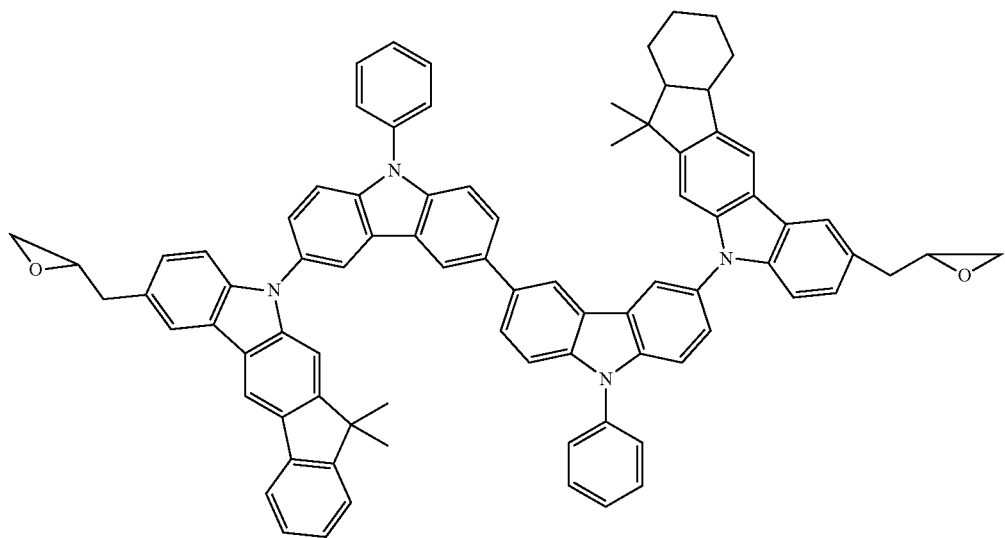
(50)
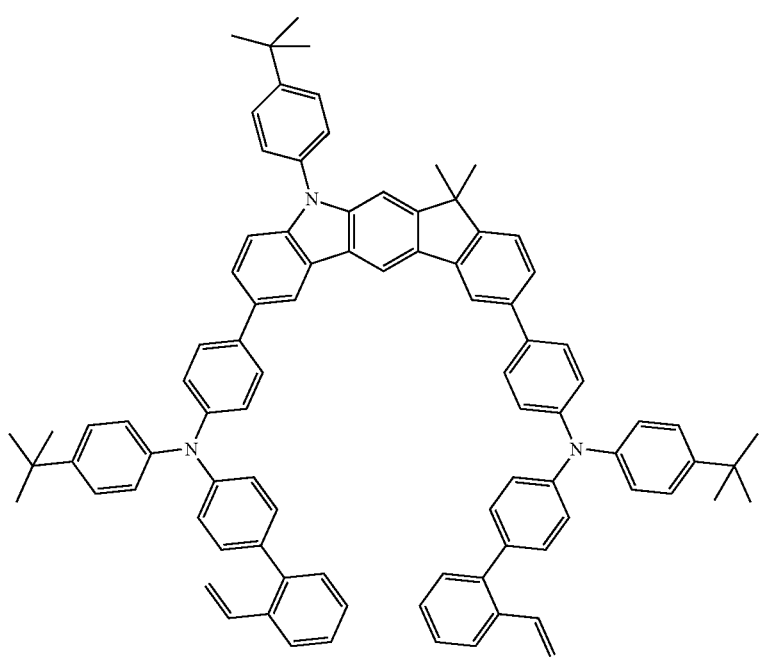

(51)
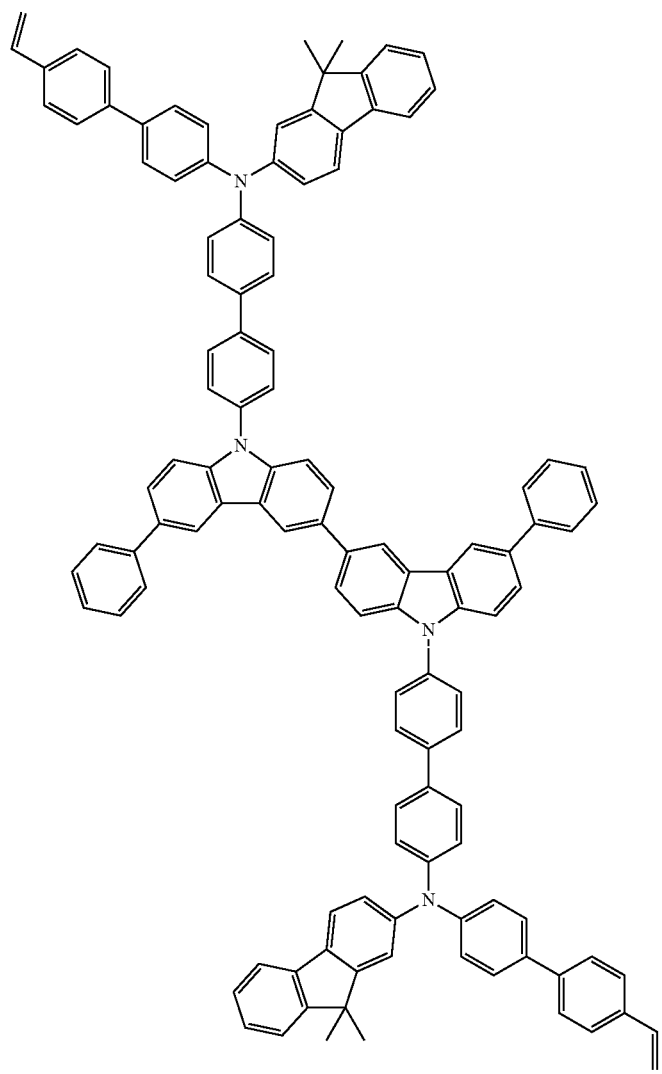
(52)
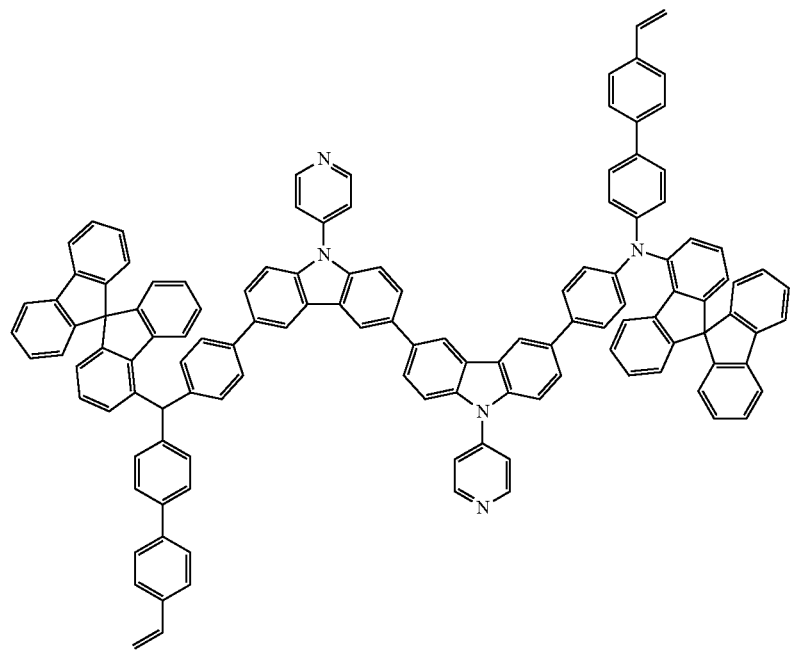

(53)
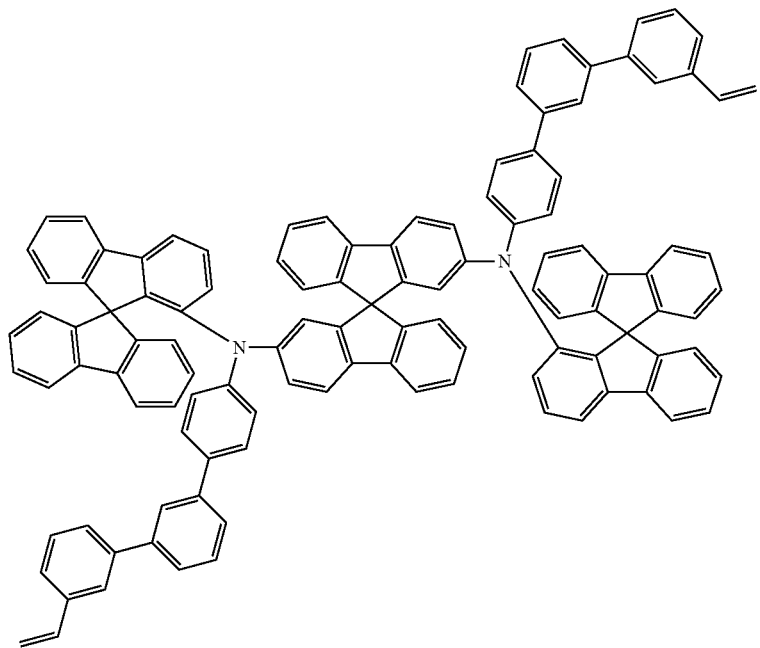
(54)
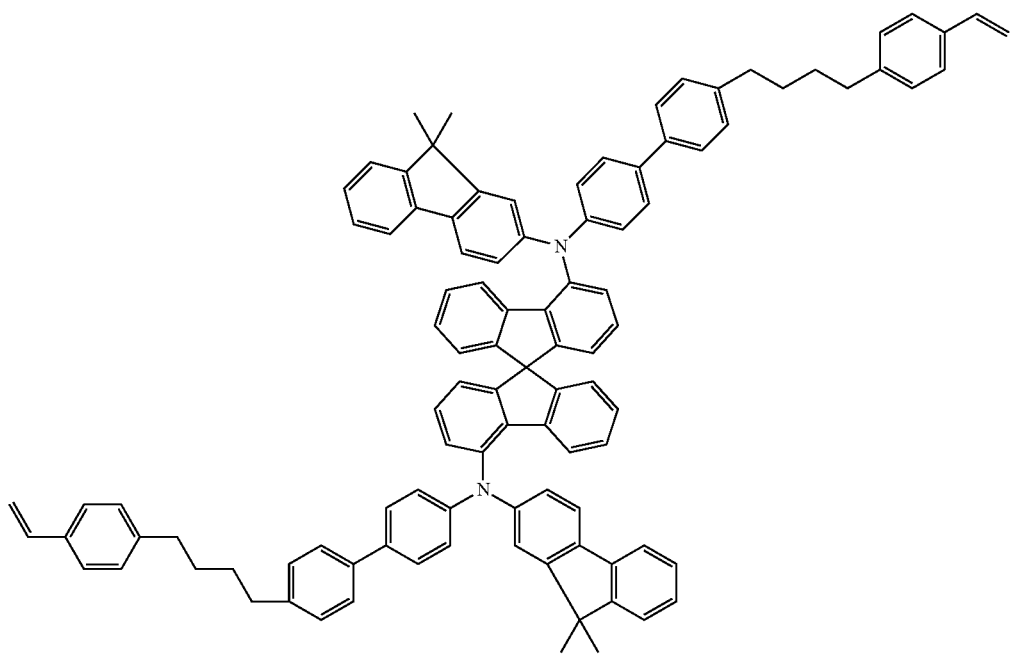

(55)
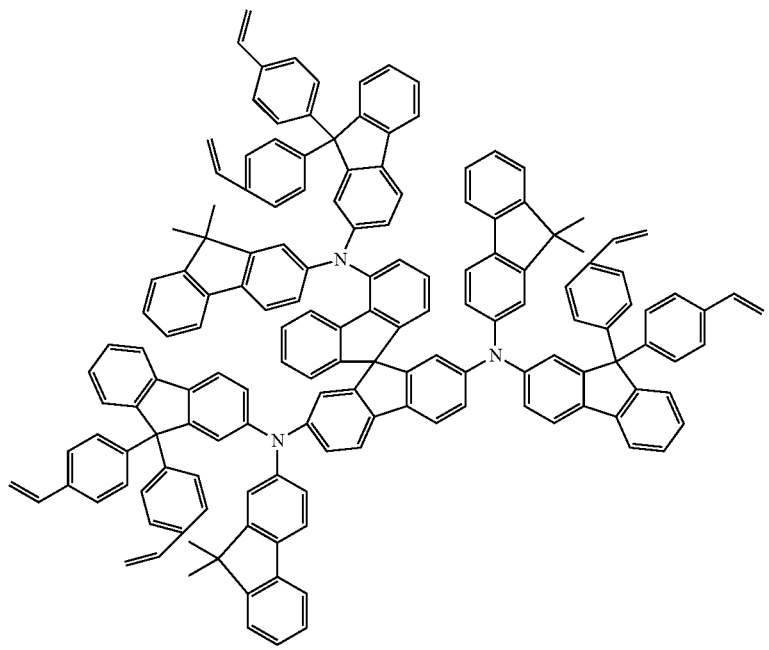
(56)
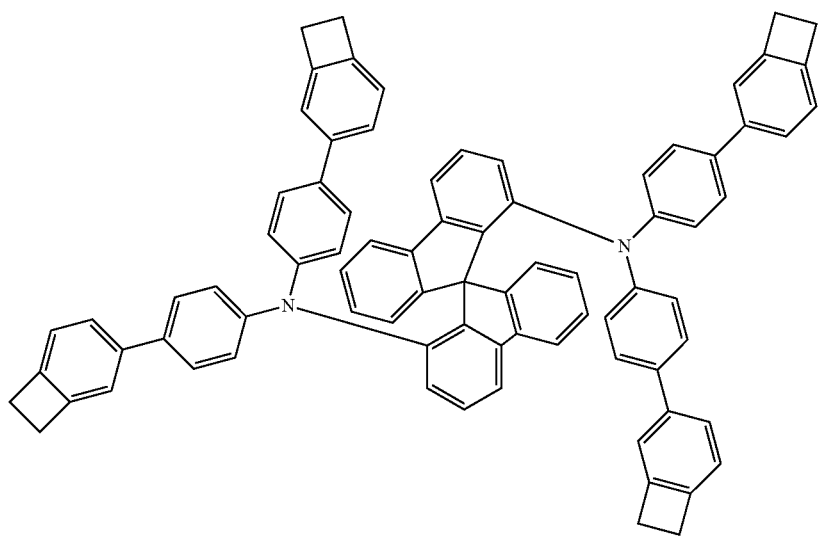

(57)
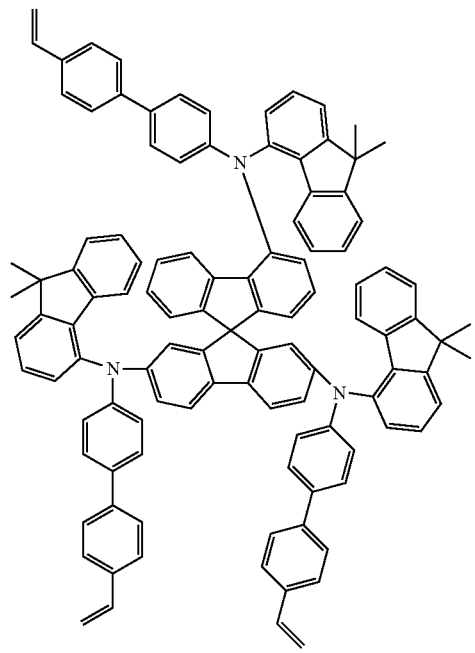
(58)
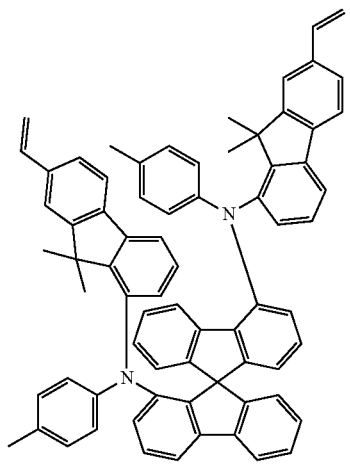
(59)
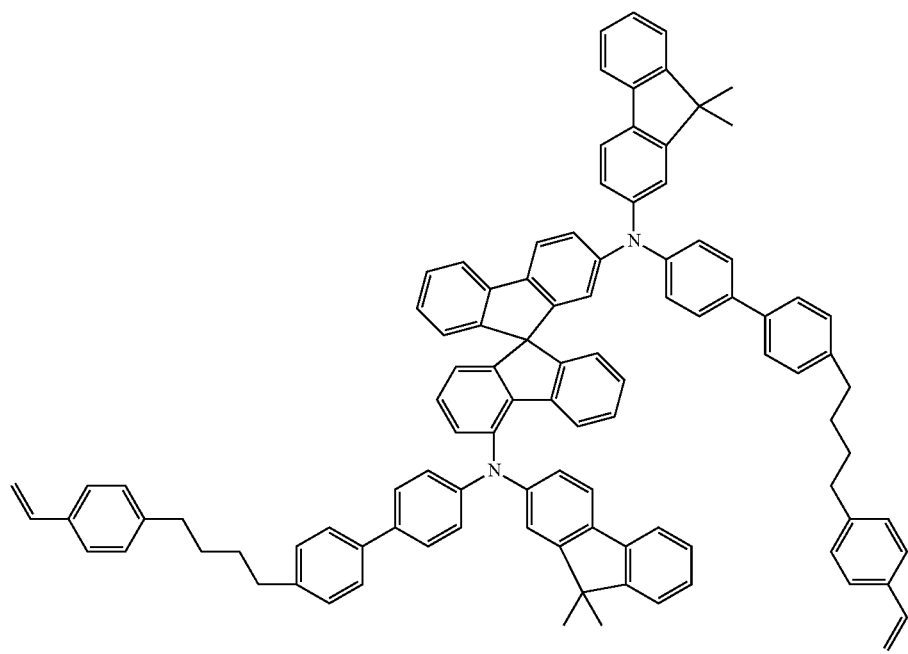

(60)

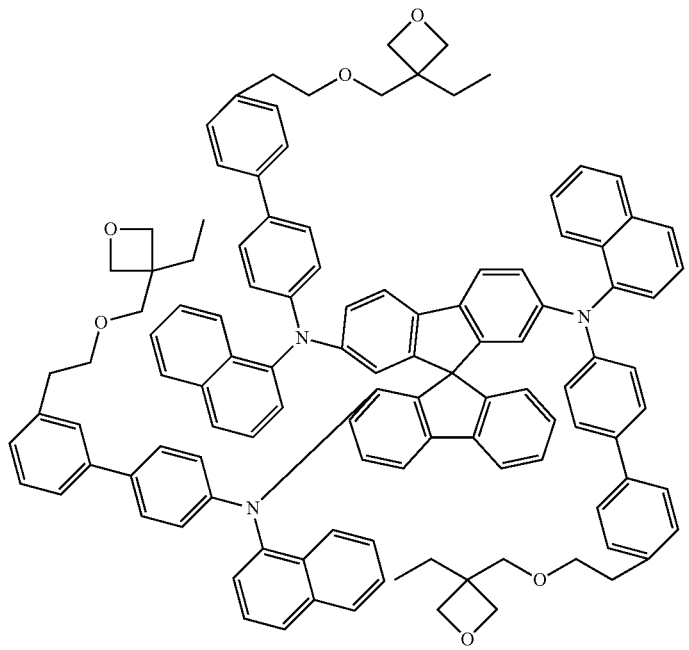

The present invention furthermore relates to a crosslinked compound which is obtainable by crosslinking the groups Q of the compound of the formula (1). A crosslinked compound in the sense of the present invention is a compound which is obtainable from the compound of the formula (1) by carrying out the reaction of the crosslinkable group Q.

The crosslinkable compound of the formula (1) can be applied by coating from solution to a corresponding support substrate (glass, polymer etc.) or a layer which has already been deposited in advance and crosslinked either before or after removal of the solvent or during removal of the solvent.

The present invention thus also relates to a layer comprising one or more compounds according to the invention as defined above or comprising one or more compounds obtained by crosslinking the compounds according to the invention.

The present invention furthermore relates to a process for the production of a crosslinked layer by application and crosslinking of a compound of the formula (1). The compound of the formula (1) here can be crosslinked as pure substance, or it can be applied as a mixture with at least one other crosslinkable or polymerisable compound and crosslinked together with the latter. In a preferred embodiment of the invention, the compound of the formula (1) is crosslinked as pure substance.

The layer can be produced, for example, by coating from solution, preferably by gravure printing, ink-jet printing, nozzle printing, flexographic printing, dye coating, screen printing or spin coating. After application of a layer of the compound of the formula (1) and optionally removal of the solvent, the compound can be crosslinked. The crosslinking is preferably carried out with radiation induction (for example using UV light, visible light, microwaves, electron beams) or thermally, in particular thermally.

The present invention furthermore relates to a formulation comprising at least one compound of the formula (1) and one or more solvents. The way in which formulations of this type can be prepared is known to the person skilled in the art and described, for example, in WO 2002/072714, WO 2003/019694 and the literature cited therein.

Suitable and preferred solvents are, for example, toluene, anisole, xylenes, methyl benzoate, dimethylanisoles, mesitylenes, tetralin, veratrol, tetrahydrofuran and chlorobenzene and mixtures thereof.

The present invention also relates to the use of the compounds according to the invention and the crosslinked compounds obtained therefrom in an electronic device.

The present invention again furthermore relates to an electronic device comprising one or more compounds of the formula (1) or one or more crosslinked compounds obtained by crosslinking the compound of the formula (1).

The electronic device is preferably an organic electroluminescent device (OLED), an organic integrated circuit (O-IC), an organic field-effect transistor (O-FT), an organic thin-film transistor (O-TFT), an organic, light-emitting transistor (O-LET), an organic solar cell (O-SC), an organic, optical detector, an organic photoreceptor, an organic field-quench device (O-FQD), a light-emitting electrochemical cell (LEC) or an organic laser diode (O-laser), preferably an organic electroluminescent device (OLED).

In a further embodiment of the present invention, the device comprises a plurality of layers. The compound of the formula (1) according to the invention or the crosslinked compound obtained therefrom may be present here in a hole-transport, hole-injection, emitter, electron-transport, electron-injection, charge-blocking and/or charge-generation layer.

The organic electroluminescent device according to the invention comprises cathode, anode and at least one emitting layer. Apart from these layers, the organic electroluminescent device may also comprise further layers, for example in each case one or more hole-injection layers, hole-transport layers, hole-blocking layers, electron-transport layers, electron-injection layers, exciton-blocking layers and/or charge-generation layers. Interlayers, which have, for example, an exciton-blocking function, may likewise be introduced between two emitting layers. However, it should be pointed out that each of these layers does not necessarily have to be present. It is also possible for a plurality of OLEDs to be arranged one above the other, enabling a further increase in efficiency to be achieved with respect to the light yield. In order to improve the coupling-out of light, the final organic layer on the light exit side in OLEDs may also be, for example, in the form of a nanofoam or another material having a low refractive index, resulting in a reduction in the proportion of total reflection.

It is also possible for the organic electroluminescent device according to the invention to comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers.

The device may comprise layers which are built up from low-molecular-weight compounds. These can be produced by vapour deposition of the compounds in a high vacuum or by application from solution. The device may likewise comprise layers which are built up from oligomeric, polymeric or dendritic compounds. These are produced, in particular, by application from solution.

The organic electroluminescent device according to the invention preferably has the following structure: anode/ optionally layer comprising a conductive polymer/one or more crosslinked layers, obtainable by crosslinking the compound of the formula (1)/emission layer and cathode.

In a preferred embodiment of the present invention, the compounds according to the invention and the crosslinked compounds obtained therefrom are used in a hole-transport layer or in a hole-injection layer. This layer is used as interlayer between the anode or the conductive polymer and the emitting layer. A hole-injection layer in the sense of the present invention denotes a layer which is directly adjacent to the anode. A hole-transport layer in the sense of the present invention denotes a layer which is arranged between a hole-injection layer and an emitting layer.

The crosslinked hole-transport layer or the crosslinked hole-injection layer may also be doped here, in particular by electron-acceptor compounds, for example by $F_4$-TCNQ or by compounds as described in EP 1476881 or EP 1596445.

In particular for lighting applications, it is preferred for a p-doped layer of the compound of the formula (1) to be applied directly to the anode and crosslinked there. An additional layer comprising a conductive polymer is not necessary here, i.e. the crosslinked layer obtained by crosslinking the compound of the formula (1) serves as replacement for the doped conductive polymer. The layer thickness of this layer is preferably between 10 and 400 nm, particularly preferably between 50 and 350 nm.

The compounds of the formula (1) according to the invention and the crosslinked compounds according to the invention obtained therefrom are furthermore preferably used in a hole-transport layer, where this hole-transport layer is applied to a layer of a conductive polymer. Suitable as conductive polymer are all materials as usually used for this layer by the person skilled in the art, for example PEDOT/ PSS, doped PANI or doped oligoanilines. The layer thickness of the hole-transport layer according to the invention is usually in the range from 10 to 400 nm, preferably in the range from 50 to 200 nm.

All materials as are usually used in organic electroluminescent devices and as are known to the person skilled in the art can be used in the further layers.

If the emitting layer used is a phosphorescent layer, this preferably consists of low-molecular-weight compounds which are applied from solution.

If the emitting layer used is a blue fluorescent layer, this preferably consists of low-molecular-weight compounds which are either applied from solution or applied by vacuum vapour deposition.

In particular in the above-mentioned cases of phosphorescent or blue-fluorescent emitter layers, but also in other electroluminescent devices, it is preferred for the organic electroluminescent device to comprise an electron-transport layer. This is preferably applied to the emitting layer by vapour deposition. Suitable materials for the electron-transport layer are benzimidazole derivatives, triazine derivatives and/or hydroxyquinoline complexes, such as, for example, LiQ (lithium quinolinate).

Preference is given to an organic electroluminescent device which is characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. The compound of the formula (1) is particularly preferably applied from solution.

Preference is furthermore given to an organic electroluminescent device in which one or more layers are coated by means of a sublimation process, in which the materials are applied by vapour deposition in vacuum sublimation units at a pressure less than $10^{-5}$ mbar, preferably less than $10^{-6}$ mbar, particularly preferably less than $10^{-7}$ mbar.

Preference is likewise given to an organic electroluminescent device which is characterised in that one or more layers are coated by means of the OVPD (organic vapour phase deposition) process or with the aid of carrier-gas sublimation, in which the materials are applied at a pressure between $10^{-5}$ mbar and 1 bar.

It is also possible to produce the organic electroluminescent device as hybrid device by, for example, applying one or more layers from solution and applying one or more further layers by vacuum vapour deposition. Thus, for example, the layer comprising the compound of the formula (1) can be applied from solution and the emitting layer can be applied by vapour deposition. It is likewise possible to apply the layer comprising the compound of the formula (1) and the emitting layer from solution and to apply the electron-transport layer by vapour deposition.

The device usually comprises a cathode and an anode (electrodes). For the purposes of the present invention, the electrodes are selected so that their potential matches as closely as possible the potential of the adjacent organic layer in order to ensure highly efficient electron or hole injection.

The cathode preferably comprises metal complexes, metals having a low work function, metal alloys or multilayered structures containing various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Ba/Al, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides (for example LiF, $Li_2O$, $BaF_2$, MgO, NaF, etc.). The layer thickness of this layer is preferably between 1 and 10 nm, particularly preferably between 2 and 8 nm.

The anode preferably comprises materials having a high work function. The anode preferably has a potential of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order to facilitate either irradiation of the organic material (O-SCs) or the coupling-out of light (OLEDs/PLEDs, O-lasers). A preferred construction uses a transparent or partially transparent anode. Preferred anode materials here are conductive mixed metal oxides. Particular preference is given to indium tin oxide (ITO) or indium zinc oxide (IZO). Preference is furthermore given to conductive doped organic materials, in particular conductive doped polymers, such as, for example, poly(ethylenedioxythiophene) (PEDOT) and polyaniline (PANI).

As layer directly on the anode, use is preferably made of conductive doped polymers, such as, for example, in each case doped poly(ethylenedioxythiophene) (PEDOT), polyaniline (PANI) or oligoaniline, if a layer according to the invention is not used for this purpose.

The device is correspondingly structured, depending on the application, provided with contacts and finally hermetically sealed, since the lifetime of such devices is drastically shortened in the presence of water and/or air.

The invention is explained in greater detail by the following examples. The person skilled in the art will be able to use the descriptions to produce further electronic devices according to the invention without inventive step and thus carry out the invention throughout the range claimed.

EXAMPLES

The following syntheses are carried out, unless indicated otherwise, under a protective-gas atmosphere in dried solvents. The solvents and reagents can be purchased, for example, from Sigma-ALDRICH or ABCR. The figures in square brackets for literature-known chemical compounds relate to the CAS number.

Example 1

Synthesis of Compound 3

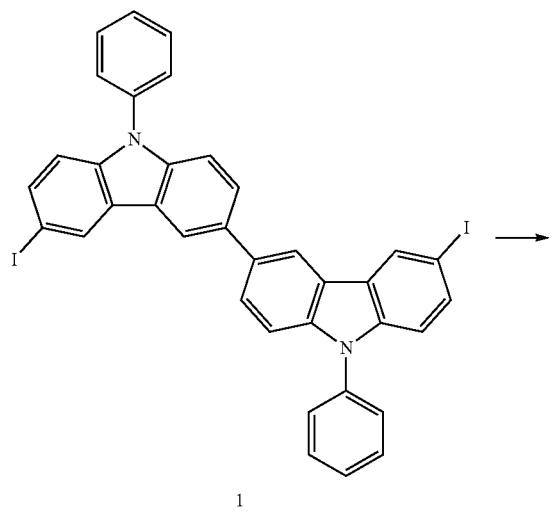

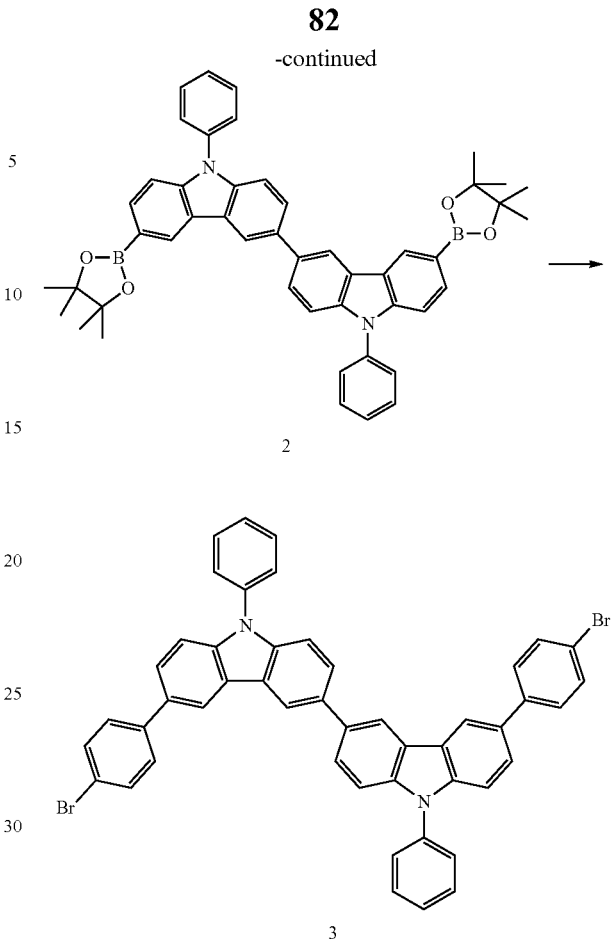

a) Synthesis of Compound 2

100 g (136 mmol; 1.0 eq.) of compound 1 [57102-64-4], 135 g (0.53 mol; 3.9 eq.) of bis(pinacolato)diborane and 160 g (1.63 mol; 12 eq.) of potassium acetate are suspended in 1.1 l of degassed dioxane in a flask which has been dried by heating. The suspension is degassed for 30 minutes, and 4.40 g (5.44 mmol; 0.04 eq.) of PdCl$_2$(dppf).CH$_2$Cl$_2$ as catalyst are then added. The reaction mixture is heated under reflux for 72 hours. The brown precipitate is filtered and washed with 1 l of water. Dichloromethane is added to the solid obtained, and the mixture is extracted with water. The organic phases are combined, dried over Na$_2$SO$_4$, filtered, and the solvents are removed in vacuo, giving 68.0 mmol (50%, HPLC purity 95%) of a brown solid. Compound 2 obtained is recrystallised twice from o-xylene and then extracted with hot o-xylene over aluminium oxide, giving a pale-beige solid, which is recrystallised from DMF. The product is subsequently recrystallised a number of times from anisole until an HPLC purity of 99.2% is achieved. The yield is 22.9 g (31.2 mmol), corresponding to 22.9% of theory.

b) Synthesis of Compound 3

22.9 g (31.2 mmol; 1.0 eq.) of compound 2, 22.1 g (78.1 mmol; 2.5 eq.) of 1-bromo-4-iodobenzene and 10.6 g of sodium carbonate (99.9 mmol; 3.2 eq.) are suspended in a mixture of degassed water/toluene/dioxane (185/160/90 ml). The suspension is degassed for 30 minutes, and 721 mg (0.625 mmol; 0.02 eq.) of Pd(PPh$_3$)$_4$ are then added. The reaction mixture is subsequently heated under reflux for 27 hours and filtered when the reaction is complete. The white-beige solid is washed with each of water, toluene and finally with heptane, and the residue is dried at 85° C. in a vacuum drying cabinet. The crude product obtained (24.5 mmol) is recrystallised from DMF and subsequently from chlorobenzene until an HPLC purity of 99% has been achieved. The yield is 7.95 g (10 mmol), corresponding to 32% of theory.

Example 2

Synthesis of Compound 8

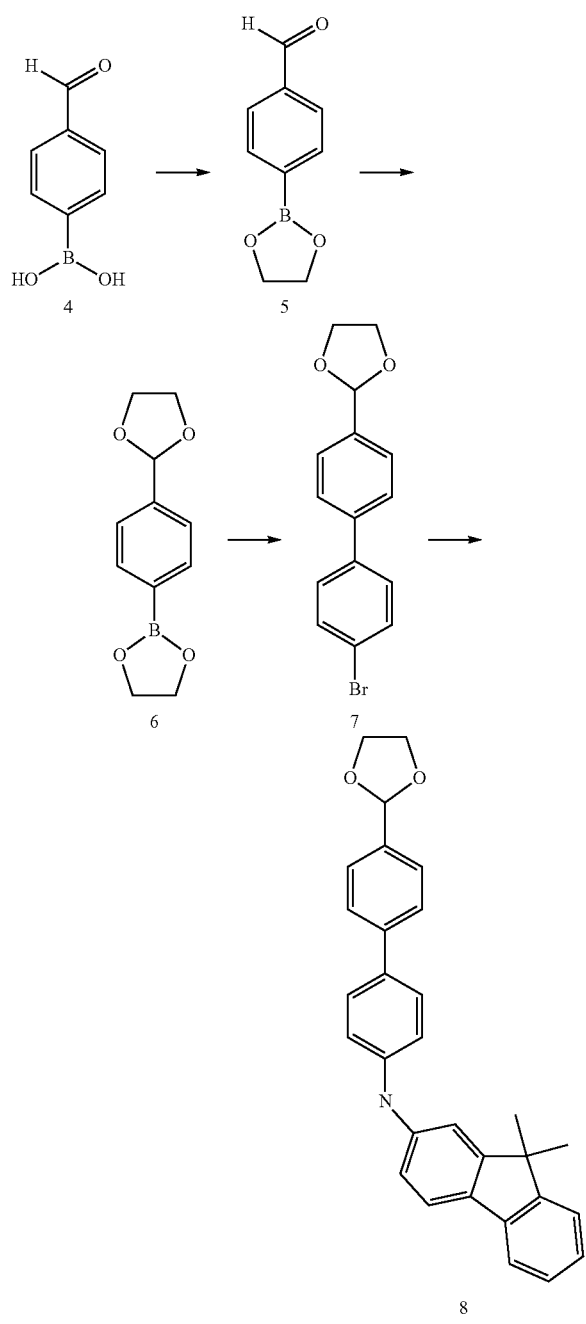

a) Synthesis of Compound 5

5.00 g (33.0 mmol; 1.0 eq.) of 4-formylphenylboronic acid (compound 4) are suspended in 30 ml of toluene. 1.9 ml of ethylene glycol (33.0 mmol; 1.0 eq.) are then added. The reaction mixture is stirred under reflux for 2.5 hours, and the water obtained is removed continuously using a water separator. The reaction mixture is cooled to room temperature, and the solvents are removed in vacuo. The yield is 5.86 g (33.0 mmol), corresponding to 100% of theory.

b) Synthesis of Compound 6

5.86 g (33.0 mmol; 1.0 eq.) of compound 5 are suspended in 150 ml of toluene with 10.0 g of aluminium oxide (acidic). 11.3 ml of ethylene glycol (200 mmol; 6.0 eq.) are then added. The reaction mixture is stirred under reflux for 24 hours. When the reaction is complete, the batch is filtered, and the aluminium oxide is washed with dichloromethane. The organic phases are combined, and the solvents are removed in vacuo. The yield is 7.00 g (32.0 mmol), corresponding to 97% of theory.

c) Synthesis of Compound 7

14.5 g of 2-(4-1,3-dioxolan-2-ylphenyl)-1,3,2-dioxaborolane (compound 6) (66.0 mmol; 1.0 eq.), 18.7 g of 1-bromo-4-iodobenzene (66.0 mmol; 1.0 eq.) and 18.2 g of sodium carbonate (132 mmol; 2.0 eq.) are suspended in a mixture of degassed water/toluene (85/220 ml). The suspension is degassed for 30 minutes, and 763 mg (0.66 mmol; 0.01 eq.) of Pd(PPh$_3$)$_4$ are subsequently added. The reaction mixture is stirred under reflux for 24 hours and, when the reaction is complete, washed with 75 ml of a hydrogencarbonate solution (0.6 M; pH=8.2). The organic phase is dried over Na$_2$SO$_4$, filtered, and the solvents are removed in vacuo. The yellow solid obtained is stirred in 25 ml of heptane at 60° C. for 3 hours. The suspension is subsequently filtered, the solid is dissolved in dichloromethane and filtered through Celite. After removal of the solvent in vacuo, the yield is 13.3 g (43.6 mmol), corresponding to 66% of theory.

d) Synthesis of Compound 8

3.80 g of 2-(4'-bromobiphenyl-4-yl)-1,3-dioxolane (compound 7) (12.0 mmol; 1.0 eq.), 2.60 g of 9,9-dimethyl-9H-fluoren-2-ylamine (12.0 mmol; 1.0 eq.) and 1.80 g of sodium tert-butoxide (19.0 mmol; 1.5 eq.) are suspended in 30 ml of degassed toluene and degassed for 30 minutes. 28.0 mg (0.031 mmol; 0.026 eq.) of Pd(dba)$_3$ and 39.0 mg (0.062 mmol; 0.052 eq.) of BINAP are initially introduced in 10 ml of degassed toluene in a 20 ml beaded-rim vial. The catalyst solution is degassed for 15 minutes and added to the reaction mixture. The batch is heated under reflux for 5 hours. When the reaction is complete, 50 ml of toluene are added, and the reaction mixture is washed with water. The organic phase is dried over Na$_2$SO$_4$, filtered, and the solvents are removed in vacuo. The orange-brown solid is recrystallised from heptane/toluene (4:3). The yield is 2.90 g (6.70 mmol) of a yellow solid, corresponding to 54% of theory.

Example 3

Synthesis of Compound 9

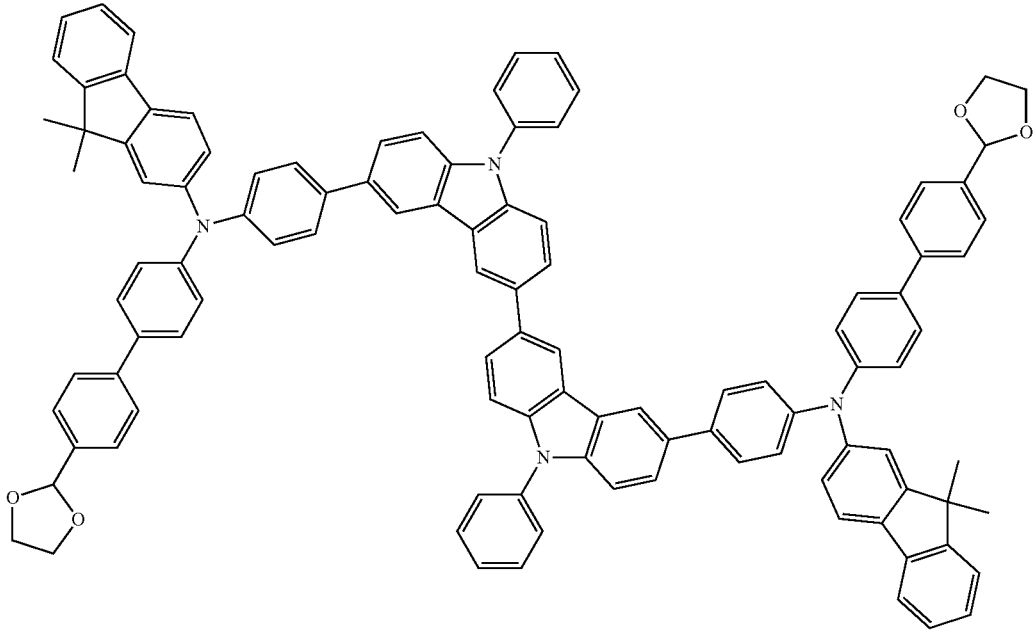

7.00 g of compound 3 (8.81 mmol; 1 eq), 8.40 g (19.4 mmol; 2.2 eq.) of compound 8 and 2.54 g of sodium tert-butoxide (26.4 mmol; 3 eq.) are suspended in 200 ml of degassed toluene and degassed for 20 minutes. 0.264 ml of tri-tert-butylphosphine 1M in toluene (0.264 mmol; 0.03 eq.) and 19.8 mg of Pd(OAc)$_2$ (0.088 mmol; 0.001 eq.) in 2 ml of degassed toluene are subsequently added to the reaction mixture. The batch is heated at 110° C. for 30 hours, and, when the reaction is complete, 200 ml of ethyl acetate and 120 ml of saturated NaHCO$_3$ solution are added. The aqueous phase is extracted with 3×200 ml of ethyl acetate. The organic phase is dried over Na$_2$SO$_4$, filtered, and the solvents are removed in vacuo. The solid is stirred in warm toluene, cooled and filtered. The yield is 7.13 g (4.75 mmol) of a yellow solid, corresponding to 54% of theory.

Example 4

Synthesis of Compound 10

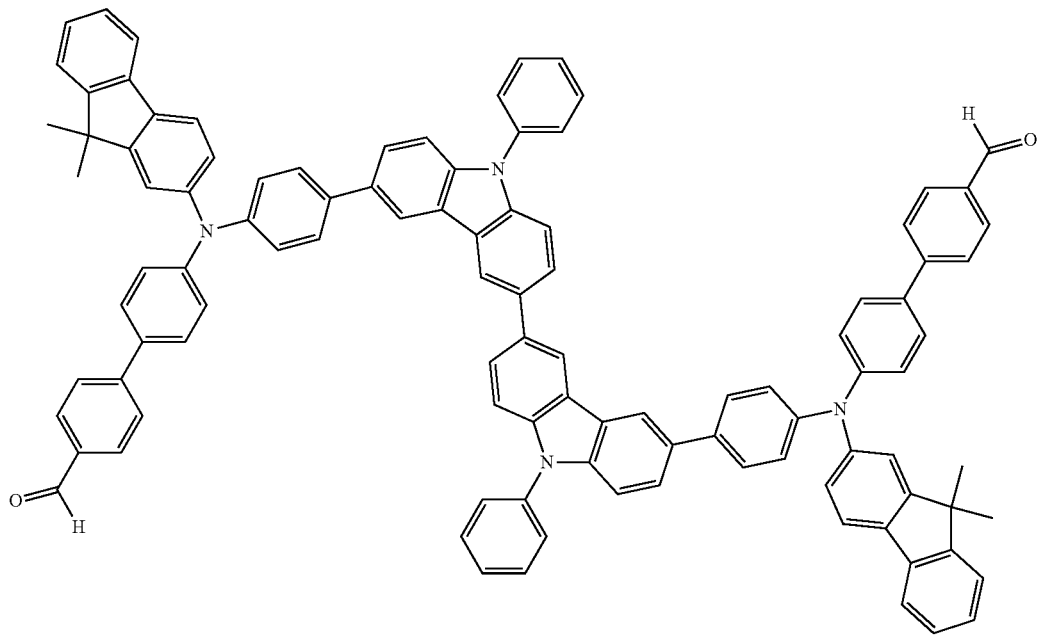

6.50 g of compound 9 (4.30 mmol; 1 eq), dissolved in 200 ml of chloroform, and 100 ml of a 7% aqueous HCl solution are heated at 75° C. for 1 hour. When the reaction is complete, the organic phase is washed with 3×200 ml of water, dried over $Na_2SO_4$ and filtered. The solvents are removed in vacuo, and the yellow residue is recrystallised in a mixture of chloroform/heptane and then tetrahydrofuran/acetonitrile. The yield is 1.95 g (1.38 mmol) of a yellow solid, corresponding to 32% of theory.

Example 5

Synthesis of Compound 11 According to the Invention

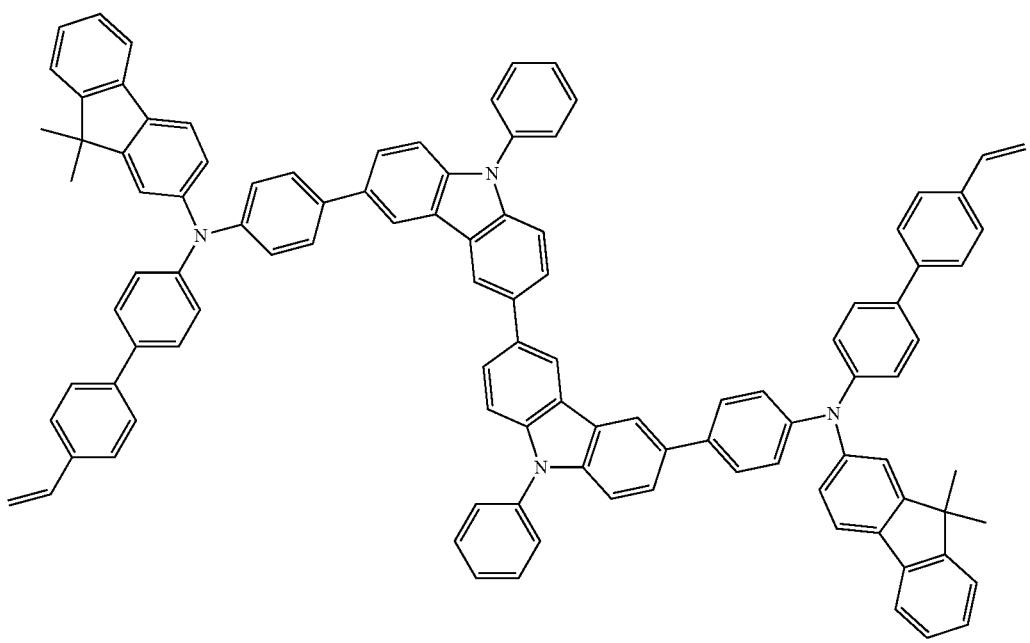

11

0.91 g (2.6 mmol; 4 eq.) of methyltriphenylphosphonium bromide are suspended in 15 ml of dried THF at 0° C. under argon. 0.29 g (2.6 mmol; 4 eq.) of potassium tert-butoxide is added in portions to the reaction mixture, which is then stirred with ice-cooling for 40 minutes. 1.0 g (0.7 mmol; 1.0 eq.) of compound 10 are dissolved in 50 ml of THF and added. The ice bath is removed after 30 minutes, and the reaction mixture is stirred at room temperature for 6 days. 60 ml of water and 120 ml of ethyl acetate are added, the organic phase is washed with 2×50 ml of water, dried over $Na_2SO_4$ and evaporated in a rotary evaporator. The residue is washed with 2×20 ml of methanol, filtered, recrystallised from chloroform/methanol and chromatographed on silica gel with dichloromethane/heptane (1/3). The yield is 0.43 g (0.3 mmol) of a pale-yellow solid, corresponding to 43% of theory.

Example 6

Synthesis of Compound 13

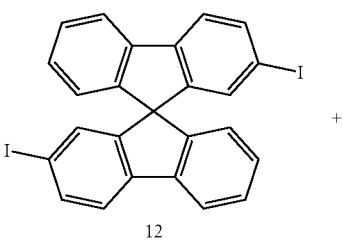

12

-continued

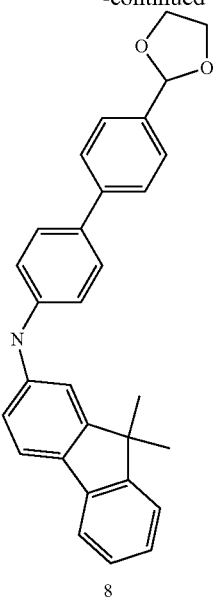

8

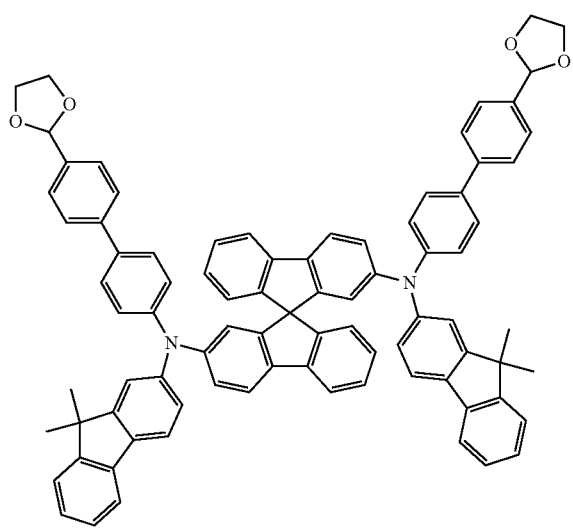

13

2.00 g (3.5 mmol; 1 eq.) of compound 12 [790674-48-5], 3.35 g (7.7 mmol; 2.2 eq.) of compound 8 and 1.01 g of sodium tert-butoxide (10.5 mmol; 3 eq.) are dissolved in 30 ml of degassed toluene and degassed for 20 minutes. 0.105 ml of tri-tert-butylphosphine 1M in toluene (0.105 mmol; 0.03 eq.) and 7.8 mg of Pd(OAc)$_2$ (0.035 mmol; 0.001 eq.) in 5 ml of degassed toluene are subsequently added to the reaction mixture. The batch is heated at 110° C. for 2.5 hours. When the reaction is complete, 200 ml of ethyl acetate are added, and the reaction mixture is filtered through Celite. The organic phase is washed with 2×60 ml of saturated NaHCO$_3$ solution, dried over Na$_2$SO$_4$, filtered, and the solvents are removed in vacuo. The solid is stirred in warm heptane/toluene, cooled and filtered. The yield is 3.40 g (2.88 mmol) of a yellow solid, corresponding to 82% of theory.

Example 7

Synthesis of Compound 14

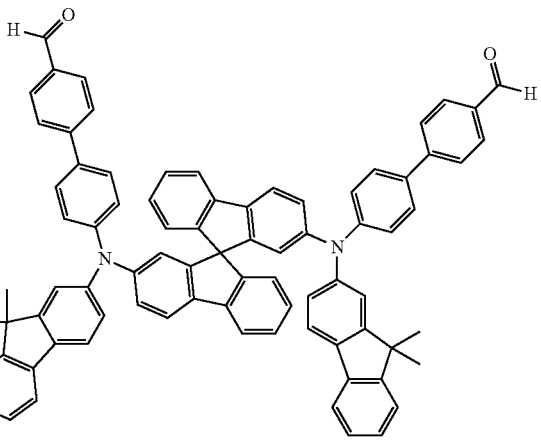

14

3.50 g of compound 13 (2.97 mmol; 1 eq), dissolved in 40 ml of chloroform, and 10 ml of a 3.5% aqueous HCl solution are heated at 75° C. overnight. When the reaction is complete, the organic phase is washed with 30 ml of saturated solution NaHCO$_3$ and 2×200 ml of water, dried over Na$_2$SO$_4$ and filtered. The solvents are removed in vacuo, and the yellow residue is recrystallised from toluene/heptane and from chloroform/heptane. The yield is 2.9 g (2.66 mmol) of a yellow solid, corresponding to 90% of theory.

Example 8

Synthesis of Compound 15 According to the Invention

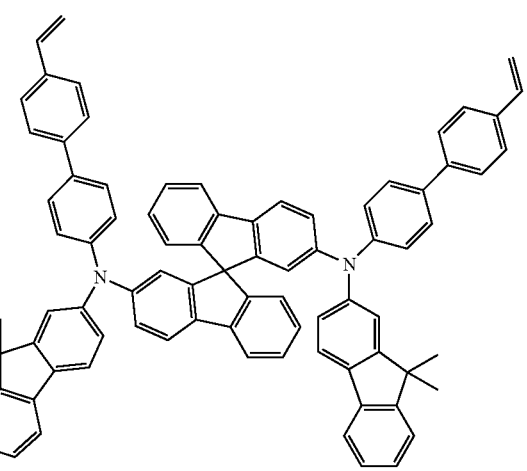

15

3.00 g (9.2 mmol; 4 eq.) of methyltriphenylphosphonium bromide are suspended in 100 ml of dried THF at 0° C.

under argon. 1.03 g (9.2 mmol; 4 eq.) of potassium tert-butoxide are added in portions to the reaction mixture, which is then stirred with ice-cooling for 30 minutes. 2.5 g (2.3 mmol; 1.0 eq.) of compound 14 is dissolved in 100 ml of THF and added. The ice bath is removed after 30 minutes, and the reaction mixture is stirred at room temperature for 1 hour. 120 ml of water and 200 ml of DCM are added, the organic phase is washed with 2×50 ml of water, dried over $Na_2SO_4$ and evaporated in a rotary evaporator. The residue is washed with 2×20 ml of methanol, filtered and recrystallised from chloroform/methanol and DMF/methanol. The yield is 1.75 g (1.6 mmol) of a pale-yellow solid, corresponding to 70% of theory.

Example 9

Electroluminescent Devices

The production of an organic light-emitting diode (OLED) processed from solution has already been described many times in the literature (for example in WO 2004/037887). In order to explain the present invention by way of example, OLEDs are produced by spin coating with material 1 and comparative material 1.

A typical OLED has the structure shown below, where material 1 according to the invention fulfils the function of a hole-transport layer (HTL).

| 3 nm/100 nm | Cathode | Ba/Al |
| 80 nm | EML | EML |
| 20 nm | HTL | Material 1 or comparison 1 |
| 80 nm | Buffer | PEDOT:PSS |
| | Anode | ITO |

A glass coated with indium tin oxide (ITO) represents the substrate. This is cleaned with deionised water and a detergent in a clean room and then activated by a UV/ozone plasma treatment. A layer of PEDOT:PSS (Baytron P VAI 4083sp from H.C. Starck (now Heraeus Clevios) which is supplied as an aqueous dispersion) with a thickness of 80 nm is then applied by spin coating, likewise in the clean room. The spin rate required depends on the degree of dilution and the specific spin-coater geometry (typically for 80 nm: 4500 rpm). In order to remove residual water from the layer, the substrates are dried by heating on a hot plate at 180° C. for 10 minutes. Then, in inert-gas atmosphere (nitrogen or argon), firstly 20 nm of the HTL layer are applied. The application is carried out by spin coating from a toluene solution. This layer is subsequently heated at 180° C. for 1 hour in order to activate the crosslinking process. 80 nm of the emission layer EML are then subsequently applied by means of spin coating, likewise from a toluene solution. This layer is dried by heating at 180° C. for 10 minutes.

Material 1:

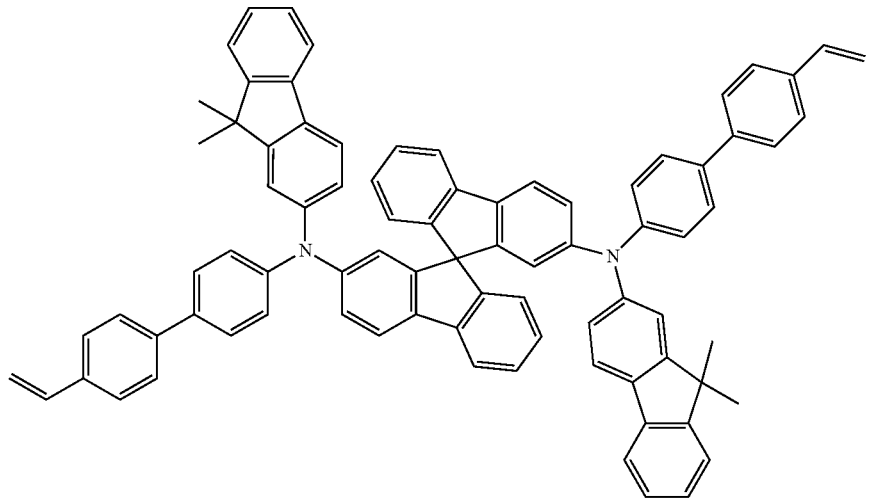 [SMILES: C=Cc1ccc(-c2ccc(N(c3ccc4c(c3)C(C)(C)c3ccccc3-4)c3ccc4c(c3)C3(c5ccccc5-4)c4ccccc4-c4ccc(N(c5ccc(-c6ccc(C=C)cc6)cc5)c5ccc6c(c5)C(C)(C)c5ccccc5-6)cc43)cc2)cc1]

Comparison 1 (in Accordance with WO 2010/097155):

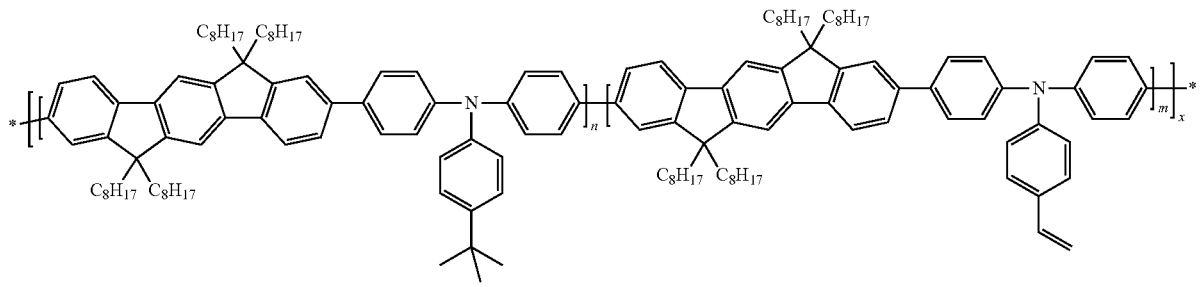

n=0.9, m=0.1
Degree of polymerisation: 250

The materials used for the emission layer (EML) is a mixture of two matrix materials (M1 and M2) and a phosphorescent green emitter (E1) in a mixing ratio (based on the weight) of M1:M2:E1=2:2:1.

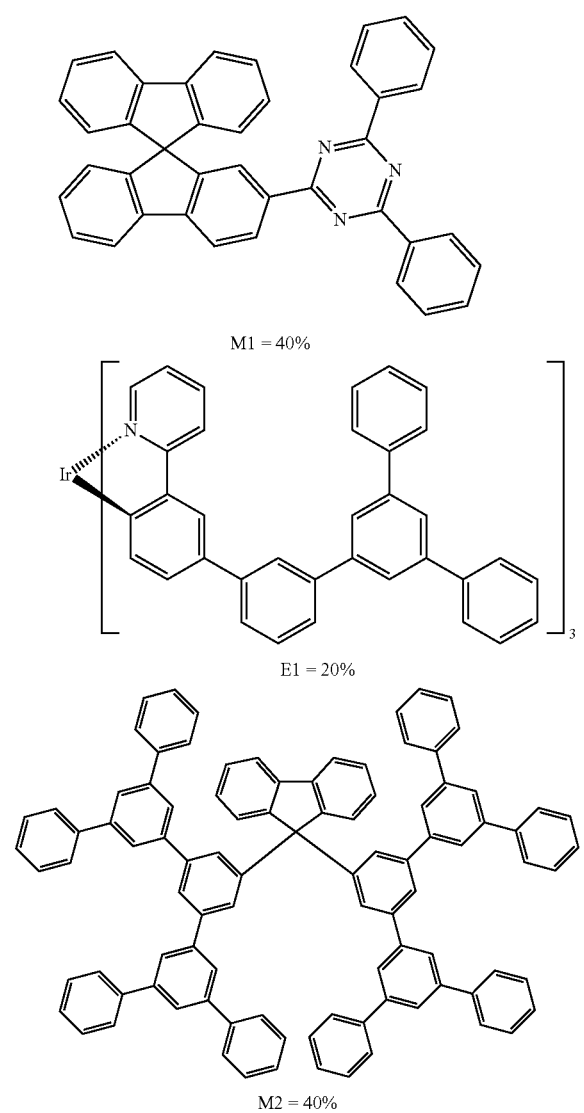

A Ba/Al cathode is subsequently applied by vapour deposition through a shadow mask (high-purity metals from Aldrich, particularly barium 99.99%); vapour-deposition units from Lesker or others, typical vacuum level 5×10⁻⁶ mbar; layer thickness Ba/Al 3 nm/100 nm). In order to protect the cathode against air and atmospheric moisture, the OLEDs are finally encapsulated and then characterised.

The current/voltage/luminous density (IVL) characteristic line of the OLEDs is obtained by increasing the applied voltage in steps (typically from 0 to max. 10 V in 0.2 V steps) and for each measurement point measuring the current through the devices and the resultant photocurrent of a calibrated photodiode which is located directly above the OLED. Important parameters are the measured current efficiency [luminous density/current density [cd/A]] and voltage, in each case at a luminous density of 1000 cd/m². For measurement of the electroluminescence spectrum and the colour of the OLEDs, the emitted light is conducted into a spectrometer (Ocean Optics) via an optical fibre. The colour coordinates (CIE: Commission International de l'éclairage, 1931 standard observer) can be calculated from the measured spectrum. A further important parameter is the lifetime (LT). LT50 denotes the time by which the initial luminous density (here 1000 cd/m²) has dropped to half on operation at constant current density.

The results on use of the material according to the invention and the comparative material are summarised in Table 1.

TABLE 1

| | Current efficiency [cd/A] @ 1000 cd/m² | U [V] @ 1000 cd/m² | CIE [x/y] | LT50 [h] @ 1000 cd/m² |
|---|---|---|---|---|
| Comparison 1 | 30 | 5.6 | 0.34/0.62 | 41000 |
| Material 1 | 38 | 5.1 | 0.34/0.62 | 53000 |

As can be seen from the results in Table 1, material 1 according to the invention exhibits an advantage with respect to operating voltage, current efficiency and lifetime compared with the comparative material.

The invention claimed is:
1. A compound of the formula (1),

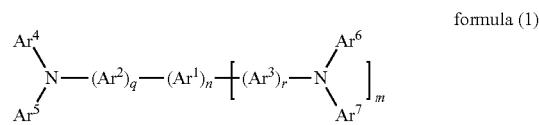

where the following applies to the symbols and indices used:

Ar¹ is, identically or differently on each occurrence, a group of the following formula (2),

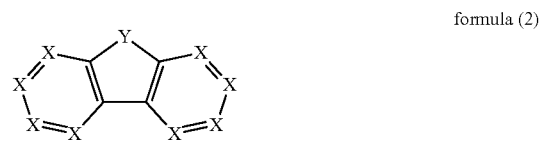

where the structure of the formula (2) can be linked at any desired positions to Ar² and Ar³ or to N or to further groups Ar¹ for n>1;

Y is N if the group of the formula (2) is linked via this N to Ar² or Ar³ or N or Ar¹ for n>1 or is, identically or differently on each occurrence, NR, O, S, CR=CR, CR₂—CR₂ or a group of the following formula (3),

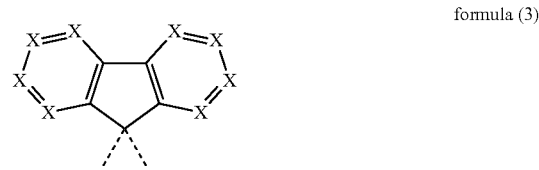

where the dashed bonds denote the linking of the group;

or Y may furthermore also stand for CR$_2$ if two adjacent groups X together stand for a group of the formula (4), (5) or (6);

X is C if the group of the formula (2) is linked via this X to Ar$^2$ or Ar$^3$ or N or Ar$^1$ for n>1 or is, identically or differently on each occurrence, CR or N; or two adjacent groups X together stand for a group of the following formula (4), (5) or (6),

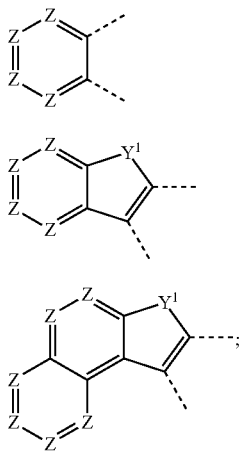

formula (4)

formula (5)

formula (6)

where the dashed bonds denote the linking of the group;

Z is C if the group of the formula (4) or formula (5) or formula (6) is linked via this X to Ar$^2$ or Ar$^3$ or N or Ar$^1$ for n>1 or is on each occurrence, identically or differently, CR or N;

Y$^1$ is on each occurrence, identically or differently, CR$_2$, NR, O or S;

Ar$^2$, Ar$^3$ is on each occurrence, identically or differently, an aryl or heteroaryl group having 5 to 18 aromatic ring atoms, which may be substituted by one or more radicals R;

Ar$^4$ to Ar$^7$ are selected, identically or differently on each occurrence, from the group consisting of phenyl, ortho-, meta- or para-biphenyl, ortho-, meta- or para-terphenyl, linear or branched quaterphenyl, fluorenyl, spirobifluorenyl and carbazolyl, each of which may be substituted by one or more radicals R;

R is on each occurrence, identically or differently, H, D, F, Cl, Br, I, N(R$^1$)$_2$, CN, NO$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals R$^1$, where one or more non-adjacent CH$_2$ groups may be replaced by R$^1$C=CR$^1$, C≡C, Si(R$^1$)$_2$, C=O, C=S, C=NR$^1$, P(=O)(R$^1$), SO, SO$_2$, NR$^1$, O, S or CONR$^1$ and where one or more H atoms may be replaced by D, F, Cl, Br, I or CN, or an aromatic or heteroaromatic ring system having 5 to 60 aromatic ring atoms, which may in each case be substituted by one or more radicals R$^1$, or an aryloxy or heteroaryloxy group having 5 to 60 aromatic ring atoms, which may be substituted by one or more radicals R$^1$, or an aralkyl or heteroaralkyl group having 5 to 60 aromatic ring atoms, which may be substituted by one or more radicals R$^1$, or a diarylamino group, diheteroarylamino group or arylheteroarylamino group having 10 to 40 aromatic ring atoms, which may be substituted by one or more radicals R$^1$; two or more radicals R here may also form a mono- or polycyclic, aliphatic, aromatic and/or benzo-fused ring system with one another;

R$^1$ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R$^1$ here may also form a mono- or polycyclic, aliphatic or aromatic ring system with one another;

n is 1, 2, 3 or 4;

m is 1, 2 or 3;

q, r is, identically or differently on each occurrence, 0, 1, 2 or 3;

wherein at least two of the groups Ar$^4$ to Ar$^7$ are each substituted by a group of the following formula (7):

-L-(Ar$^8$)$_p$-Q    formula (7)

in which:

L is, identically or differently on each occurrence, a spacer group or a direct bond;

Ar$^8$ is, identically or differently on each occurrence, an aromatic or heteroaromatic ring system having 5 to 24 aromatic ring atoms, which may be substituted by one or more radicals R;

Q is, identically or differently on each occurrence, a crosslinkable group;

p is, identically or differently on each occurrence, 0 or 1.

2. The compound according to claim 1, wherein the group Ar$^1$ is selected, identically or differently on each occurrence, from the groups of the formulae (8) to (27),

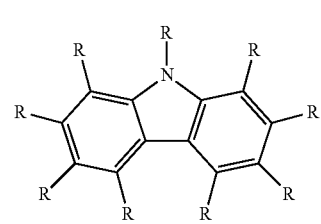

formula (8)

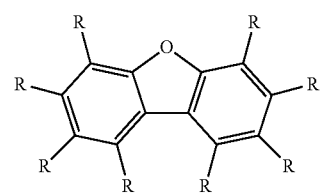

formula (9)

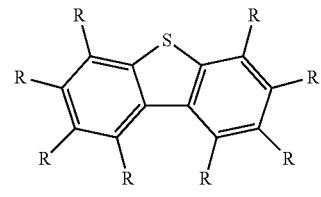

formula (10)

formula (11)
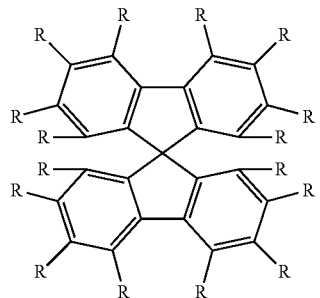
formula (12)
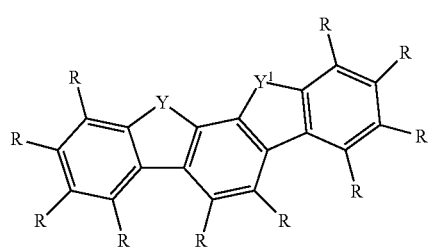
formula (13)
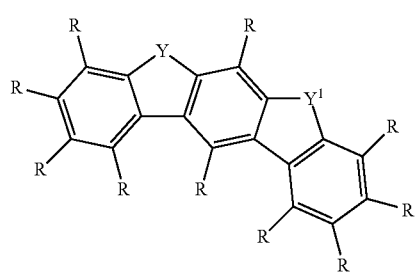
formula (14)
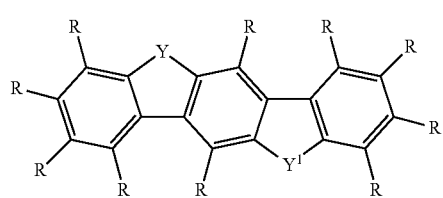
formula (15)
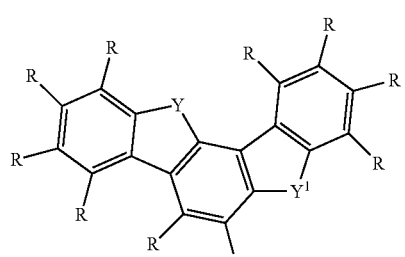
formula (16)
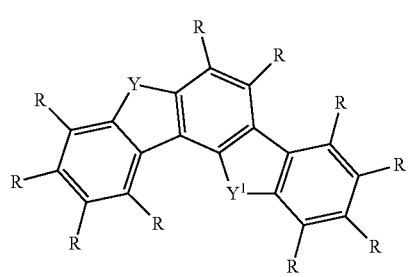
formula (17)
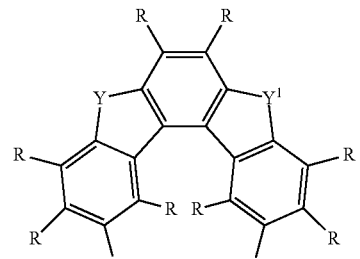
formula (18)
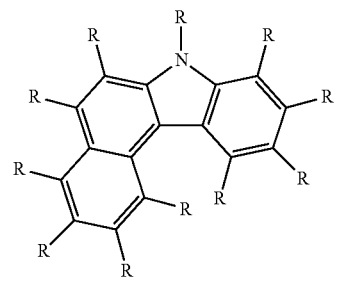
formula (19)
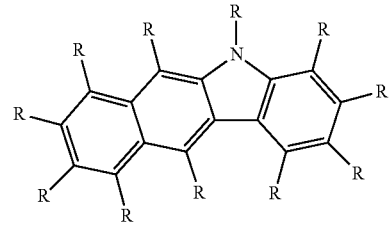
formula (20)
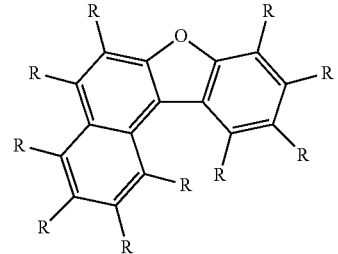
formula (21)
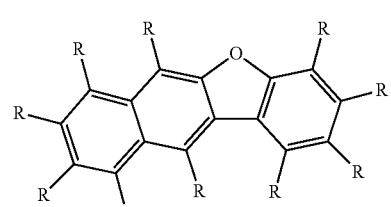
formula (22)
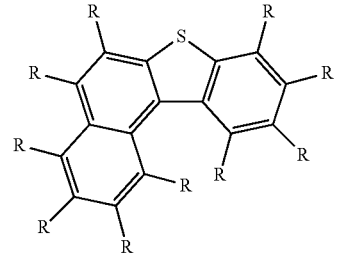

-continued

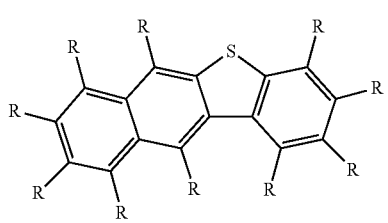
formula (23)

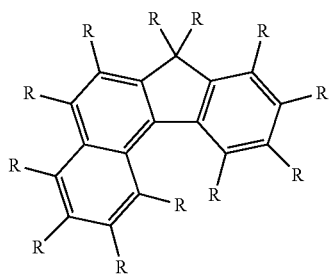
formula (24)

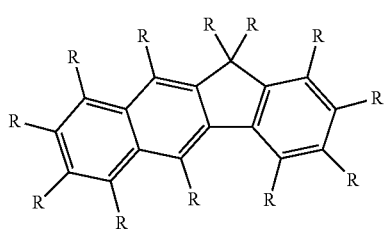
formula (25)

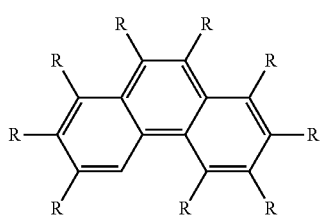
formula (26)

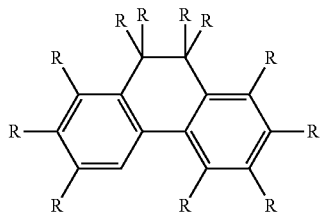
formula (27)

where Y, $Y^1$ and R have the meanings given in claim 1, and no radical R is present at the positions at which the structure is bonded to $Ar^2$ or $Ar^3$ or to the nitrogen or to a further group $Ar^1$ for n>1; the groups can each be bonded via any desired positions.

3. The compound according to claim 1, wherein the group $Ar^1$ is selected, identically or differently on each occurrence, from the structures of the formulae (8a) to (27b),

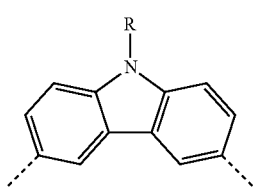
formula (8a)

-continued

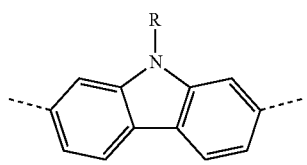
formula (8b)

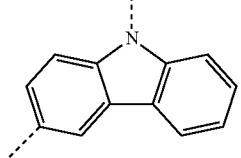
formula (8c)

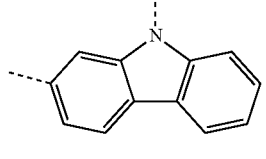
formula (8d)

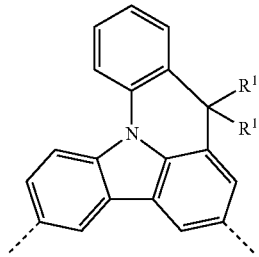
formula (8e)

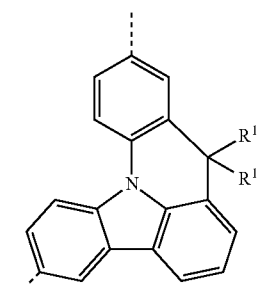
formula (8f)

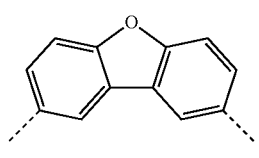
formula (9a)

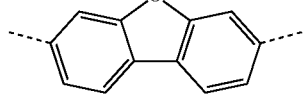
formula (9b)

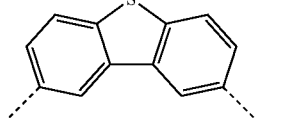
formula (10a)

formula (10b)

-continued
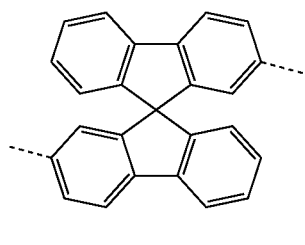
formula (1ba)
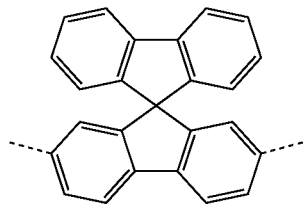
formula (11c)
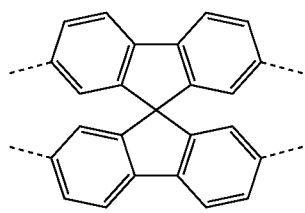
formula (11d)
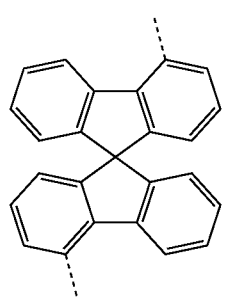
formula (11e)
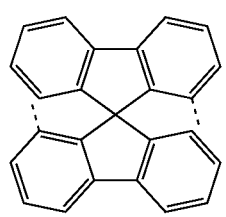
formula (11f)
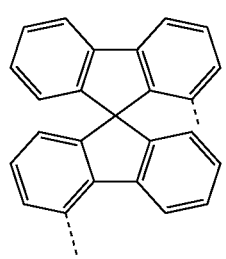
-continued
formula (11g)
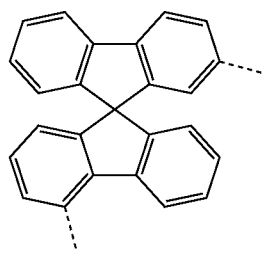
formula (11h)
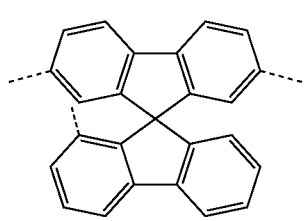
formula (11i)
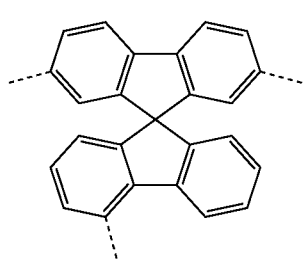
formula (12a)
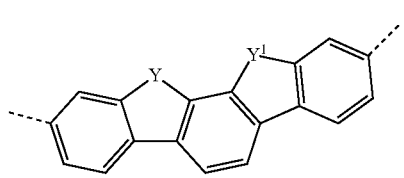
formula (12b)
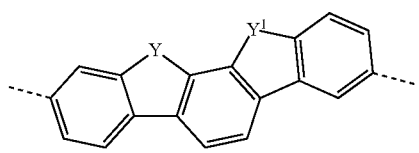
formula (12c)
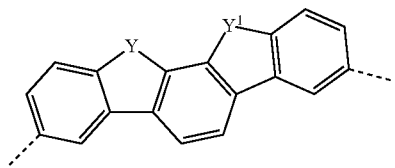
formula (13a)
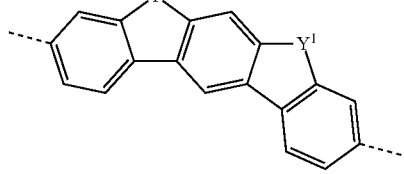

formula (13b)
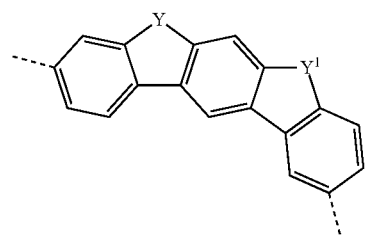
formula (13c)
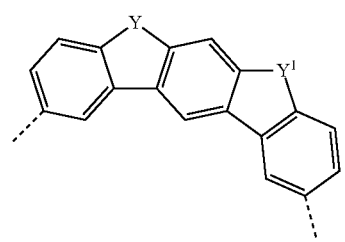
formula (14a)
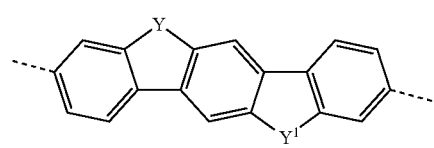
formula (14b)
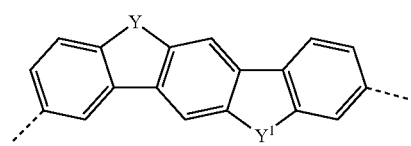
formula (14c)
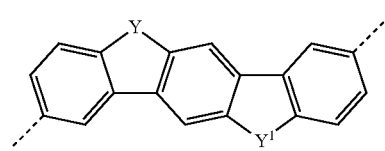
formula (15a)
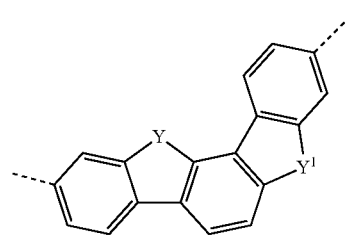
formula (15b)
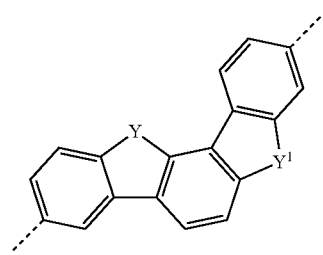
formula (15c)
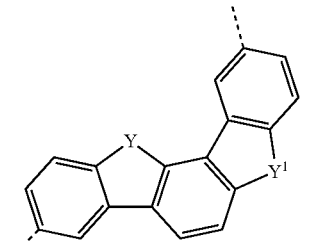
formula (16a)
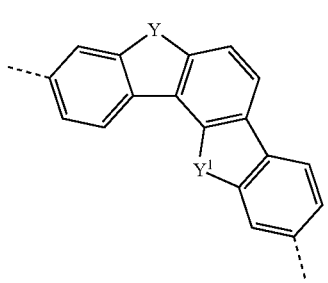
formula (16b)
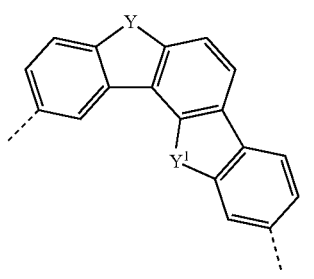
formula (16c)
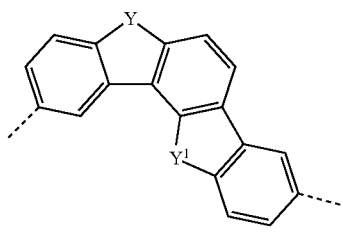
formula (17a)
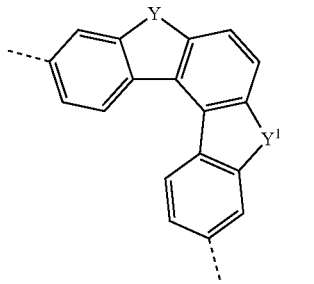
formula (17b)
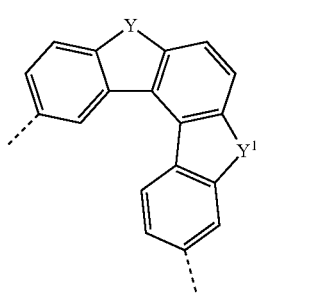

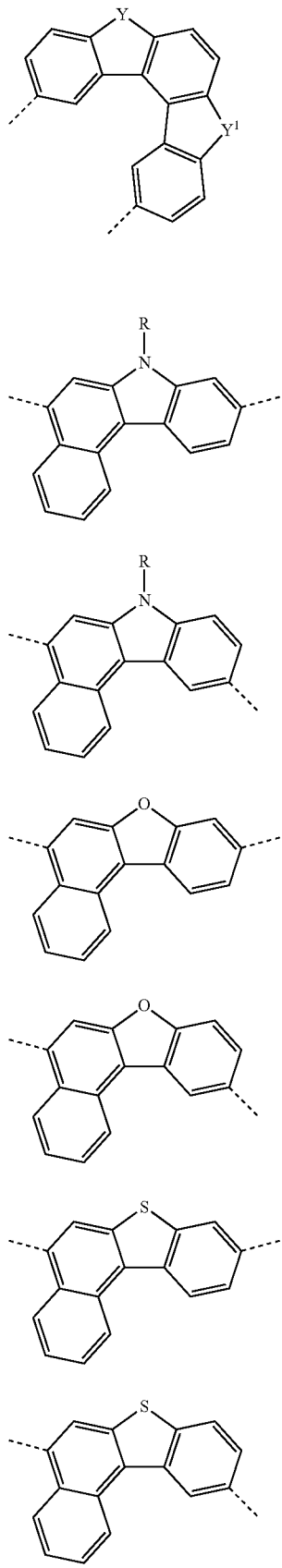
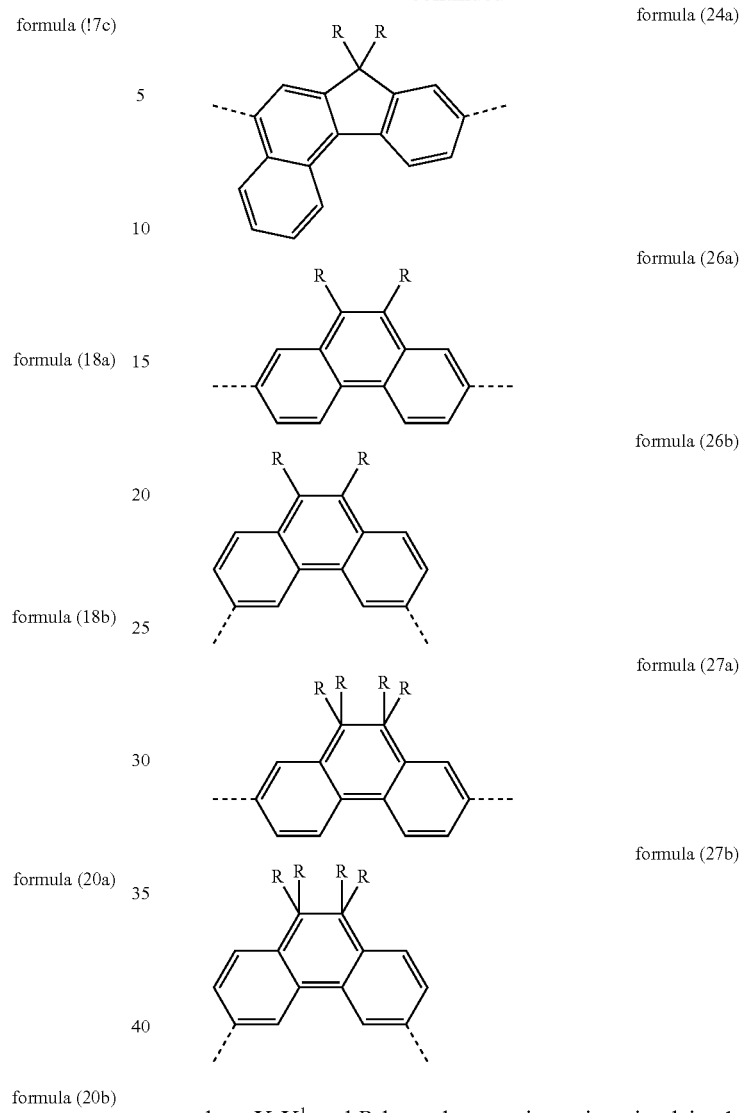

where Y, Y¹ and R have the meanings given in claim 1, and the dashed bond indicates the position at which the structure is bonded to Ar² or Ar³ or to the nitrogen or to Ar¹ for n>1.

4. The Compound according to claim 1, wherein Ar² and Ar³ is selected, identically or differently on each occurrence, from 1,2-phenylene, 1,3-phenylene or 1,4-phenylene, each of which may be unsubstituted or substituted by one or more radicals R.

5. The compound according to claim 1, wherein the compound contains between 2 and 8 groups of the formula (7).

6. The compound according to claim 1, wherein L is a single bond or L is a linear or branched alkylene group having 1 to 20 C atoms, in which one or more non-adjacent CH₂ groups may be replaced by —O—, —S—, —NH—, —N(CH₃)—, —N—CO—, —N—CO—O—, —N—CO—N, —CO—, —O—CO—, —S—CO—, —O—COO—, —CO—S—, —CO—O—, —CH(halogen)-, —CH(CN)—, —CH═CH— or —C≡C—, or a cyclic alkyl group.

7. The compound according to claim 1, wherein Ar⁸ is selected from 1,2-phenylene, 1,3-phenylene or 1,4-phenylene, each of which may be unsubstituted or substituted by one or more radicals R.

8. The compound according to claim 1, wherein the group Q is selected from terminal or cyclic alkenyl groups, terminal alkynyl groups, arylvinyl groups, acrylic acid derivatives, alkenyloxy or perfluoroalkenyloxy derivatives, groups which undergo a ring-opening polymerisation, in particular oxetane and oxirane derivatives, or silanes.

9. A compound or layer obtained by crosslinking the groups Q of the compound according to claim 1, where the crosslinking is optionally carried out in a layer.

10. A process for the production of a crosslinked layer, comprising applying the compound according to claim 1 from solution to form a layer, and crosslinking the layer.

11. A method comprising utilizing the compound according to claim 1 in an electronic device.

12. A method comprising utilizing the compound or layer according to claim 9 in an electronic device.

13. An electronic device comprising one or more compounds according to claim 1 in an electronic device.

14. An electronic device comprising the compound or layer according to claim 9 in an electronic device.

15. The electronic device according to claim 14, wherein the device is an organic electroluminescent device, comprising the following structure: anode/optionally layer comprising a conductive polymer/one or more layers according to claim 9/emission layer and cathode.

16. The electronic device according to claim 13, wherein on or more compounds according to claim 1 are used in a hole-transport layer or in a hole-injection layer, where this layer may also be doped.

17. The electronic device according to claim 13, wherein the compounds according to claim 9 are used in a hole-transport layer or in a hole-injection layer, where this layer may also be doped.

18. A formulation comprising at least one compound according to claim 1 and one or more solvents.

* * * * *